(12) United States Patent
Alihodzic et al.

(10) Patent No.: US 8,080,529 B2
(45) Date of Patent: Dec. 20, 2011

(54) MACROLIDES WITH ANTI-INFLAMMATORY ACTIVITY

(75) Inventors: Sulejman Alihodzic, Strmec Samoborski (HR); Martina Bosnar, Zagreb (HR); Ognjen Culic, Zagreb (HR); Vesna Erakovic Haber, Rijeka (HR); Antun Hutinec, Zagreb (HR); Dubravko Jelic, Samobor (HR); Goran Kragol, Zagreb (HR); Nikola Marjanovic, Zagreb (HR); Zorica Marusic-Istuk, Samobor (HR); Marija Ribic, Durmanec (HR); Vanja Vela, Zagreb (HR)

(73) Assignee: Glaxo Group Limited, Greenford, Middlesex (GB)

( * ) Notice: Subject to any disclaimer, the term of this patent is extended or adjusted under 35 U.S.C. 154(b) by 831 days.

(21) Appl. No.: 11/813,873

(22) PCT Filed: Jan. 13, 2006

(86) PCT No.: PCT/IB2006/001238
§ 371 (c)(1),
(2), (4) Date: Jul. 13, 2007

(87) PCT Pub. No.: WO2006/087644
PCT Pub. Date: Aug. 24, 2006

(65) Prior Publication Data
US 2008/0221046 A1      Sep. 11, 2008

Related U.S. Application Data

(60) Provisional application No. 60/643,841, filed on Jan. 13, 2005, provisional application No. 60/715,828, filed on Sep. 9, 2005.

(51) Int. Cl.
*A61K 31/70*     (2006.01)
*C07H 17/08*    (2006.01)

(52) U.S. Cl. .......................................... 514/29; 536/7.4
(58) Field of Classification Search .................. 536/7.4
See application file for complete search history.

(56) References Cited

U.S. PATENT DOCUMENTS

| 5,250,518 | A  | * | 10/1993 | Kobrehel et al. ............... 514/29 |
| 6,110,965 | A  |   | 8/2000  | Lazarevski et al. |
| 7,910,559 | B2 |   | 3/2011  | Culic et al. |
| 2008/0241959 | A1 | | 10/2008 | Culic et al. |
| 2010/0197623 | A1 | | 8/2010  | Day et al. |

FOREIGN PATENT DOCUMENTS

| EP | 0 126 344    | 11/1984 |
| EP | 0 895 999    | 2/1999  |
| WO | 99/51616 A1  | 10/1999 |
| WO | 2004/005310  | 1/2004  |
| WO | 2004/101586  | 11/2004 |
| WO | 2006/077501 A2 | 7/2006 |
| WO | 2006/106440 A1 | 10/2006 |
| WO | 2010/086349 A1 | 8/2010 |

OTHER PUBLICATIONS

Culic et al., "Anti-Inflammatory effects of macrolide antibiotics," *European Journal of Pharmacology*, V 429 N1-3, 2001, pp. 209-229.

* cited by examiner

*Primary Examiner* — Elli Peselev
(74) *Attorney, Agent, or Firm* — Karen L. Prus

(57) ABSTRACT

The present invention relates to novel semi-synthetic macrolides having anti-inflammatory activity. More particularly, the invention relates to 14- and 15-membered macrolides substituted at the 4" position, to their pharmaceutically acceptable derivatives, to processes and intermediates for their preparation, to pharmaceutical compositions containing them and to their activity and use in the treatment of inflammatory diseases and conditions in humans and animals, especially those diseases associated with excessive secretion of TNF-α, IL-1, IL-8, IL-2 or IL-5; and/or inhibitor of excessive lymphocyte proliferation; and/or excessive granulocyte degranulation.

24 Claims, No Drawings

MACROLIDES WITH ANTI-INFLAMMATORY ACTIVITY

This application is filed pursuant to 35 U.S.C. §371 as a U.S. National Phase Application of International Application No. PCT/IB2006/001238 filed Jan. 13, 2006, which claims priority from U.S. 60/643,841 filed Jan. 13, 2005 and 60/715,828 filed Sep. 9, 2005.

This application claims priority to U.S. Provisional Application No. 60/643,841 filed Jan. 13, 2005, and U.S. Provisional Application 60/715,828 filed Sep. 9, 2005, each of which are incorporated herein by reference in their entirety.

FIELD OF THE INVENTION

The present invention relates to substituted macrolides having anti-inflammatory activity, their pharmaceutically acceptable derivatives, and to methods of use thereof.

TECHNICAL PROBLEM

The invention is directed to solving the technical problem of providing novel targeted anti-inflammatory agents. More specifically, the invention provides anti-inflammatory agents wherein the active substance is neither a steroid nor an NSAID. The compounds of the invention are responsive to this problem by virtue of their anti-inflammatory activity and their ability to accumulate in various immune cells recruited to the locus of inflammation.

BACKGROUND OF THE INVENTION

Inflammation is the final common pathway of various insults, such as infection, trauma, allergies to the human body. It is characterized by activation of the immune system with recruitment of inflammatory cells, production of pro-inflammatory cells and production of pro-inflammatory cytokines.

Most inflammatory diseases are characterized by abnormal accumulation of inflammatory cells including monocytes/macrophages, granulocytes, plasma cells, lymphocytes and platelets. Along with tissue endothelial cells and fibroblasts, these inflammatory cells release a complex array of lipids, growth factors, cytokines and destructive enzymes that cause local tissue damage.

One form of inflammatory response is neutrophilic inflammation which is characterized by infiltration of the inflamed tissue by neutrophil polymorphonuclear leucocytes (PMN), which are a major component of host defense. Tissue infection by extracellular bacteria represents the prototype of this inflammatory response. On the other hand, various non-infectious diseases are characterized by extravascular recruitment of neutrophils. This group of inflammatory diseases includes chronic obstructive pulmonary disease, adult respiratory distress syndrome, some types of immune-complex alveolitis, cystic fibrosis, bronchitis, bronchiectasis, emphysema, glomerulonephritis, rheumatoid arthritis, gouty arthritis, ulcerative colitis, certain dermatoses such as psoriasis and vasculitis. In these conditions neutrophils are thought to play a crucial role in the development of tissue injury which, when persistent, can lead to the irreversible destruction of the normal tissue architecture with consequent organ dysfunction. Tissue damage is primarily caused by the activation of neutrophils followed by their release of proteinases and increased production of oxygen species.

Chronic obstructive pulmonary disease (COPD) is described by the progressive development of airflow limitation that is not fully reversible (ATC, 1995). Most patients with COPD have three pathological conditions: bronchitis, emphysema and mucus plugging. This disease is characterized by a slowly progressive and irreversible decrease in forced expiratory volume in the first second of expiration (FEVI), with relative preservation of forced vital capacity (FVC) (Barnes, *N. Engl. J. Med.* (2000), 343(4): 269-280). In both asthma and COPD there is significant, but distinct, remodeling of airways. Most of the airflow obstruction is due to two major components, alveolar destruction (emphysema) and small airways obstruction (chronic obstructive bronchitis). COPD is mainly characterized by profound mucus cell hyperplasia.

Cigarette smoking, air pollution and other environmental factors are major causes of the disease. The causal mechanism remains currently undefined but oxidant-antioxidant disturbances are strongly implicated in the development of the disease. COPD is a chronic inflammatory process that differs markedly from that seen in asthma, with different inflammatory cells, mediators, inflammatory effects, and responses to treatment (Keatings et al, *Am. J. Respir. Crit. Care Med.* (1996), 153: 530-534). Neutrophil infiltration of the patient's lungs is a primary characteristic of COPD.

Elevated levels of proinflammatory cytokines like TNF-α, and especially chemokines like IL-8 and GRO-α play a very important role in pathogenesis of this disease. Platelet thromboxane synthesis is also enhanced in patients with COPD (Keatings et al., *Am. J. Respir. Crit. Care Med.* (1996), 153: 530-534; Stockley and Hill, *Thorax* (2000), 55(7): 629-630). Most of the tissue damage is caused by activation of neutrophils followed by their release of (metallo)proteinases, and increased production of oxygen species (Repine et al., *Am. J. Respir. Crit. Care Med.* (1997), 156: 341-357; Barnes, *Chest* (2000), 117(2 Suppl): 10S-14S).

Most therapeutic endeavour is directed towards the control of symptoms (Barnes, *Trends Pharm. Sci.* (1998), 19(10): 415-423; Barnes, *Am. J. Respir. Crit. Care Med.* (1999) 160: S72-S79; Hansel et al., *Expert Opin. Investig. Drugs* (2000) 9(1): 3-23). Symptoms usually equate with airflow limitation and bronchodilators are the conventional therapy of choice. Prevention and treatment of complications, prevention of deterioration and improved quality and length of life are also primary goals stated in the three key international guidelines for the management of COPD (Culpitt and Rogers, *Exp. Opin. Pharmacother.* (2000) 1(5): 1007-1020; Hay, *Curr. Opin. Chem. Biol.* (2000), 4: 412-419). Basically, most of the current therapeutic research has been focused on mediators involved in the recruitment and activation of neutrophils, or attenuation of consequences of their undesirable activation (Stockley et al., *Chest* (2000), 117(2 Suppl): 58S-62S).

In 1975, TNF-α was defined as an endotoxin-induced serum factor causing tumor necrosis in vitro and in vivo (Carswell E. A. et al. *Proc. Natl. Acad. Sci. U.S.A.* 1975, 72, 3666-3670). In addition to antitumor activity, TNF-α has several other biologic activities that are important in homeostasis as well as in pathophysiological conditions. The main sources of TNF-α are monocytes-macrophages, T-lymphocytes and mast cells.

The finding that anti-TNF-α antibodies (cA2) are effective in the treatment of patients suffering from rheumatoid arthritis (RA) (Elliot M. et al. *Lancet* 1994, 344, 1105-1110) intensified the interest to find new TNF-α inhibitors as possible potent medicaments for RA. Rheumatoid arthritis is an autoimmune chronic inflammatory disease characterized by irreversible pathological changes of the joints. In addition to RA, TNF-α antagonists are also applicable to several other pathological conditions and diseases such as spondylitis, osteoarthritis, gout and other arthritic conditions, sepsis, septic shock, toxic shock syndrome, atopic dermatitis, contact dermatitis, psoriasis, glomerulonephritis, lupus erhythematosus, sclerodenna, asthma, cachexia, chronic obstructive lung disease, congestive heart failure, insulin resistance, lung fibrosis, multiple sclerosis, Crohn's disease, ulcerative colitis, viral infections and AIDS.

The interest of the scientific community has recently turned towards the immunomodulating and anti-inflammatory activities of the macrolide antibiotics (*Journal of Antimicrobial Chemotherapy*, 1988, 41, Suppl. B, 37-46).

An ideal immunomodulating agent should be able to suppress the deleterious effects of the inflammatory response, while leaving the protective immune responses intact.

Macrolide antibiotics accumulate preferentially within different cells of subjects, especially within phagocyte cells such as mononuclear peripheral blood cells, and peritoneal and alveolar macrophages. (Gladue, R. P. et al, *Antimicrob. Agents Chemother.* 1989, 33, 277-282; Olsen, K. M. et al, *Antimicrob. Agents Chemother.* 1996, 40, 2582-2585). Anti-inflammatory effects of some macrolides have been described in the literature. For example, the anti-inflammatory effect of erythromycin derivatives (*J. Antimicrob. Chemother.* 1998, 41, 37-46; WO Patent Application No. 00/42055). Taisho claims further anti-inflammatory erythromycin derivatives modified in positions 3, 9, 11 and 12 (EP 0775489 and EP 0771564). In the patent application WO 02/087596, there is a good description of the anti-inflammatory activity of azithromycin, a known antibacterial agent. Azithromycin derivatives lacking the sugar moieties cladinose and desosamine and having anti-inflammatory activity have been described (Pliva, U.S. Pat. No. 4,886,792). International patent applications WO 04/039821 and WO 04/013153 (Zambon Group) disclose macrolide and azalide derivatives lacking cladinose sugar that exhibit anti-inflammatory but not antibacterial activity.

Anti-inflammatory effects of some macrolides are also known from in vitro and in vivo studies in experimental animal models such as in zymosan-induced peritonitis in mice (*J. Antimicrob. Chemother.* 1992, 30, 339-348) and endotoxin-induced neutrophil accumulation in rat trachea (*J. Immunol.* 1997, 159, 3395-4005). The modulating effect of macrolides upon cytokines such as interleukin 8 (IL-8) (*Am. J. Respir. Crit. Care. Med.* 1997, 156, 266-271) and interleukin 5 (IL-5) (EP Pat. No. 0775489 and EP Pat. No. 771564) is known as well.

Macrolides have proved to be useful in the treatment of inflammatory pathologies such as panbronchiolitis (Thorax, 1997, 52, 915-918), bronchial asthma (Chest, 1991, 99 670-673), and azithromycin in particular has proved effective in improving lung function in patients with cystic fibrosis (The Lancet, 1998, 351, 420).

The administration of macrolides to asthmatics is accompanied by a reduction in hypersecretion and in bronchial hypersensitivity resulting from the macrolides, anti-oxidative and anti-inflammatory interaction with phagocytes and in particular with neutrophilis (Inflammation, Vol. 20, No. 6, 1996).

SUMMARY OF THE INVENTION

New 14- and 15-membered macrolide compounds substituted at the 4" position of cladinose sugar moiety, represented by the Formula (I), representing the subject of the present invention, their pharmaceutically acceptable derivatives and pharmaceutical compositions comprising them have hitherto not been described. Moreover, no compound representing the subject of the present invention has been described either as an anti-inflammatory substance or as an inhibitor of one or more of TNF-α, IL-1 (IL-1-α or IL-1-β), IL-6, IL-8, IL-2 or IL-5; and/or inhibitor of excessive lymphocyte proliferation; and/or excessive granulocyte degranulation. Consequently, the use of such compounds to combat inflammatory states has not been described or suggested. Nor has there been a description or suggestion of pharmaceutical dosage forms containing effective amounts of a 14- and 15-membered macrolide compounds substituted at the 4" position for treating inflammatory states in a mammalian subject, including a human.

A characteristic of compounds represented by Formula (I) is selective accumulation in target organs and cells in the above mentioned inflammatory diseases and conditions. These pharmacokinetic properties enable the compounds represented by Formula I to act at the inflammation site in inflammation cells by inhibiting the production of inflammation mediators. In such a manner, the unfavourable systemic side-effects that are characteristic of corticosteroids or non-steroidal anti-inflammatory molecules are avoided and the therapeutic action of compounds represented by Formula (I) is targeted to the area where it is most needed. Following local or systemic application, molecules rapidly accumulate in inflammation cells wherein they act by inhibiting the production of cytokines and chemokines and/or other inflammatory mediators thus suppressing the inflammation.

Thus, the present invention is directed to:
(a) compounds represented by Formula (I)

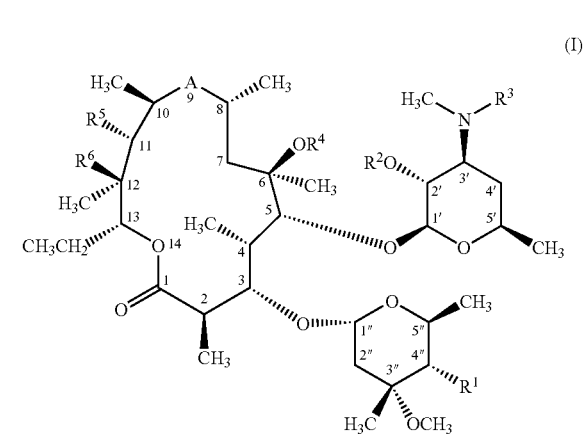

(I)

wherein
A is a bivalent radical selected from —C(O)—, —NHC(O)—, —C(O)NH—, —N(R$^7$)CH$_2$—, —CH$_2$N(R$^7$)—, —CH(OH)— and —C(=NOR$^7$)—;
R$^1$ is —OC(O)(CH$_2$)$_n$NR$^8$R$^9$, —O—(CH$_2$)$_n$NR$^8$R$^9$, —OC(O)N(R$^7$)(CH$_2$)$_n$NR$^8$R$^9$,

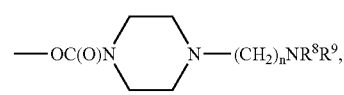

—O(CH$_2$)$_n$CN, —OC(O)(CH$_2$)$_n$N(CH$_2$)$_n$NR$^8$R$^9$, or —OC(O)CH=CH$_2$ with the proviso that if R$^1$ is —OC(O)CH=CH$_2$, R$^3$ cannot be methyl;
R$^2$ is hydrogen or a hydroxyl protecting group;
R$^3$ is hydrogen, unsubstituted C$_{1-4}$ alkyl or C$_{1-4}$ alkyl substituted at terminal carbon atom with CN or NH$_2$ group, or C$_{1-5}$ alkanoyl;

$R^4$ is hydrogen, $C_{1-4}$ alkyl or $C_{2-6}$ alkenyl or a hydroxyl protecting group 1;
$R^5$ is hydroxy, methoxy group, —OC(O)(CH$_2$)$_n$NR$^8$R$^9$—O—(CH$_2$)$_n$NR$^8$R$^9$ or —O(CH$_2$)$_n$CN;
$R^6$ is hydroxy; or
$R^5$ and $R^6$ taken together with the intervening atoms form a cyclic group having the following structure:

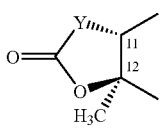

wherein Y is a bivalent radical selected from —CH$_2$—, —CH(CN)—, —O—, —N(R$^7$)— and —CH(SR$^7$)—;
$R^7$ is hydrogen or $C_{1-6}$alkyl;
$R^8$ and $R^9$ are each independently hydrogen, $C_{3-7}$ cycloalkyl, $C_{1-18}$ alkyl, wherein $C_{1-18}$ alkyl is:
(i) uninterrupted or interrupted by 1-3 bivalent radical groups selected from —O—, —S— and —N(R$^7$)—; and/or
(ii) unsubstituted or substituted by 1-3 groups selected from halogen, OH, NH$_2$, N—(C$_1$-C$_6$)alkylamino (preferably N-methylamino or N-ethylamino), N,N-di(C$_1$-C$_6$-alkyl) amino (preferably dimethylamino, diethylamino or di-isopropylamino), CN, NO$_2$, OCH$_3$, a C$_{3-8}$ membered non-aromatic ring which is saturated or unsaturated a non-aromatic heterocyclic ring containing 2-6 carbon atoms which is saturated or unsaturated containing from 1-2 heteroatoms selected from oxygen, sulphur and nitrogen, alkylcarbonylalkoxy and alkoxycarbonylamino; or
$R^8$ and $R^9$ taken together with nitrogen to which they are attached form a non-aromatic heterocyclic ring containing 2-6 carbon atoms which is:
  i) saturated or unsaturated containing from 0 or 1 additional heteroatoms selected from oxygen, sulphur and nitrogen; and/or
  ii) unsubstituted or substituted by 1-2 groups selected from $C_{1-5}$alkanoyl and $C_{1-6}$alkyl, wherein $C_{1-6}$alkyl is uninterrupted or is interrupted by 1-3 bivalent radical groups selected from —O—, —S— and —N(R$^7$)—, and/or being unsubstituted or substituted by 1-2 groups selected from OH, NH$_2$, a non-aromatic heterocyclic ring containing 2-6 carbon atoms which is unsubstituted or is substituted by group selected from $C_{1-4}$ alkyl, halo, NH$_2$, OH, SH, $C_{1-6}$ alkoxy and $C_{1-4}$ hydroxyalkyl, a $C_{3-7}$ cycloalkyl which is unsubstituted or is substituted by group selected from $C_{1-4}$ alkyl, halo, NH$_2$, OH, SH, $C_{1-6}$ alkoxy and $C_{1-4}$ hydroxyalkyl;
n is an integer from 1 to 8;
and pharmaceutically acceptable derivatives of the Formula I compounds;
  (b) compositions containing one or more of the foregoing compounds in an amount effective to reduce inflammation and thereby treat disorders and conditions involving inflammation in mammals, including humans;
  (c) methods for using these compounds to treat such disorders and conditions, uses of these compounds in the treatment of such disorders and conditions and in the preparation of medicaments for that purpose; and
  (d) methods of inhibiting inflammatory process such as proinflammatory cytokine production, excessive lymphocyte proliferation, and excessive granulocyte degranulation, t-cell proliferation, immune response to an antigen, neutrophilia, or oedema

DETAILED DESCRIPTION OF THE INVENTION

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. However, since the macrolides are highly soluble, aqueous solutions are preferred. Suitable pharmaceutical carriers are described in "Remington's Pharmaceutical Sciences" by E. W. Martin, 18th Edition, incorporated by reference. Particularly preferred for the present invention are carriers suitable for immediate-release, i.e., release of most or all of the active ingredient over a short period of time, such as 60 minutes or less, and make rapid absorption of the drug possible.

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters.

The compounds of the present invention may be in the form of and/or may be administered as a pharmaceutically acceptable salt. For a review on suitable salts see Berge et al., J. Pharm. Sci., 1977, 66, 1-19, incorporated by reference.

Typically, a pharmaceutical acceptable salt may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula (I) and the resulting mixture evaporated to dryness (lyophilised) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulfonates (e.g. methanesulfonate, ethanesulfonate, benzenesulfonate or p-toluenesulfonate) and isothionate. Representative examples include trifluoroacetate and formate salts, for example the bis- or tris-trifluoroacetate salts and the mono or diformate salts, in particular the bis- or tris-trifluoroacetate salt and the monoformate salt.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Compounds of the invention may have both a basic and an acidic center and may therefore be in the form of zwitterions.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the compound of formula (I) may form solvates (e.g. hydrates) and the invention also includes all such solvates.

The term "prodrug" as used herein means a compound which is converted within the body, e.g. by hydrolysis in the blood, into its active form that has medical effects. Pharmaceutically acceptable prodrugs are described in T. Higuchi and V. Stella, "Prodrugs as Novel Delivery Systems", Vol. 14 of the A.C.S. Symposium Series, Edward B. Roche, ed., "Bioreversible Carriers in Drug Design", American Pharmaceutical Association and Pergamon Press, 1987, and in D. Fleisher, S. Ramon and H. Barbra "Inproved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of one or more of alcohol, sulfhydryl and amine functional groups of the compounds of structure (I). Further, in the case of a carboxylic acid (—COOH) group, esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

References hereinafter to a compound according to the invention include both compounds of formula (I) and their pharmaceutically acceptable derivatives.

With regard to stereoisomers, the compounds of structure (I) have more than one asymmetric carbon atom. In the general formula (I) as drawn, the solid wedge shaped bond indicates that the bond is above the plane of the paper. The broken bond indicates that the bond is below the plane of the paper.

It will be appreciated that the substituents on the macrolide may also have one or more asymmetric carbon atoms. Thus, the compounds of structure (I) may occur as individual enantiomers or diastereomers. All such isomeric forms are included within the present invention, including mixtures thereof.

Where a compound of the invention contains an alkenyl group, cis (Z) and trans (E) isomerism may also occur. The present invention includes the individual stereoisomers of the compound of the invention and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. An enantio- and diastereopure or enriched agent may also be prepared from a corresponding optically pure intermediate or by resolution, such as H.P.L.C., of the corresponding racemate using a suitable chiral support or by fractional crystallisation of the diastereoisomeric salts formed by reaction of the corresponding racemate with a suitable optically active acid or base, as appropriate.

The compounds of Formula (I) may be in crystalline or amorphous form. Furthermore, some of the crystalline forms of the compounds of Formula (I) may exist as polymorphs, which are included in the present invention.

Compounds wherein $R^2$ represents a hydroxyl protecting group are in general intermediates for the preparation of other compounds of Formula (I).

When the group $OR^2$ is a protected hydroxyl group this is conveniently an ether or an acyloxy group. Examples of particularly suitable ether groups include those in which $R^2$ is a trialkylsilyl (i.e. trimethylsilyl). When the group $OR^2$ represents an acyloxy group, then examples of suitable groups $R^2$ include acetyl, benzoyl or benzyloxycarbonyl.

The term "alkyl" as used herein as a group or a part of a group refers to a straight or branched hydrocarbon chain containing the specified number of carbon atoms. For example, $C_{1-6}$ alkyl means a straight or branched alkyl chain containing from 1 to 6 carbon atoms; examples of such group include methyl, ethyl, propyl, isopropyl, n-butyl, isobutyl, tert-butyl, pentyl, 3-methyl-butyl, hexyl and 2,3-dimethylbutyl and like.

When an alkyl chain is interrupted by 1-3 of —O—, —S— or —N($R^7$)— a methylene spacer can be present adjacent to an interrupting moiety. Thus, this would include, for example, —CH$_2$—O— and —O—CH$_2$—. When two or three of these interrupting moieties are present, they are separated from one another by at least one methylene spacer.

The term "alkenyl" as used herein as a group or a part of a group refers to a straight or branched hydrocarbon chain containing the specified number of carbon atoms and containing at least one double bond. For example, the term "$C_{2-6}$-alkenyl" means a straight or branched alkenyl containing at least 2, and at most 6, carbon atoms and containing at least one double bond. Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. Interrupting moieties as above can be present within alkenyl chains. It will be appreciated that in groups of the form —O—$C_{2-6}$ alkenyl, the double bond is preferably not adjacent to the oxygen.

The term "$C_{1-5}$ alkanoyl" refers to acyl group such as formyl, acetyl, propanoyl or butanoyl.

The term "halogen" refers to a fluorine, chlorine, bromine or iodine atom.

The term "$C_{3-7}$ cycloalkyl" group as used herein refers to a non-aromatic monocyclic hydrocarbon ring of 3 to 7 carbon atoms such as, for example, cyclopropyl, cyclobutyl, cyclopentyl, cyclohexyl or cycloheptyl.

The term "alkoxy" as used herein refers to a straight or branched chain alkoxy group containing the specified number of carbon atoms. For example, $C_{1-6}$ alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy.

The term "hydroxyalkyl" as used herein as a group refers to a straight or branched hydrocarbon chain containing the specified number of carbon atoms, which is substituted by 1-3 hydroxyl groups. For example, $C_{1-4}$ hydroxyalkyl means a straight or branched alkyl chain containing from 1 to 4 carbon atoms and at least one hydroxyl group; examples of such groups include hydroxymethyl, hydroxyethyl, hydroxypropyl, hydroxyisopropyl, hydroxybutyl and like.

The term "heterocyclic" as used herein, refers to a non-aromatic, saturated or unsaturated monocycle, containing two- to six carbon atoms and at least one heteroatom selected from oxygen, nitrogen and sulfur. Preferably, the heterocyclyl ring has five to seven ring atoms. Examples of heterocyclyl groups include, but are not limited to, pyrrolidinyl, tetrahydrofuranyl, tetrahydrothiophenyl, imidazolidinyl, pyrazolidinyl, piperidinyl, piperazinyl, homopiperazinyl, hexamethyleneiminyl, morpholinyl, tetrahydropyranyl and thiomorpholinyl.

The term "leaving group" refers to a chemical group which is capable of being displaced by a nucleophile. Examples of such groups include but are not limited to halogen, mesylate, tosylate and ester groups.

In some preferred embodiments, this invention relates to the compounds of Formula (I) and to pharmaceutically acceptable derivatives thereof wherein A represent —NHC(O)— or —C(O)NH—. Within this subset, all other variables are as originally defined.

Another preferred aspect of the invention relates to the compounds of Formula (I) and to pharmaceutically acceptable derivatives thereof wherein A represent —N($R^7$)$CH_2$— or —$CH_2$N($R^7$)—. Within this subset, all other variables are as originally defined.

Yet another preferred aspect of the invention relates to the compounds of Formula (I) and to pharmaceutically acceptable derivatives thereof wherein A represent —C(O)—, —CH(OH)—, or —C(=N$OR^7$)—. Within this subset, all other variables are as originally defined.

Representative examples of $R^3$ include hydrogen, unsubstituted $C_{1-4}$ alkyl, for example methyl, substituted $C_{1-4}$ alkyl, for example $C_{1-4}$ aminoalkyl or $C_{1-4}$ cyanoalkyl and $C_{1-5}$ alkanoyl, for example acetyl.

A preferred aspect of the invention relates to the compounds of Formula (I) and to pharmaceutically acceptable derivatives thereof wherein $R^4$ is hydrogen or methyl.

In one embodiment, $R^5$ is hydroxy or methoxy and $R^6$ is hydroxy. Alternatively, $R^5$ and $R^6$ taken together with the intervening atoms form a cyclic group having the following structure:

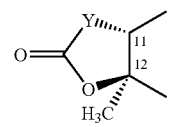

wherein Y is a bivalent radical selected from —O— and —N($R^7$)—.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

"Treating" or "treatment" of a state, disorder or condition includes:
(1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition,
(2) inhibiting the state, disorder or condition, i.e., arresting or reducing the development of the disease or at least one clinical or subclinical symptom thereof, or
(3) relieving the disease, i.e., causing regression of the state, disorder or condition or at least one of its clinical or subclinical symptoms.

The benefit to a subject to be treated is either statistically significant or at least perceptible to the patient or to the physician.

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The four classic symptoms of acute inflammation are redness, elevated temperature, swelling, and pain in the affected area, and impairment or loss of function of the affected organ.

Symptoms and signs of inflammation associated with specific conditions include:
rheumatoid arthritis-pain, swelling, warmth and tenderness of the involved joints; generalized and morning stiffness;
insulin-dependent diabetes mellitus-insulitis; this condition can lead to a variety of complications with an inflammatory component, including: retinopathy, neuropathy, nephropathy; coronary artery disease, peripheral vascular disease, and cerebrovascular disease;
autoimmune thyroiditis-weakness, constipation, shortness of breath, puffiness of the face, hands and feet, peripheral edema, bradycardia;
multiple sclerosis-spasticity, blurry vision, vertigo, limb weakness, paresthesias;
uveoretinitis-decreased night vision, loss of peripheral vision;
lupus erythematosus-joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;

scleroderma-Raynaud's disease; swelling of the hands, arms, legs and face; skin thickening; pain, swelling and stiffness of the fingers and knees, gastrointestinal dysfunction, restrictive lung disease; pericarditis; renal failure;

other arthritic conditions having an inflammatory component such as rheumatoid spondylitis, osteoarthritis, septic arthritis and polyarthritis-fever, pain, swelling, tenderness;

other inflammatory brain disorders, such as meningitis, Alzheimer's disease, AIDS dementia encephalitis-photophobia, cognitive dysfunction, memory loss;

other inflammatory eye inflammations, such as retinitis-decreased visual acuity;

inflammatory skin disorders, such as, eczema, other dermatites (e.g., atopic, contact), psoriasis, burns induced by UV radiation (sun rays and similar UV sources)-erythema, pain, scaling, swelling, tenderness;

inflammatory bowel disease, such as Crohn's disease, ulcerative colitis-pain, diarrhea, constipation, rectal bleeding, fever, arthritis;

asthma-shortness of breath, wheezing;

other allergy disorders, such as allergic rhinitis-sneezing, itching, runny nose conditions associated with acute trauma such as cerebral injury following stroke-sensory loss, motor loss, cognitive loss;

heart tissue injury due to myocardial ischemia-pain, shortness of breath;

lung injury such as that which occurs in adult respiratory distress syndrome-shortness of breath, hyperventilation, decreased oxygenation, pulmonary infiltrates;

inflammation accompanying infection, such as sepsis, septic shock, osteomyelitis, toxic shock syndrome-fever, respiratory failure, tachycardia, hypotension, leukocytosis;

other inflammatory conditions associated with particular organs or tissues, such as nephritis (e.g., glomerulonephritis)-oliguria, abnormal urinalysis;

inflamed appendix-fever, pain, tenderness, leukocytosis;

gout-pain, tenderness, swelling and erythema of the involved joint, elevated serum and/or urinary uric acid;

inflamed gall bladder-abdominal pain and tenderness, fever, nausea, leukocytosis;

chronic obstructive pulmonary disorder (COPD)-shortness of breath, wheezing;

congestive heart failure-shortness of breath, rates, peripheral edema, chronic sinusitis, nasal polyps; cystic fibrosis; diffuse panbronchiolitis; bronchiectasis; bronchiolitis obliterans;

Type II diabetes-end organ complications including cardiovascular, ocular, renal, peripheral vascular disease and coronary artery disease;

lung fibrosis (i.e., pulmonary fibrosis)-hyperventilation, shortness of breath, decreased oxygenation;

vascular disease, such as atherosclerosis and restenosis-pain, loss of sensation, diminished pulses, loss of function; and alloimmunity leading to transplant rejection-pain, tenderness, fever.

Symptoms associated with COPD have been outlined supra.

Subclinical symptoms include without limitation diagnostic markers for inflammation the appearance of which may precede the manifestation of clinical symptoms. One class of subclinical symptoms is immunological symptoms, such as the invasion or accumulation in an organ or tissue of proinflammatory lymphoid cells or the presence locally or peripherally of activated pro-inflammatory lymphoid cells recognizing a pathogen or an antigen specific to the organ or tissue and secreting or inducing pro-inflammatory cytokines. Activation of lymphoid cells can be measured by techniques known in the art.

"Delivering" a therapeutically effective amount of an active ingredient to a particular location within a host means causing a therapeutically effective blood concentration of the active ingredient at the particular location. This can be accomplished, e.g., by local or by systemic administration of the active ingredient to the host.

The term host or subject in need thereof as used herein refers to a mammal preferably a human.

Preferred compounds of the invention are the compounds of examples 1-98 and pharmaceutically acceptable derivatives thereof.

Methods of Preparation:

Compounds of Formula (I) and pharmaceutically acceptable derivatives thereof may be prepared by the general methods outlined hereinafter, said methods constituting a further aspect of the invention. In the following description, the groups $R^1$ to $R^9$, A and n, have the meaning defined for the compounds of Formula (I) unless otherwise stated.

It will be obvious to a person skilled in the art that, in order to avoid interference with any functional groups other than those where structural modifications are to be made, appropriate protection and priority in the synthetic route should be chosen.

The synthesis of the target compound is completed by removing any protecting groups, which are present in the penultimate intermediate using standard techniques, which are well known to those skilled in the art. The deprotected final product is then purified, as necessary, using standard techniques such as silica gel chromatography, HPLC on silica gel, and the like or by recrystallization.

The group $-NR^{8a}R^{9a}$ in the following synthetic paths is $-NR^8R^9$ as defined for formula (I) or a group convertible to $-NR^8R^9$. Conversion of a group $-NR^{8a}R^{9a}$ to a $-NR^8R^9$ group typically arises if a protecting group is needed during the reactions described below. A comprehensive discussion of the ways in which such groups may be protected and methods for cleaving the resulting protected derivatives is given by for example T. W. Greene and P. G. M Wuts in Protective Groups in Organic Synthesis $2^{nd}$ ed., John Wiley & Son, Inc 1991, and by P. J. Kocienski in Protecting Groups, Georg Thieme Verlag 1994. Examples of suitable amino protecting groups include acyl type protecting groups (e.g. formyl, trifluoroacetyl and acetyl), aromatic urethane type protecting groups (e.g. benzyloxycarbonyl (Cbz) and substituted Cbz, and 9-fluorenylmethoxycarbonyl (Fmoc)), aliphatic urethane protecting groups (e.g. t-butyloxycarbonyl (Boc), isopropyloxycarbonyl and cyclohexyloxycarbonyl) and alkyl type protecting groups (e.g. benzyl, trityl and chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate. Hydroxy groups may be protected by reaction of for example acetic anhydride, benzoic anhydride or a trialkylsilyl chloride in an aprotic solvent. Examples of aprotic solvents are dichloromethane, N,N-dimethylformamide, dimethylsulfoxide, tetrahydrofuran and the like.

The compounds of formula (I) wherein $R^1$ is $OC(O)(CH_2)_n NR^8R^9$ and n is an integer from 1 to 8 may be prepared by reaction of the compounds of formula (II) wherein $R^2$ is a hydroxy protecting group with carboxylic acid or a suitable activated derivative of carboxylic acid (III), followed where necessary by subsequent removal of the hydroxyl protecting group $R^2$ and conversion of the —$NR^{8a}R^{9a}$ group to —$NR^8R^9$. Similarly, intermediate compounds related to the compounds of formula (I) wherein $R^1$ is $OC(O)(CH_2)_n NR^8R^9$ and $R^3$ is $CH_3$ may be prepared by the same method.

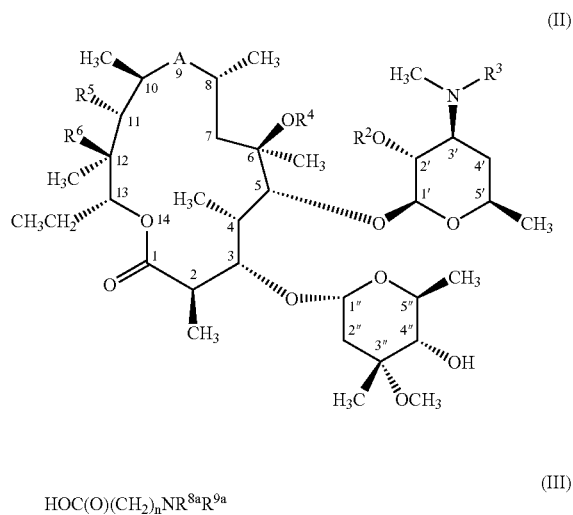

(II)

$HOC(O)(CH_2)_n NR^{8a}R^{9a}$ (III)

Suitable activated derivatives of the carboxylic acid include the corresponding acyl halide, mixed anhydride or activated ester such as a thiol ester.

The reaction is preferably carried out in a suitable aprotic solvent such as a halohydrocarbon (e.g. dichloromethane) or N,N-dimethylformamide optionally in the presence of a tertiary base such as dimethylaminopyridine or triethylamine or in the presence of inorganic base (e.g. sodium hydroxide) and at a temperature within the range of 0° to 120° C. The compounds of formula (II) and (III) may also be reacted in the presence of a carbodiimide such as dicyclohexylcarbodiimide (DCC).

In a further embodiment of the invention, compounds of formula (I) wherein $R^1$ is $OC(O)(CH_2)_n NR^8R^9$ and n is an integer from 1 to 8 may be prepared by reaction of the compounds of formula (IV) wherein n is an integer from 1 to 8 and L is a suitable leaving group, with $NR^{8a}R^{9a}$ (V).

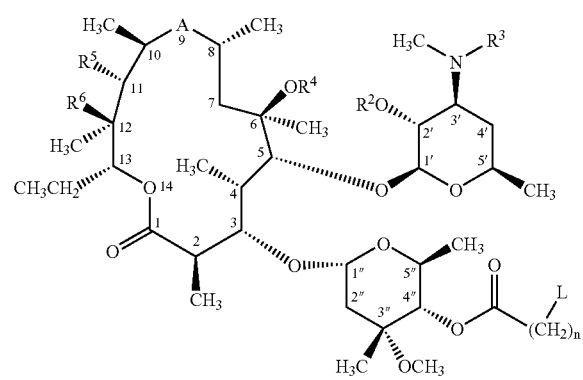

(IV)

The reaction is preferably carried out in a solvent such as a halohydrocarbon (e.g. dichloromethane), an ether (e.g. tetrahydrofuran or dimethoxyethane), acetonitrile or ethyl acetate and the like, dimethylsulfoxide, N,N-dimethylformamide or 1-methyl-pyrrolidone and in the presence of a base, followed, if desired, by removal of the hydroxyl protecting group $R^2$ and conversion of the —$NR^{8a}R^{9a}$ group to —$NR^8R^9$Examples of the bases which may be used include organic bases such as diisopropylethylamine, triethylamine and 1,8-diazabicyclo[5.4.0]undec-7-ene, and inorganic bases such as potassium hydroxide, cesium hydroxide, tetraalkylammonium hydroxide, sodium hydride, potassium hydride and the like. Suitable leaving groups for this reaction include halide (e.g. chloride, bromide or iodide) or a sulfonate group (e.g. tosylate, methanesulfonate, or triflate).

Compounds of formula (IV) may be prepared by reaction of a compound of formula (II), wherein $R^2$ is a hydroxyl protecting group, with carboxylic acid (VI) or a suitable activated derivative of the carboxylic acid $HOC(O)(CH_2)_n L$ (VI), wherein L is a suitable leaving group as defined in the previous paragraph. Suitable activated derivatives of the carboxyl group are those defined above for carboxylic acid (III). The reaction is carried out using the conditions described above for the reaction of a compound of formula (II) with carboxylic acid (III).

In a preferred embodiment of the invention, compounds of formula (I) wherein $R^1$ is $OC(O)(CH_2)_n NR^8R^9$ and n is 2 may be prepared by Michael reaction of the compounds of formula (VII) wherein $R^2$ is a hydroxy protecting group with a compound of formula $NR^{8a}R^{9a}$ (V).

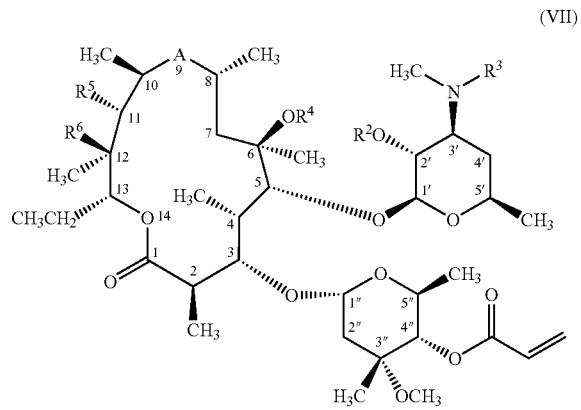

(VII)

The reaction is suitably carried out in a solvent such as dimethylsulfoxide, N,N-dimethylformamide, 1-methyl-pyrrolidone, a halohydrocarbon (e.g. dichloromethane), an ether (e.g. tetrahydrofuran or dimethoxyethane), acetonitrile or alcohol (e.g. methanol or isopropanol) and the like, and in the presence of a base, followed, if desired, by removal of hydroxyl protecting group $R^2$ and conversion of the —$NR^{8a}R^{9a}$ group to —$NR^8R^9$.

Compounds of formula (VII) can be prepared according to the procedure described in international patent application WO 03/042228 incorporated by reference in its entirety, especially pages 16-18. Thus, reaction of the compounds of formula (II) wherein $R^2$ is a hydroxy protecting group with 3-chloropropionyl chloride in the presence of a base such as triethylamine gave compounds of formula (VII).

Compounds of formula (I) wherein $R^1$ is —O—$(CH_2)_n$NR$^8$R$^9$ may be prepared by reaction of a 4"-aldehyde compound of formula (VIII), wherein n is an integer from 1 to 8, with a compound of formula NR$^{8a}$R$^{9a}$ (V), followed where necessary by subsequent removal of the protecting groups and conversion of the NR$^{8a}$R$^{9a}$ to NR$^8$R$^9$.

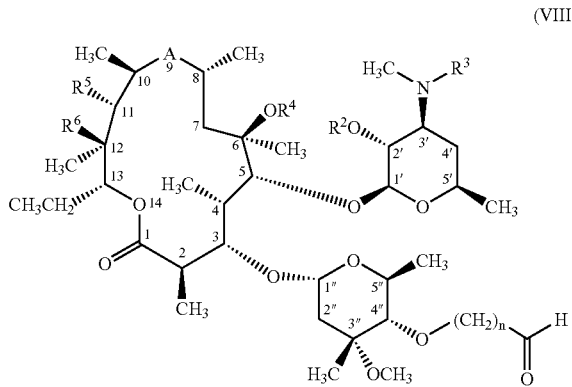
(VIII)

The reductive amination reaction is preferably carried out in a solvent such as methanol and DMF. A suitable reducing agent is, for example, sodium cyanoborohydride.

Compounds of formula (VIII) where n is 1 or 2 may be prepared from suitably protected compounds of formula (IX) by hydroboration with 9-BBN, or other suitable boranes, followed by treatment with peroxide and then oxidation (n=2), or by osmium tetroxide/peridoate cleavage (n=1).

Compounds of formula (IX) can be formed by palladium-catalyzed allylation (Recl. Trav. Chim. Pays-Bas 102, 501-505, 1983) of the 4" the hydroxy compounds of formula (II) that are suitably protected, for example by cyclic protection between the 9 and 11 positions when A is —C(OH)— (J. Antibiot., 42, 293, 1989.).

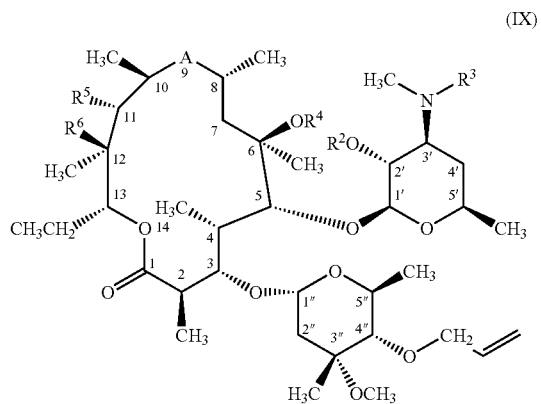
(IX)

In a further embodiment of the invention, compounds of formula (I) wherein $R^1$ is —O—$(CH_2)_n$NR$^8$R$^9$ may be prepared by reaction of compounds of formula (X) with a 3-chloropropionyl chloride...

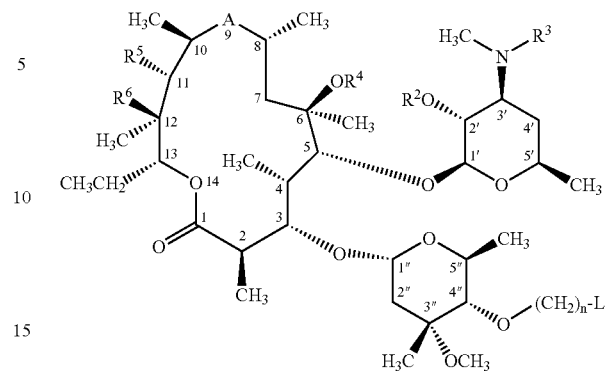
(X)

compound of formula NR$^{8a}$R$^{9a}$ (V), wherein n is an integer from 2 to 8 and L is suitable leaving group. The reaction is preferably carried out in a solvent such as a halohydrocarbon (e.g. dichloromethane), an ether (e.g. tetrahydrofuran or dimethoxyethane), acetonitrile or ethyl acetate and the like, dimethylsulfoxide, N,N-dimethylformamide or 1-methylpyrrolidone and in the presence of a base, followed, if desired, by removal of protecting group $R^2$ and conversion of the NR$^{8a}$R$^{9a}$ group to NR$^8$R$^9$. Examples of the bases which may be used include organic bases such as diisopropylethylamine, triethylamine and 1,8-diazabicyclo[5.4.0]undec-7-ene (DBU), and inorganic bases such as potassium hydroxide, cesium hydroxide, tetraalkylammonium hydroxide, sodium hydride, potassium hydride and the like. Suitable leaving groups for this reaction are halide (e.g. chloride, bromide or iodide).

In a further embodiment of the invention, compounds of formula (I) wherein $R^1$ is —O—$(CH_2)_n$NR$^8$R$^9$, n is 3, $R^8$ and $R^9$ are the same and have the meaning as defined above may be prepared by reductive alkylation of 4"-amine of formula (XI) wherein Z is $CH_2NH_2$ with a compound of formula HC(O)R$^8$ (XII).

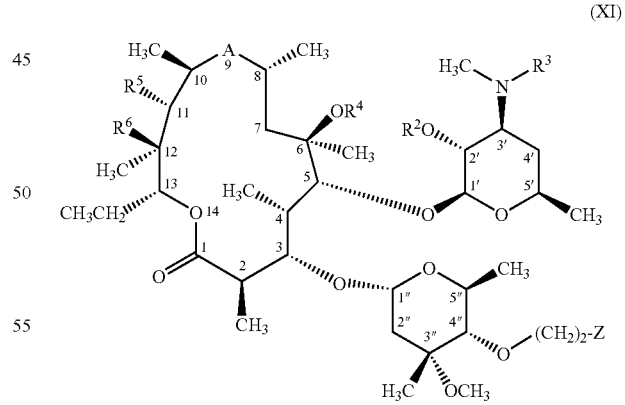
(XI)

Compound of formula (XI) wherein Z is $CH_2NH_2$ may be prepared by reaction of suitable protected compound of formula (II) with acrylonitrile in solvent such as DMSO, THF, t-BuOH in the presence of a base such as NaH giving compound of formula (XI) wherein Z is cyano group, followed by catalytic reduction of cyano group.

Compounds of formula (I) may be prepared by reaction of a suitable activated compound of formula (XIII) wherein $R^2$ is optionally a hydroxy protecting group and $R^{10}$ is an activating group such as imidazolyl or halogen, with a suitable protected derivative of the amine of formula (XIVa) or (XIVb), followed where necessary by subsequent removal of the hydroxyl protecting group $R^2$ and conversion of the $NR^{8a}R^{9a}$ group to $NR^8R^9$.

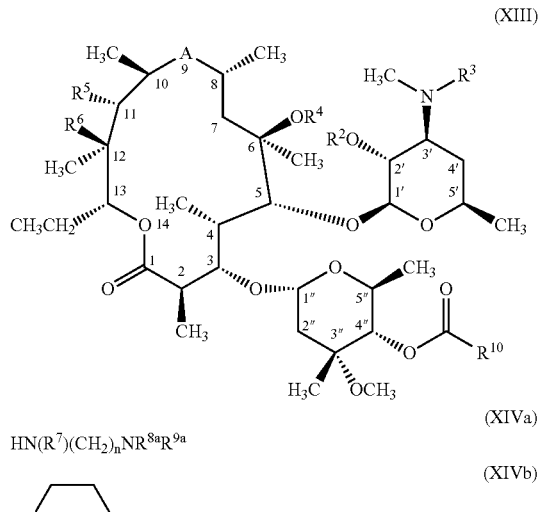

(XIII)

HN($R^7$)(CH$_2$)$_n$NR$^{8a}$R$^{9a}$ (XIVa)

(XIVb)

The reaction is preferably carried out in a suitable aprotic solvent such as N,N-dimethylformamide in the presence of an organic base such as 1,8-diazabiyclo[5.4.0]undec-7-ene (DBU).

Compounds of formula (II) wherein A is —C(=NOR$^7$) and $R^7$ is hydrogen are known compounds or they may be prepared by conventional techniques, for example according to U.S. Pat. No. 3,478,014 or *Journal of Antibiotics*, 44, 313, 1991. Compounds wherein $R^7$ is other than a hydrogen atom may be prepared by alkylation of the oxime, for instance according to EP 1 167 375. All are incorporated by reference.

Compounds of formula (II) wherein A is —CH(OH)— are known compounds or they may be prepared by conventional techniques, for example by treatment of C-9 keto group with reducing agents, for instance hydrides (sodium borohydride or sodium cyanoborohydride (JACS 79, 6062, 1957, *Journal of Antibiotics* 43.1334, 1990, incorporated by reference).

Compounds of formula (II) wherein A is —NHC(O)— or —C(O)NH— and $R^4$ is $C_{1-4}$ alkyl or $C_{2-6}$ alkenyl are known compounds or they may be prepared from corresponding 6-O-alkyl or alkenylerythromycin A oxime by Beckman rearrangement according to the procedure described in WO 9951616, incorporated by reference.

Compounds of formula (II) wherein A is —NR$^7$CH$_2$— or —CH$_2$N(R$^7$)— are known compounds or they may be prepared by analogous methods to those known in the art. Thus, they can be prepared according to the procedures described in U.S. Pat. No. 4,328,334, BE 892357, U.S. Pat. No. 4,464,527, *Bioorg. Med. Chem. Lett.*, 3, 1287, 1993, all incorporated by reference.

Compounds of formula (II) wherein $R^3$ is $C_{2-4}$ alkyl or $C_{1-5}$ alkanoyl are prepared by mono-demethylation of the 3'-NMe$_2$ group with benzylchloroformate, followed by elimination benzyloxycarbonyl groups at position 2' and 3' as described in U.S. Pat. No. 5,250,518. An alternative method for demethylation of the 3'-NMe$_2$ group may be performed by treatment with sodium acetate and iodine in the presence of an organic solvent, as described in U.S. Pat. No. 3,725,385 and WO 2004/013153. The subsequent alkylation or acylation of the secondary amine thus obtained are carried out in accordance with conventional synthetic techniques. All documents cited in this paragraph are incorporated by reference.

Compounds of formula (II) wherein $R^5$ and $R^6$ taken together with the intervening atoms form a cyclic group having the following structure:

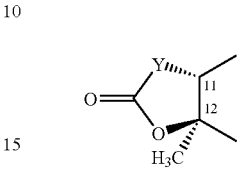

wherein Y is a bivalent radical selected from —CH$_2$—, —CH(CN)—, —O—, —N(R$^7$)— and —CH(SR$^7$)—; may be prepared by analogous methods to those skilled in the art. Thus, they can be prepared according to the procedure described in WO 2004/039822, herein incorporated by reference, and by references cited therein.

A further aspect of the present invention relates to methods for using the compounds of Formula I as anti-inflammatory, and immunomodulating agents which can be administered in different ways, depending on the inflammation site, e.g. percutaneously, orally, buccally, rectally, parenterally or by inhalation when application within the respiratory tract is intended.

The corresponding preparations of the compounds of the present invention can be used in the prophylaxis as well as in the therapeutic treatment (prevention, delay, inhibition or relief) of several disorders (diseases and other pathological inflammatory conditions) caused by or associated with an abnormal or undesirable (excessive, nonregulated, or dysregulated) inflammatory immune response involving the production of inflammatory cytokines or other inflammation mediators, including without limitation TNF-α, IL-1, IL-2, IL-5, IL6, and IL-8.

These disorders include autoimmune diseases such as rheumatoid arthritis, insulin-dependent diabetes mellitus, autoimmune thyroiditis, multiple sclerosis, uveoretinitis, lupus erythematosus, scleroderma; psoriasis, acne; other arthritic conditions having an inflammatory component such as rheumatoid spondylitis, osteoarthritis, osteomyelitis; septic arthritis and polyarthritis; other inflammatory brain disorders, such as meningitis, Alzheimer's disease, AIDS dementia encephalitis, other inflammatory eye inflammations, such as retinitis; inflammatory skin disorders, such as, eczema, other dermatites (e.g., atopic, contact), psoriasis, burns induced by UV radiation (sun rays and similar TV sources); inflammatory bowel disease, such as Crohn's disease, ulcerative colitis; COPD; cystic fibrosis; bronchiectasis; asthma; other allergy disorders, such as allergic rhinitis; chronic sinusitis; conditions associated with acute trauma such as cerebral injury following stroke, heart tissue injury due to myocardial ischemia, lung injury such as that which occurs in adult respiratory distress syndrome; inflammation accompanying infection, such as sepsis, septic shock, toxic shock syndrome, other inflammatory conditions associated with particular organs or tissues, such as nephritis (e.g., glomerulonephritis), inflamed appendix, gout, inflamed gall bladder, congestive heart failure, Type II diabetes, lung fibrosis, bronchiolitis obliterans; diffuse panbronchiolitis; vascular disease, such as atherosclerosis and restenosis; and alloimmunity leading to transplant rejection. The compounds can also be administered by inhalation when application within the respiratory tract is intended. A further object of the present invention relates to the preparation of various pharmaceutical forms of the compounds to achieve the optimal bioavailability of the active compound of Formula I.

Pharmaceutical Compositions

Further, the present invention relates to pharmaceutical compositions containing an effective dose of compounds of the present invention as well as pharmaceutically acceptable excipients, such as carriers or diluents.

While it is possible that, for use in the methods of the invention, a compound of formula I may be administered as the bulk substance, it is preferable to present the active ingredient in a pharmaceutical formulation, e.g., wherein the agent is in admixture with a pharmaceutically acceptable carrier selected with regard to the intended route of administration and standard pharmaceutical practice.

The corresponding preparations of the compounds of the present invention can be used in the prophylaxis (including without limitation the prevention, delay or inhibition of recurrence of one or more of the clinical or subclinical symptoms discussed and defined in connection with the definitions of "treatment" above, as well as in the therapeutic treatment of several diseases and pathological inflammatory conditions including: chronic obstructive pulmonary disorder (COPD), asthma, inflammatory nasal diseases such as allergic rhinitis, nasal polyps, intestinal diseases such as Crohn's disease, colitis, intestinal inflammation, ulcerative colitis, dermatological inflammations such as eczema, psoriasis, allergic dermatitis, neurodermatitis, pruritis, conjunctivitis and rheumatoid arthritis.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients.

There may be different composition/formulation requirements depending on the different delivery systems. It is to be understood that not all of the compounds need to be administered by the same route. Likewise, if the composition comprises more than one active component, then those components may be administered by the same or different routes. By way of example, the pharmaceutical composition of the present invention may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

The present invention further relates to pharmaceutical formulations containing a therapeutically effective quantity of a compound of formula I or one of its salts mixed with a pharmaceutically acceptable vehicle. The pharmaceutical formulations of the present invention can be liquids that are suitable for oral, mucosal and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

The compounds of the invention can be administered for immediate-, delayed-, modified-, sustained-, pulsed- or controlled-release applications.

The compound can also be incorporated into a formulation for treating inflammation localized in an organ or tissue, e.g., Crohn's disease, where it can be administered orally or rectally. Formulations for oral administration can incorporate excipients enabling bioavailability of the compound at the site of inflammation. This can be achieved by different combinations of enteric and delayed release formulations. The compound of Formula I can also be used in the treatment of Crohn's disease and intestinal inflammation disease if the compound is applied in the form of a clyster, for which a suitable formulation can be used, as is well known in the field.

In some embodiments, the oral compositions are slow, delayed or positioned release (e.g., enteric especially colonic release) tablets or capsules. This release profile can be achieved without limitation by use of a coating resistant to conditions within the stomach but releasing the contents in the colon or other portion of the GI tract wherein a lesion or inflammation site has been identified. Or a delayed release can be achieved by a coating that is simply slow to disintegrate. Or the two (delayed and positioned release) profiles can be combined in a single formulation by choice of one or more appropriate coatings and other excipients. Such formulations constitute a further feature of the present invention.

Formulations for oral administration can be so designed to enable bioavailability of the compound at the site of inflammation in the intestines. This can be achieved by different combinations of delayed release formulations. The compound of Formula I can also be used in the treatment of Crohn's disease and intestinal inflammation disease if the compound is applied in the form of an enema, for which a suitable formulation can be used.

Suitable compositions for delayed or positioned release and/or enteric coated oral formulations include tablet formulations film coated with materials that are water resistant, pH sensitive, digested or emulsified by intestinal juices or sloughed off at a slow but regular rate when moistened. Suitable coating materials include, but are not limited to, hydroxypropyl methylcellulose, ethyl cellulose, cellulose acetate phthalate, polyvinyl acetate phthalate, hydroxypropyl methylcellulose phthalate, polymers of metacrylic acid and its esters, and combinations thereof. Plasticizers such as, but not limited to polyethylene glycol, dibutylphthalate, triacetin and castor oil may be used. A pigment may also be used to color the film. Suppositories are be prepared by using carriers like cocoa butter, suppository bases such as Suppocire C, and Suppocire NA50 (supplied by Gattefosse Deutschland GmbH, D-Weil am Rhein, Germany) and other Suppocire type excipients obtained by interesterification of hydrogenated palm oil and palm kernel oil (C8-C18 triglycerides), esterification of glycerol and specific fatty acids, or polyglycosylated glycerides, and whitepsol (hydrogenated plant oils derivatives with additives). Enemas are formulated by using the appropriate active compound according to the present invention and solvents or excipients for suspensions. Suspensions are produced by using micronized compounds, and appropriate vehicle containing suspension stabilizing agents, thickeners and emulsifiers like carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrolidone, N-vinylacetamide polymer, polyvinyl methacrylate, polyethylene glycol, pluronic, gelatin, methyl vinyl ether-maleic anhydride copolymer, soluble starch, pullulan and a copolymer of methyl acrylate and 2-ethylhexyl acrylate lecithin, lecithin derivatives, propylene glycol fatty acid esters, glycerin fatty acid esters, sorbitan fatty acid esters, polyoxyethylene sorbitan fatty acid esters, polyethylene glycol fatty acid esters, polyoxyethylene hydrated caster oil, polyoxyethylene alkyl ethers, and pluronic and appropriate buffer system in pH range of 6.5 to 8. The use of preservatives, masking agents is suitable. The average diameter of micronized particles can be between 1 and 20 micrometers, or can be less than 1 micrometer. Compounds can also be incorporated in the formulation by using their water-soluble salt forms.

Alternatively, materials may be incorporated into the matrix of the tablet e.g. hydroxypropyl methylcellulose, ethyl cellulose or polymers of acrylic and metacrylic acid esters. These latter materials may also be applied to tablets by compression coating.

Pharmaceutical compositions can be prepared by mixing a therapeutically effective amount of the active substance with a pharmaceutically acceptable carrier that can have different forms, depending on the way of administration. Pharmaceutical compositions can be prepared by using conventional pharmaceutical excipients and methods of preparation. The forms for oral administration can be capsules, powders or tablets where usual solid vehicles including lactose, starch, glucose, methylcellulose, magnesium stearate, di-calcium phosphate, mannitol may be added, as well as usual liquid oral excipients including, but not limited to, ethanol, glycerol, and water. All excipients may be mixed with disintegrating agents, solvents, granulating agents, moisturizers and binders. When a solid carrier is used for preparation of oral compositions (e.g., starch, sugar, kaolin, binders disintegrating agents) preparation can be in the form of powder, capsules containing granules or coated particles, tablets, hard gelatin capsules, or granules without limitation, and the amount of the solid carrier can vary (between 1 mg to 1 g). Tablets and capsules are the preferred oral composition forms.

Pharmaceutical compositions containing compounds of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Examples of pharmaceutically acceptable disintegrants for oral compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable odorants for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetriacetic acid (EDTA), thiourea, tocopherol and butyl hydroxyanisole.

The compounds of the invention may also, for example, be formulated as suppositories e.g., containing conventional suppository bases for use in human or veterinary medicine or as pessaries e.g., containing conventional pessary bases.

For percutaneous or mucosal external administration, the compound of Formula I can be prepared in a form of an ointment or cream, gel or lotion. Ointments, creams and gels can be formulated using a water or oil base with addition of an appropriate emulsifier or gelling agent Formulation of the present compounds is especially significant for respiratory inhalation, wherein the compound of Formula I is to be delivered in the form of an aerosol under pressure. It is preferred to micronize the compound of Formula I after it has been homogenised, e.g., in lactose, glucose, higher fatty acids, sodium salt of dioctylsulfosuccinic acid or, most preferably, in carboxymethyl cellulose, in order to achieve a microparticle size of 5 µm or less for the majority of particles. For the inhalation formulation, the aerosol can be mixed with a gas or a liquid propellant for dispensing the active substance. An inhaler or atomizer or nebulizer may be used. Such devices are known. See, e.g., Newman et al., *Thorax*, 1985, 40:61-676 Berenberg, M., *J. Asthma USA*, 1985, 22:87-92. A Bird nebulizer can also be used. See also U.S. Pat. Nos. 6,402,733; 6,273,086; and 6,228,346.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colorants, and odorants.

Examples of pharmaceutically acceptable polymers suitable for such topical compositions include, but are not limited to, acrylic polymers; cellulose derivatives, such as carboxymethylcellulose sodium, methylcellulose or hydroxypropylcellulose; natural polymers, such as alginates, tragacanth, pectin, xanthan and cytosan.

As indicated, the compound of the present invention can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT"") or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material.

A therapeutically effective amount of the compound of the present invention can be determined by methods known in the art. Since the compound of the present invention is more efficiently delivered to the desired site than other compounds such as azithromycin and clarithromycin, a lesser amount of the compound of the present invention can be delivered (on a molar basis) compared to the azithromycin or clarithromycin while still achieving the same therapeutic effect. Thus, the table below serves only as a guide. Broad and preferred effective amounts of the compound, a pharmaceutically acceptable derivative thereof are shown in the table below.

|  | Amount of Compound of Formula (I), or Pharmaceutically Acceptable Derivative Thereof (µmol/kg body weight/day) |
| --- | --- |
| Broad Range | from about 0.004 to about 4000 |
| Narrower | from about 0.04 to about 400 |
| Still Narrower | from about 4 to about 400 |
| Narrowest | from about 12 to about 120 |

The efficacy of the present compounds can be assessed by any method for assessing inflammation or anti-inflammatory effect. There are many known methods for this purpose including without limitation use of contrast ultrasound in conjunction with injection of microbubbles, measurement of inflammatory cytokines (such as TNF-α, IL-1, IFN-γ) measurement of activated immune system cells (activated T cells, cytotoxic T cells specifically recognizing the inflamed or transplanted tissue) as well as by observation (reduction of oedema, reduction of erythema, reduction of pruritus or burning sensation, reduction of body temperature, improvement in function of the afflicted organ) as well as any of the methods provided below.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

Biological Assays

The therapeutic effect of compounds of the present invention was determined in in vitro and in vivo experiments such as the following.

The cytokines assayed in the biological examples, when expressed at elevated amounts, are markers for inflammation and, in the case of cell proliferation, granulocyte degranulation and lung neutrophilia, the behaviors of these immune cells are also markers for their activation and, therefore, inflammation. Consequently, reduction of pro-inflammatory cytokine expression or secretion and reduction in cell proliferation, degranulation or neutrophil accumulation is a measure of a compound's anti-inflammatory activity. Lung neutrophilia specifically serves as a model for COPD.

A compound analyzed using the biological assays as defined herein is considered to be "active" if it is better than a positive control (i.e., azithromycin) in at least one inhibitory function (i.e., inhibition of TNF-α or IL-6) after stimulation with al least one stimulant (e.g., PMA or PHA). More preferably, an active compound exhibits more than 50% inhibition in at least one inhibitory function Sample Preparation Test substances used in in vitro experiments were dissolved in dimethyl sulfoxide (DMSO) (Kemika, Croatia) at concentrations of 50 mM and 10 mM, and were further diluted to final concentrations of 50 μM and 10 μM in 1 mL Dulbecco's modified Eagle medium (DMEM) supplemented with 1% heat inactivated fetal bovine serum (FBS), 1% L-glutamine, 50 U/ml penicillin, 50 μg/ml streptomycin and 2.5 μg/mL Fungizone (amphotericin B). Media and all media supplements were purchased from Gibco, Australia, except the FBS was purchased from Sigma, USA.

Isolation of Peripheral Blood Leukocytes

Peripheral blood leukocytes (PBL) were obtained from venous blood of healthy volunteers by sedimentation on 2% dextran T-500 (Amersham Biosciences, USA) and subsequent centrifugations of leukocyte rich plasma.

Inhibition of Proinflammatory Cytokine Production by Stimulated Human Peripheral Blood Leukocytes In Vitro Peripheral blood leukocytes (PBL), isolated as described above, were seeded in a 48-well plate at a concentration of 3 to $5 \times 10^6$ cell per well in culture medium consisting of RPMI 1640 medium (Institute of Immunology, Croatia) supplemented with 10% heat-inactivated fetal calf serum (FCS, Biowhittaker, USA), 100 U/ml penicillin (Gibco, Australia), 100 μg/ml streptomycin (Gibco, Australia) and 2 mM L-glutamine (Gibco, Australia), and preincubated with the test compounds for 2 h at 37° C., in an atmosphere of 5% $CO_2$, and 90% humidity. Then, stimuli (Sigma, USA) were added to a final concentration of 2 μg/mL lipopolysaccharide (LPS), 1 μg/mL phorbol 12-myristate 13-acetate (PMA) or 120 μg/mL zymosan. Samples were incubated overnight under conditions described above. At the end of incubation, the supernatants were transferred to eppendorf tubes and centrifuged for 10 min at 1500×g. Concentrations of human TNF-α, IL-1β, IL-6 and IL-8 were determined in cell supernatants by sandwich ELISA, using capture and detection antibodies (R&D Systems, Minneapolis, Minn.) according to the manufacturer's recommendations.

Inhibition (as percentage) was calculated using the following formula:

% inhibition=(1−concentration of cytokines in sample/concentration of cytokines in positive control)×100.

The positive control refers to LPS-, PMA- or zymosan-stimulated samples that were not preincubated with test compounds.

TABLE 1

Percentage of inhibition of proinflammatory cytokine production by stimulated PBL treated with compounds

| Example | conc. (μM) | TNF-α | | | IL-1α | | | IL-6 | | | IL-8 | | |
| --- | --- | --- | --- | --- | --- | --- | --- | --- | --- | --- | --- | --- | --- |
| | | PMA | LPS | zymosan | PMA | LPS | zymosan | PMA | LPS | zymosan | PMA | LPS | zymosan |
| azithromycin | 10 | 0 | 36 | 6 | 0 | 28 | 20 | 0 | 15 | 20 | 0 | 0 | 0 |
| | 50 | 0 | 20 | 64 | 0 | 48 | 75 | 0 | 40 | 75 | 0 | 0 | 0 |
| clarithromycin | 10 | 0 | 0 | 0 | 26 | 0 | 36 | 0 | 11 | 28 | 33 | 23 | 0 |
| | 50 | 0 | 0 | 0 | 33 | 0 | 59 | 0 | 0 | 0 | 0 | 0 | 0 |
| 1 | 10 | 0 | 54 | 88 | 0 | 67 | 73 | 0 | 10 | 29 | 0 | 0 | 29 |
| | 50 | 94 | 100 | 100 | 84 | 93 | 83 | 96 | 94 | 100 | 100 | 97 | 100 |
| 3 | 10 | 91 | 72 | 76 | 73 | 87 | 88 | 60 | 56 | 44 | 30 | 48 | 32 |
| | 50 | 83 | 81 | 96 | 68 | 86 | 91 | 66 | 78 | 74 | 22 | 71 | 16 |
| 8 | 10 | 46 | 51 | 87 | 71 | 66 | 86 | 24 | 16 | 57 | 40 | 38 | 31 |
| | 50 | 87 | 85 | 92 | 86 | 83 | 94 | 100 | 63 | 80 | 89 | 79 | 88 |
| 9 | 10 | 93 | 73 | 14 | 69 | 72 | 82 | 30 | 22 | 0 | 0 | 18 | 0 |
| | 50 | 85 | 96 | 72 | 72 | 82 | 0 | 95 | 100 | 100 | 94 | 96 | 91 |
| 10 | 10 | 41 | 49 | 14 | 30 | 44 | 48 | 12 | 14 | 19 | 0 | 27 | 28 |
| | 50 | 62 | 86 | 72 | 0 | 41 | 49 | 18 | 71 | 39 | 42 | 52 | 36 |
| 12 | 10 | 49 | 23 | 77 | 45 | 43 | 88 | 32 | 16 | 67 | 0 | 7 | 2 |
| | 50 | 97 | 92 | 97 | 90 | 95 | 100 | 67 | 81 | 91 | 3 | 72 | 9 |
| 15 | 10 | 82 | 61 | 93 | 80 | 80 | 96 | 50 | 39 | 76 | 0 | 38 | 42 |
| | 50 | 96 | 99 | 100 | 96 | 98 | 99 | 95 | 93 | 96 | 95 | 94 | 91 |
| 17 | 10 | 46 | 13 | 30 | 55 | 25 | 58 | 37 | 9 | 33 | 21 | 4 | 20 |
| | 50 | 67 | 21 | 46 | 75 | 44 | 90 | 55 | 14 | 60 | 13 | 6 | 13 |
| 18 | 10 | 38 | 9 | 21 | 34 | 16 | 51 | 33 | 10 | 34 | 7 | 6 | 25 |
| | 50 | 57 | 12 | 30 | 68 | 45 | 90 | 61 | 23 | 63 | 0 | 0 | 22 |
| 21 | 10 | 8 | 0 | 5 | 31 | 14 | 58 | 17 | 1 | 22 | 6 | 0 | 0 |
| | 50 | 75 | 10 | 39 | 69 | 54 | 86 | 63 | 22 | 50 | 23 | 4 | 13 |
| 22 | 10 | 0 | 0 | 0 | 14 | 5 | 57 | 16 | 3 | 28 | 0 | 0 | 10 |
| | 50 | 55 | 23 | 35 | 56 | 46 | 76 | 60 | 28 | 51 | 15 | 5 | 30 |
| 23 | 10 | 5 | 0 | 0 | 12 | 2 | 67 | 20 | 0 | 35 | 0 | 0 | 22 |
| | 50 | 54 | 19 | 37 | 69 | 39 | 75 | 59 | 14 | 45 | 15 | 10 | 43 |
| 25 | 10 | 41 | 0 | 19 | 58 | 22 | 82 | 51 | 4 | 51 | 0 | 0 | 17 |
| | 50 | 91 | 71 | 88 | 86 | 61 | 93 | 87 | 62 | 86 | 34 | 45 | 63 |
| 33 | 10 | 23 | 16 | 16 | 33 | 28 | 55 | 9 | 8 | 13 | 0 | 0 | 0 |
| | 50 | 74 | 50 | 53 | 75 | 42 | 85 | 49 | 30 | 40 | 10 | 11 | 40 |
| 34 | 10 | 86 | 55 | 65 | 86 | 69 | 77 | 66 | 28 | 66 | 33 | 21 | 32 |
| | 50 | 100 | 96 | 100 | 100 | 82 | 99 | 95 | 91 | 99 | 76 | 87 | 81 |

TABLE 1-continued

Percentage of inhibition of proinflammatory cytokine production by stimulated PBL treated with compounds

| Example | conc. (μM) | TNF-α PMA | LPS | zymosan | IL-1α PMA | LPS | zymosan | IL-6 PMA | LPS | zymosan | IL-8 PMA | LPS | zymosan |
|---|---|---|---|---|---|---|---|---|---|---|---|---|---|
| 37 | 10 | 28 | 15 | 17 | 14 | 60 | 49 | 41 | 20 | 21 | 17 | 14 | 27 |
|  | 50 | 45 | 76 | 96 | 25 | 69 | 98 | 57 | 78 | 100 | 10 | 0 | 0 |
| 40 | 10 | 55 | 67 | 60 | 0 | 0 | 1 | 0 | 7 | 0 | 31 | 24 | 6 |
|  | 50 | 77 | 82 | 76 | 0 | 28 | 55 | 0 | 0 | 0 | 12 | 0 | 0 |
| 41 | 10 | 30 | 39 | 27 | 52 | 79 | 80 | 59 | 25 | 36 | 10 | 29 | 19 |
|  | 50 | 70 | 95 | 99 | 100 | 84 | 100 | 79 | 92 | 100 | 42 | 87 | 63 |
| 48 | 10 | 31 | 49 | 82 | 38 | 64 | 85 | 30 | 57 | 73 | 25 | 36 | 49 |
|  | 50 | 90 | 87 | 97 | 78 | 79 | 92 | 84 | 97 | 97 | 83 | 85 | 90 |
| 49 | 10 | 37 | 69 | 70 | 35 | 84 | 76 | 76 | 70 | 76 | 0 | 44 | 15 |
|  | 50 | 86 | 91 | 93 | 84 | 86 | 25 | 86 | 99 | 97 | 95 | 86 | 54 |
| 50 | 10 | 0 | 10 | 36 | 0 | 19 | 81 | 0 | 0 | 52 | 0 | 0 | 0 |
|  | 50 | 100 | 100 | 98 | 44 | 23 | 69 | 23 | 54 | 96 | 100 | 61 | 70 |
| 51C | 10 | 18 | 5 | 38 | 0 | 2 | 62 | 27 | 4 | 42 | 12 | 0 | 26 |
|  | 50 | 4 | 0 | 0 | 0 | 0 | 0 | 6 | 0 | 0 | 0 | 0 | 0 |
| 53 | 10 | 82 | 28 | 64 | 92 | 83 | 92 | 66 | 20 | 68 | 30 | 9 | 19 |
|  | 50 | 100 | 100 | 100 | 99 | 95 | 100 | 95 | 99 | 100 | 63 | 100 | 92 |
| 54 | 10 | 25 | 3 | 11 | 62 | 60 | 56 | 0 | 0 | 9 | 0 | 0 | 0 |
|  | 50 | 96 | 55 | 92 | 97 | 69 | 98 | 71 | 58 | 87 | 40 | 82 | 53 |
| 58 | 10 | 58 | 39 | 61 | 66 | 72 | 86 | 42 | 29 | 56 | 29 | 21 | 21 |
|  | 50 | 97 | 95 | 100 | 52 | 90 | 99 | 89 | 93 | 100 | 82 | 86 | 95 |
| 59 | 10 | 98 | 70 | 91 | 82 | 94 | 99 | 75 | 61 | 80 | 72 | 42 | 54 |
|  | 50 | 98 | 99 | 100 | 45 | 82 | 91 | 90 | 98 | 100 | 74 | 81 | 96 |
| 60 | 10 | 88 | 55 | 87 | 88 | 86 | 94 | 59 | 46 | 68 | 67 | 42 | 39 |
|  | 50 | 99 | 99 | 100 | 65 | 91 | 97 | 92 | 97 | 100 | 83 | 83 | 97 |
| 63 | 10 | 21 | 0 | 0 | 52 | 59 | 45 | 24 | 8 | 0 | 0 | 0 | 0 |
|  | 50 | 73 | 69 | 87 | 81 | 89 | 100 | 62 | 60 | 90 | 3 | 36 | 44 |
| 90 | 10 | 40 | 78 | 53 | 61 | 62 | 82 | 46 | 67 | 60 | 0 | 4 | 24 |
|  | 50 | 95 | 100 | 94 | 57 | 91 | 100 | 90 | 88 | 100 | 53 | 38 | 88 |
| 95 | 10 | 34 | 12 | 47 | 25 | 0 | 38 | 17 | 1 | 18 | 0 | 0 | 5 |
|  | 50 | 50 | 30 | 63 | 75 | 0 | 42 | 56 | 8 | 58 | 21 | 16 | 33 |
| 96 | 10 | 14 | 3 | 21 | 32 | 0 | 36 | 27 | 0 | 17 | 0 | 0 | 6 |
|  | 50 | 48 | 13 | 61 | 81 | 0 | 88 | 64 | 3 | 76 | 12 | 17 | 40 |
| 97 | 10 | 31 | 0 | 43 | 57 | 0 | 49 | 32 | 0 | 9 | 4 | 0 | 10 |
|  | 50 | 57 | 62 | 69 | 79 | 0 | 34 | 51 | 14 | 56 | 29 | 23 | 34 |

Isolation of Peripheral Blood Mononuclear Cells

Heparinized peripheral blood was obtained from healthy donors, and peripheral blood mononuclear cells (PBMC) were isolated by Histopaque 1077 (Sigma, USA) density centrifugation at 400×g for 30 minutes. Collected PBMC were centrifuged in plasma at 400×g for 10 min, resuspended and washed in RPMI 1640 (Institute of Immunology, Croatia) by centrifugation.

Inhibition of Production of T-Cell Specific Cytokines, IL-2 and IL-5" by Stimulated Human Peripheral Blood Mononuclear Cells In Vitro Peripheral blood mononuclear cells (PBMC), isolated as described above, were seeded in a 48-well plate at a concentration of $1 \times 10^6$ cells per well in the RPMI culture medium described above. Cells were stimulated with 10 μg/mL phytohaemagglutinin (PHA) (Sigma, USA) and incubated at 37° C., 5% $CO_2$ in 90% humidity with tested compounds (10 and 50 μM) for 3 days. Cytokine concentrations were determined in supernatants by sandwich ELISA, using capture and detection antibodies (R&D, USA) according to the manufacturer's recommendations.

Inhibition (as percentage) was calculated using the following formula:

% inhibition=(1−concentration of cytokines in sample/concentration of cytokines in positive control)×100.

The positive control refers to LPS-, PMA- or zymosan-stimulated samples that were not treated with test compounds.

TABLE 2

Percentage of inhibition of IL-2 and IL-5 production by stimulated PBMC treated with test compounds

|  |  | IL-2 | IL-5 |
|---|---|---|---|
| clarithromycin | 10 μM | 0 | 13 |
|  | 50 μM | 3 | 47 |
| Example 8 | 10 μM | 100 | 34 |
|  | 50 μM | 100 | 85 |
| Example 49 | 10 μM | 51 | 59 |
|  | 50 μM | 100 | 81 |

Effects on Human T-Cell Proliferation In Vitro

The influence of the various test compounds at two different concentrations (50 μM and 10 μM) on cell proliferation of human peripheral blood mononuclear cells (PBMC) was assessed.

Heparinized peripheral blood was obtained from healthy donors, and PBMC were isolated by Histopaque 1077 (Sigma, USA) density centrifugation at 400×g for 30 minutes. $5 \times 10^4$ cells/well were cultured for 3 days in the RPMI medium as described above in the presence (positive control) or absence (negative control) of stimulators [PHA (2.5 μg/mL) (Sigma, USA), or both PMA (10 ng/mL) (Sigma, USA) and ionomycin (500 ng/mL) (Calbiochem, USA)], and in the presence of the test compounds, at 37° C. in an atmosphere of 5% $CO_2$ and 90% humidity. The cells were pulsed with 1 μCi of $^3$H-thymidine (Amersham, USA) per well during the last 18 h of the culture, and were harvested on the 96-well filter (Packard Bioscience, USA) using a multiple cell harvester (Packard, USA). The incorporation of $^3$H-thymidine in activated cells were measured using TopCount NXT (Packard, USA).

Inhibition (as percentage) was calculated using the following formula:

% inhibition=(1−($^3$H)thymidine incorporation expressed in counts per minute (cpm) in sample/ ($^3$H)thymidine incorporation expressed in cpm in positive control)×100

The positive control refers to LPS-, PMA- or zymosan-stimulated samples that were not treated with test compounds.

TABLE 3

Percentage of inhibition of proliferation of stimulated PBMC cell line treated with test compounds

| Example | PHA | | PMA + iono. | |
|---|---|---|---|---|
| | 50 μM | 10 μM | 50 μM | 10 μM |
| azithromycin | 29 | 5 | 31 | 9 |
| clarithromycin | 7 | 0 | 14 | 9 |
| 1 | 99 | 95 | 96 | 90 |
| 2 | 41 | 35 | 31 | 1 |
| 3 | 75 | 2 | 81 | 17 |
| 8 | 100 | 96 | 99 | 37 |
| 9 | 100 | 91 | 100 | 17 |
| 10 | 98 | 71 | 100 | 3 |
| 12 | 99 | 33 | 96 | 29 |
| 14 | 99 | 23 | 91 | 24 |
| 15 | 99 | 68 | 98 | 53 |
| 17 | 70 | 0 | 49 | 3 |
| 21 | 80 | 0 | 74 | 0 |
| 31 | 99 | 23 | 91 | 24 |
| 34 | 99 | 66 | 87 | 0 |
| 48 | 100 | 93 | 100 | 81 |
| 49 | 99 | 44 | 100 | 24 |

Isolation of Granulocytes

Granulocytes were obtained from heparinized whole blood using density gradiant centrifugation. Erythrocytes were sedimented on 3% dextran T-500 (Amersham Pharmacia Biotech AB, Uppsala, Sweden). Leukocytes were centrifuged on Ficoll (Amersham Pharmacia Biotech AB, Uppsala, Sweden) for 35 min at 600 g at 20° C. The pellet of granulocytes was cleared from remaining erythrocytes by a brief hypotonic lysis.

Inhibition of Degranulation of Granulocytes

1×10$^6$ granulocytes, isolated as described above, were resuspended in RPMI-1640 medium (Institute of Immunology, Croatia), and were incubated with 10 or 50 μM of test compound together with cytochalasine B (5 μg/mL) for 2 h at 37° C. Degranulation then was induced by the addition of 0.1 μM fMLP (Sigma, USA) or 0.5 μM A23187 (Calbiochem, USA). The activity of free neutrophil elastase was determined with a chromogenic substrate specific for human neutrophil elastase, such as N-(methoxysuccinyl)-L-alanyl-L-alanyl-L-prolyl-L-valine 4-nitroanilide (Sigma Chemical Company, St Louis, Mo., USA). Elastase activity, as a marker of primary granules, was assessed in supernatant using a spectrophotometer at an absorbance of 405 nm.

Results are expressed as the percent of inhibition of degranulation in unstimulated cells, and in stimulated cells treated with fMLP or A23187.

TABLE 4

Percentage of inhibition of degranulation of granulocytes stimulated with fMLP or A23187

| | | fMLP 0.1 μM | A23187 0.5 μM |
|---|---|---|---|
| azithromycin | 50 μM | 36 | 15 |
| erythromycin | 50 μM | 23 | 0 |
| Example 8 | 10 μM | 52 | 10 |
| | 50 μM | 72 | 24 |
| Example 49 | 10 μM | 47 | 10 |
| | 50 μM | 72 | 51 |

Accumulation in Granulocytes 7.5×10$^6$ granulocytes, isolated as described above, were suspended in 3 mL of RPMI 1640 (Institute of Immunology, Croatia) containing 10 μM of tested macrolide. Samples were incubated at 37° C. for 180 min. Following incubation, the samples were centrifuged through the layer of Poly(dimethylsiloxane-co-diphenylsiloxane), dihydroxy terminated-silicone oil (Aldrich Chemical Company, Milwaukee, USA). The pellet was resuspended in 0.5% Triton X-100 (Sigma, St. Louis, USA) in deionized water (MilliQ, Millipore Corporation, Bedford, USA). The suspension was sonicated, proteins were precipitated with acetonitrile, and the concentration of macrolide in the supernatants was determined by liquid chromatography-mass spectrometry (LC-MS).

Intracellular concentrations of the test compounds were calculated from the mean cell number recovered after centrifuging through silicone oil. According to the literature, about 1 million neutrophils is considered to have a volume of 0.24 μL (Vazifeh et al., Antimicrob Agents Chemo. 1997; 41: 2099-2107). To estimate the extent of macrolide accumulation, the intracellular to extracellular concentration ratio (I/E) was calculated, where E (due to a large volume of incubation medium) was taken as constant (10 μM). Results are expressed relative to azithromycin according to the following equation: % of azithromycin uptake =(I/E of a substance/I/E of azithromycin)×100. I/E values obtained for azithromycin were 164±10.

TABLE 5

Accumulation of test compounds in granulocytes expressed relative to azithromycin uptake

| Example | Uptake (% azithromycin) |
|---|---|
| azithromycin | 100 |
| 3 | 15 |
| 8 | 42 |
| 9 | 412 |
| 48 | 125 |
| 49 | >600 |
| 51C | 122 |

Cytotoxicity Assay Hep G2 and A549 Cell Lines

To determine whether the anti-inflammatory activity of the test compounds was due to observed inhibition of cytokine production and inhibition of proliferation in vitro, and was not a consequence of cellular cytotoxicity, measurement of succinate dehydrogenase activity in living cells was performed. Cells were cultured for 24 h in RPM medium as described above at 37° C. the presence of the test compounds at concentrations of 50 μM and 12.5 μM. MTT [3-(4,5-dimethylthiazole-2-yl)-2,5-diphenyl tetrazolium bromide] (Promega, USA), a detection reagent, was then added and the cultures were incubated for 0.5-2 h. The amount of MTT-Formazan produced was determined using a spectrophotometer at 490 nm (Mosmann, J. Immunol. Methods, 1983, 65: 55-63).

The percentage of inhibition of cell growth was calculated using the following formula:

$$\% \text{ inhibition of cell growth} = OD_{490} \text{ treated cells} / OD_{490} \text{ nontreated cells} \times 100.$$

TABLE 6

Percentage of inhibition of cell growth after treatment with substances

| Example | conc. (µM) | Hep G2 | A549 |
|---|---|---|---|
| azithromycin | 12.5 | 0 | 0 |
|  | 50 | 0 | 0 |
| clarithromycin | 12.5 | 0 | 0 |
|  | 50 | 0 | 0 |
| 1 | 12.5 | 0 | 0 |
|  | 50 | 15 | 3 |
| 2 | 12.5 | 0 | 0 |
|  | 50 | 1 | 3 |
| 3 | 12.5 | 0 | 0 |
|  | 50 | 0 | 0 |
| 8 | 12.5 | 3 | 0 |
|  | 50 | 5 | 3 |
| 9 | 12.5 | 4 | 0 |
|  | 50 | 15 | 0 |
| 10 | 12.5 | 0 | 12 |
|  | 50 | 5 | 6 |
| 12 | 12.5 | 0 | 8 |
|  | 50 | 0 | 4 |
| 14 | 12.5 | 0 | 4 |
|  | 50 | 0 | 0 |
| 15 | 12.5 | 3 | 0 |
|  | 50 | 0 | 5 |
| 17 | 12.5 | 5 | 5 |
|  | 50 | 2 | 2 |
| 18 | 12.5 | 5 | 0 |
|  | 50 | 3 | 0 |
| 21 | 12.5 | 8 | 5 |
|  | 50 | 4 | 4 |
| 22 | 12.5 | 3 | 5 |
|  | 50 | 1 | 0 |
| 23 | 12.5 | 6 | 0 |
|  | 50 | 5 | 0 |
| 25 | 12.5 | 10 | 8 |
|  | 50 | 8 | 4 |
| 31 | 12.5 | 0 | 0 |
|  | 50 | 0 | 0 |
| 33 | 12.5 | 5 | 0 |
|  | 50 | 4 | 0 |
| 34 | 12.5 | 7 | 0 |
|  | 50 | 1 | 1 |
| 37 | 12.5 | 3 | 1 |
|  | 50 | 19 | 0 |
| 40 | 12.5 | 2 | 0 |
|  | 50 | 2 | 0 |
| 41 | 12.5 | 7 | 1 |
|  | 50 | 3 | 0 |
| 48 | 12.5 | 0 | 0 |
|  | 50 | 9 | 0 |
| 49 | 12.5 | 5 | 0 |
|  | 50 | 26 | 6 |
| 50 | 12.5 | 0 | 10 |
|  | 50 | 8 | 10 |
| 51/C | 12.5 | 15 | 0 |
|  | 50 | 7 | 0 |
| 53 | 12.5 | 0 | 9 |
|  | 50 | 2 | 12 |
| 54 | 12.5 | 1 | 0 |
|  | 50 | 2 | 0 |
| 73 | 12.5 | 0 | 0 |
|  | 50 | 0 | 0 |
| 77 | 12.5 | 5 | 3 |
|  | 50 | 3 | 2 |
| 78 | 12.5 | 0 | 5 |
|  | 50 | 0 | 11 |
| 79 | 12.5 | 0 | 0 |
|  | 50 | 0 | 0 |
| 80 | 12.5 | 1 | 0 |
|  | 50 | 1 | 0 |
| 81 | 12.5 | 0 | 1 |
|  | 50 | 0 | 0 |
| 82 | 12.5 | 1 | 4 |
|  | 50 | 0 | 0 |
| 83 | 12.5 | 0 | 16 |
|  | 50 | 0 | 18 |

Lipopolysaccharide Induced TNF-α Production in Balb/cJ Mice

Male Balb/cJ mice (Iffa Credo, France) weighing 25-33 g were randomly grouped (n=7 in test group, 7 in positive control group, 4 in negative control group). Test compounds, as well as vehicle [0.125% carboxymethyl-cellulose (Sigma, USA)], were administered to the mice intraperitoneally. Test compounds were administered at a dose of 10 mg/kg of body weight, in a volume of 10 mL/kg of body weight. Thirty minutes later, a sterile solution of lipopolysaccharide (LPS) (Sigma, USA) in saline was intraperitoneally administered at a concentration and volume of 25 µg/0.2 mL/mouse to each animal, except those in negative control. Ninety minutes following administration, all animals were sacrificed by puncturing a. carotis communis. The plasma concentration of TNF-α was determined by sandwich ELISA, using capture and detection antibodies (R&D, USA) according to manufacturer's recommendations. Results are presented in the following table as percent of inhibition of TNF-α production in comparison to the positive control (stimulated, but untreated animals).

TABLE 7

Percentage of inhibition of TNF-α production in LPS stimulated Balb/cJ mice treated with test compounds

| Example | % inhibition |
|---|---|
| azithromycin | 54 |
| clarithromycin | 63 |
| 1 | 64 |
| 2 | 59 |
| 8 | 93 |
| 12 | 69 |
| 14 | 96 |
| 15 | 100 |
| 17 | 84 |
| 21 | 61 |
| 31 | 92 |
| 34 | 78 |
| 48 | 52 |
| 49 | 43 |
| 54 | 58 |
| 62 | 59 |
| 73 | 90 |
| 77 | 92 |
| 78 | 89 |
| 79 | 84 |
| 80 | 86 |
| 81 | 91 |
| 82 | 72 |
| 83 | 77 |

Phorbol 12-Myristate 13-Acetate Induced Ear Oedema in CD1 Mice

Male CD1 mice (Iffa Credo, France) weighing 30-40 g were randomly grouped (n=6 in test group of which the untreated ear served as negative control; 6 in positive control group which also served as their own negative control group). Test compounds, as well as vehicle (Trans-phase Delivery System, containing benzyl alcohol 10%, acetone 40% and isopropanol 50%) (all from Kemika, Croatia), were administered topically to the internal surface of the left ear thirty minutes prior to administration of phorbol 12-myristate 13-acetate (PMA) (Sigma, USA). Test compounds were administered at a dose of 100, 250 or 500 μg/15 μL/ear. Thirty minutes later, 0.01% PMA solution in acetone was applied topically to the inner surface of the left ear of each animal in a volume of 12 μL/ear. During the treatment and challenge (stimulation), animals were anaesthetized with anaesthesia by inhalation. Six hours following challenge, animals were euthanized by intraperitoneal thiopental injection (PLIVA, Croatia). For assessing the auricular oedema, 8 mm discs were cut out of left and right auricular pinna and weighed. The degree of oedema was calculated by subtracting the weight of 8 mm disc of the untreated ear from that of the treated contralateral ear. The inhibition of oedema in the treated animals, presented in the Table 8, is expressed as percentage compared to control mice (0%).

TABLE 8

Percentage of inhibition of PMA induced ear oedema in CD1 mice treated with test compounds

| Compound | Dose | Oedema (% inhibition) |
|---|---|---|
| azithromycin | 100 μg | 0 |
|  | 250 μg | 83 |
|  | 500 μg | 90 |
| Example 8 | 100 μg | 54 |
|  | 250 μg | 74 |
|  | 500 μg | 94 |

Lung Neutrophilia Induced by Bacterial Lipopolysaccharide in Male BALB/cJ Mice

Male BALB/cJ mice (Iffa Credo, France), with average weight 30 g were randomly grouped (n=7 in testing group, 8 in positive control, 7 in negative control). Mice were administered intraperitoneally (i.p.) a single dose of 5 or 2.5 mg of test compound. Two hours after administration, 2 μg of bacterial lipopolysaccharide (LPS), dissolved in PBS in a volume of 60 μL, was intranasally administered to all experimental groups except the negative control group, which received the same volume (60 μL) of vehicle PBS. Animals were sacrificed approximately 24 hours after application of LPS in order to obtain bronchoalveolar lavage fluid (BALF), which was used to determine concentrations of IL-6 and TNF-α, absolute number of cells, and the percentage of neutrophils in BALF. Results are expressed as percentage of decrease of total cell number, relative number of neutrophils, and TNF-α, and IL-6 concentration in BALF of treated animals compared to positive control (LPS stimulated, but untreated animals).

TABLE 9

Percentage of decrease of total cell number, relative number of neutrophils, TNF-α and IL-6 concentration in BALF of treated animals

| Example | Dose (mg) | % decrease of total cell no. | % decrease of neutrophils | TNF-α | IL-6 |
|---|---|---|---|---|---|
| azithromycin | 5 | 77 | 37 | 66 | 72 |
| clarithromycin | 5 | 77 | 36 | 78 | 60 |
| 8 | 5 | 84 | 52 | 69 | 67 |
| 12 | 5 | 88 | 46 | 87 | 45 |
| 48 | 5 | 79 | 66 | 85 | 9 |
| 54 | 5 | 90 | 70 | 100 | 100 |
| 62 | 2.5 | 47 | 13 | 62 | 22 |

Results are expressed as percentage of decrease of total cell number, relative number of neutrophils, and TNF-alpha and IL-6 concentration in BALF of treated animals compared to positive control (LPS stimulated, but untreated animals).

Besides accumulation of inflammatory cells in BALF, the extent and anatomic site of pulmonary inflammation induced by LPS was assessed 24 hours after PBS or LPS exposure. Accumulation of granulocytes and mononuclear cells in peribronchial (PB) and perivascular (PV) lung tissue areas and in alveolar spaces was monitored following sacrifice of the animals.

Challenge with LPS induced significant accumulation of both granulocytes and mononuclear cells in lung tissue in comparison to groups challenged with PBS (negative control). The tested compounds significantly decreased accumulation of both granulocytes and mononuclears in lung tissue (PB and PV).

Septic Shock Induced by Bacterial Lipopolysaccharide in Male BALB/cJ Mice

Male BALB/cJ mice, (Iffa Credo, Lyon, France) 8 weeks old, weighing 25 g were randomly grouped (n=10 in testing groups and 15 in control group). Animals were primed with 4 μg bacterial lipopolysaccharide (LPS) that was dissolved in saline and administered i.pl. After 18-24 hours animals were challenged by an intravenous injection of 90 μg LPS in a volume of 0.2 mL. Animals were treated with the test compounds or the vehicle (control) intraperitoneally . . . or per os 30 min prior to each injection of LPS. Survival throughout 24 hours was monitored.

TABLE 10

Effect of compounds on survival of BALB/cJ mice after LPS-induced septic shock.

| Compound | Dose | Survival (%) |
|---|---|---|
| azithromycin | 1 mg/kg p.o. | 30 |
|  | 10 mg/kg p.o. | 60 |
|  | 100 mg/kg p.o. | 70 |
| Example 8 | 10 mg/kg i.p. | 50 |
|  | 100 mg/kg p.o. | 100 |

In all the tests, the compounds of the present invention were found to be very active as anti-inflammatories and the anti-inflammatory activity was found to be comparable to or greater than that of the comparative macrolide compounds.

It is therefore clear that the compounds of formula (I), which have anti-inflammatory activity, can be useful in both acute and chronic treatment and in the prophylaxis of inflammatory pathologies, especially of those pathologies associated with altered cellular functionality of the neutrophils, for example rheumatoid arthritis, vasculitis, glomerulonephritis, damage from ischemic reperfusion, atherosclerosis, septic shock, ARDS, COPD and asthma.

The therapeutically effective quantities will depend on the age and on the general physiological condition of the patient, the route of administration and the pharmaceutical formulation used. The therapeutic doses will generally be between about 10 and 2000 mg/day and preferably between about 30 and 1500 mg/day.

The compounds of the present invention for use in treatment and/or prophylaxis of the pathologies indicated above will preferably be used in a pharmaceutical form suitable for oral, rectal, sublingual, parenteral, topical, transdermal and inhalational administration.

The present invention further relates to pharmaceutical formulations containing a therapeutically effective quantity of a compound of formula (I) or one of its salts mixed with a pharmaceutically acceptable vehicle. The pharmaceutical formulations of the present invention can be liquids that are suitable for oral and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

Depending on the type of formulation, in addition to a therapeutically effective quantity of one or more compounds of formula (I), they will contain solid or liquid excipients or diluents for pharmaceutical use and possibly other additives normally used in the preparation of pharmaceutical formulations, such as thickeners, aggregating agents, lubricants, disintegrating agents, flavorings and colorants.

The pharmaceutical formulations of the invention can be produced in accordance with the usual methods.

In the following examples, the structural representation of a pendant —O or —N is equivalent to the —OH, —NH, or —$NH_2$ as appropriate based on atom valency.

The following abbreviations are used in the text: DBU for 1,8-diazabicyclo[5.4.0]undec-7-ene, DCM for dichloromethane, DMAP for 4-dimethylaminopyridine, DMF for N,N-dimethylformamide, DMSO for dimethyl sulfoxide, EDCxHCl for 1-(3-dimethylaminopropyl)-3-ethylcarbodiimide hydrochloride, EtOAc for ethyl acetate, KO-t-Bu for potassium tert-butoxide, MeOH for methanol, EtOH for ethanol, t-BuOH for tert-butanol, TEA for triethylamine and THF for tetrahydrofuran, MIBK for methyl iso-buthyl ketone, DCC for dicyclohexylcarbodiimide, DMAP for 4-dimethylaminopyridine, DIPEA for N,N-diisopropylethylamine, CDI for 1,1'-carbonyldiimidazole, and DCE for dichloroethane.

The compounds and process of the present invention will be better understood in connection with the following examples, which are intended as an illustration only and not limiting the scope of the invention. Various changes and modifications to the disclosed embodiments will be apparent to those skilled in the art and such changes and modifications including, without limitation, those relating to the chemical structures, substituents, derivatives formulations and/or methods of the invention may be made without departing from the spirit of the invention and the scope of the appended claims.

EXAMPLES

2'-O-Acetyl-protected compounds may be prepared by the procedure described by W. R. Baker et al. in *J. Org. Chem.* 1988, 53, 2340 9-O-(2-chlorobenzyl)-protected oxime compounds may be prepared by the procedure described by Y. Watanabe et al. in *J. Antibiot.* 1993, 46, 1163. 9-O-(1-isopropoxycyclohexyl)-protected oxime compounds may be prepared by the procedure described by Z. Ma et al. in *J. Med. Chem.* 2001, 44, 4137. 11,12-Carbonate compounds may be prepared by procedure as described in international patent application WO 02/50091 or by procedure as described by S. Djokic et al. in *J. Chem. Res.* (S) 1988, 152. 11-O-Methyl azithromycin may be prepared by procedure as described by Kobrehel et al. in *J. Antibiotics* 1992, 45, 527. All documents cited in this paragraph are incorporated by reference in their entirety.

Example 1

11,12-Carbonate-11,12-dideoxy-4"-O-(3-diethylamino-propionyl)-azithromycin

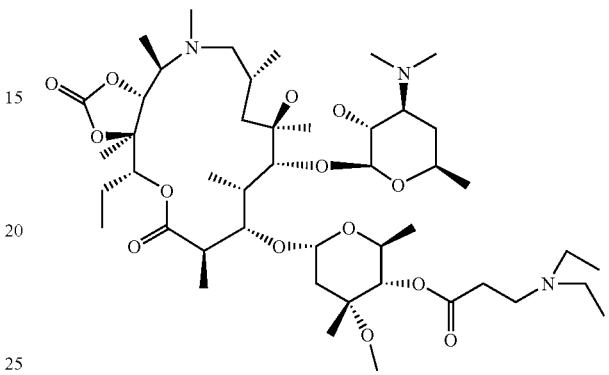

11,12-Carbonate-11,12-dideoxy-4"-O-propenoyl-azithromycin (0.5 g, 0.6 mmol), obtained as described in international patent application WO 03/042228, intermediate 50, and diethylamine (0.72 mL, 7 mmol) were dissolved in dry methanol (60 mL) and the mixture stirred overnight at 40° C. Methanol was evaporated under reduced pressure and the crude product was purified by column chromatography (DCM/MeOH/$NH_4OH$=90:9:0.5) to afford the title compound.

MS (ES+) m/z: $[MH]^+$=902.46

$^{13}$C-NMR (125 MHz, $CDCl_3$) δ: 177.1, 172.1, 153.3, 102.8, 95.3, 85.9, 85.1, 79.0, 78.0, 76.3, 73.3, 73.0, 70.7, 68.2, 67.7, 65.5, 62.9, 61.2, 49.5, 48.2, 46.7, 45.3, 43.0, 41.9, 40.4, 35.3, 34.4, 29.3, 26.8, 26.2, 22.1, 22.0, 21.6, 21.2, 17.8, 14.9, 14.2, 10.5, 10.4, 5.5.

Example 2

4"-O-(3-Diethylamino-propionyl)-8a-aza-8a-homo-erythromycin A

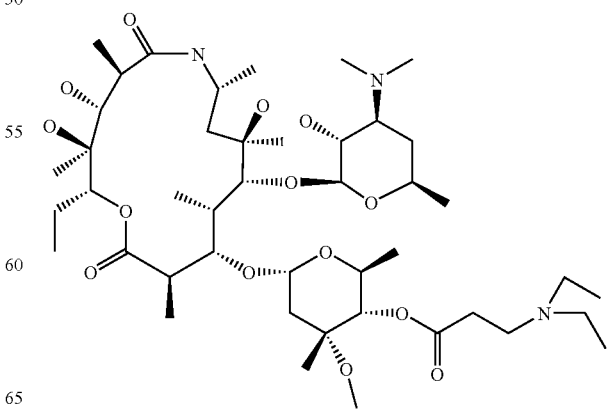

4"-O-Propenoyl-8a-aza-8a-homoerythromycin A (0.34 g, 0.42 mmol), obtained as described in international patent application WO 02/32917 (incorporated by reference) example 59, and diethylamine (0.56 mL, 5.4 mmol) were dissolved in dry methanol (50 mL) and the mixture stirred overnight at 40° C. Methanol was evaporated under reduced pressure and the crude product was purified by column chromatography (DCM/MeOH/NH$_4$OH=90:9:1.5) to afford the title compound.

MS (ES+) m/z: [MH]$^+$=876.48

$^{13}$C-NMR (125 MHz, DMSO) δ: 177.2, 174.6, 171.8, 102.2, 93.9, 82.1, 77.9, 76.5, 75.7, 74.6, 73.2, 72.5, 70.7, 70.4, 65.8, 64.7, 62.1, 48.7, 48.2, 45.9, 44.8, 42.2, 40.7, 40.2, 34.2, 32.7, 30.3, 27.2, 23.5, 21.5, 21.4, 20.5, 17.6, 17.2, 14.4, 11.5, 11.3, 9.2, 8.8.

Example 3

4"-O-(3-Diethylamino-Propionyl)-6-O-methyl-8a-aza-8a-homoerythromycin A

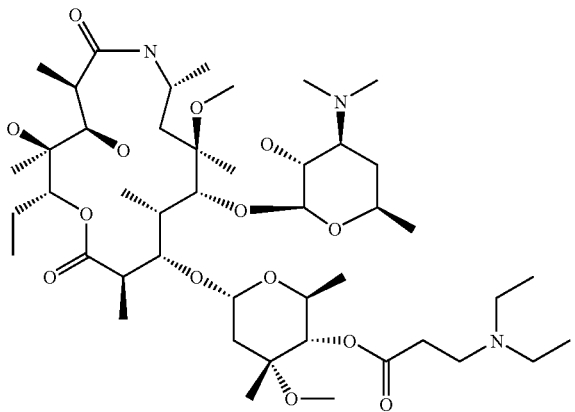

Diethyl amine (80 μl, 0.95 mol) was added to a solution of 4"-O-propenoyl-6-O-methyl-8a-aza-8a-homoerythromycin A (0.15 g, 0.19 mmol), obtained as described in international patent application WO 02/32917, example 9, (0.15 g, 0.19 mmol) in isopropanol (2 mL) and the reaction mixture was stirred at 70° C. overnight in tube. Isopropanol was evaporated, the residue was purified by SP column (DCM/MeOH/NH$_4$OH=90:9:0.5) to give the title compound (34 mg).

MS (ES) m/z: [MH]$^+$=890 (95%).

Example 4

2'-O-Acetyl-3'-N-methyl-3'-N-(2-cyanoethyl)-4"-O-propenoyl-6-O-methyl-9a-aza-9a-homoerythromycin A Intermediate 1: 3'-N-Demethyl-6-O-methyl-9a-aza-9a-homoerythromycin A In a solution of a 9a-lactame (WO 99/51616, incorporated by reference) (1 g, 1.31 mmol) in methanol (25 ml) sodium acetate (0.54 g, 6.56 mmol) and iodine (0.37 g, 1.44 mmol) were added. The reaction mixture was kept stirring and irradiated with a 500 W for 8 hours, while reaction mixture refluxed. The methanol was evaporated off under vacuum and the residue was taken up in ethyl acetate and extracted with 10% sodium thiosulphate (3×20 ml). The combined aqueous phase was treated with 0.1 N NaOH solution to alkaline pH and extracted with ethyl acetate (4×20 ml). After drying with sodium sulphate, the organic phase was filtered off and evaporated under vacuum to give intermediate 1 (0.64 g, 66% yield).

MS (ES) m/z: [MH]$^+$=748 (90.47%)

Intermediate 2: 3'-N-Methyl-3'-N-(2-cyanoethyl-6-O-methyl-9a-aza-9a-homoerythromycin A A solution of intermediate 1 (0.64 g, 0.854 mmol in acrylonitrile (20 ml) was refluxed over the night. The excess acrylonitrile was evaporated off under vacuum to give the crude product of the intermediate 2. Purification by SP column (silica, eluent CH$_2$Cl$_2$:MeOH: NH$_3$=90:9:0.5) gave intermediate 2 (0.43 g, 64% yield).

MS (ES) m/z: [MH]$^+$=802 (88%)

Intermediate 3: 2'-O-Acetyl-3'-N-methyl-3'-N-(2-cyanoethyl)-6-O-methyl-9a-aza-9a-homoerythromycin A Acetic anhydride (41 μl, 0.43 mmol) was added to a solution of intermediate 2 (0.49 g, 0.6 mmol) and DIPEA (149 μl, 0.86 mmol) in CH$_2$Cl$_2$ (5 ml) and the reaction mixture was stirred overnight. The CH$_2$Cl$_2$ was evaporated under vacuum and the residue was taken up in ethyl acetate and extracted with NaHCO$_3$. After drying with sodium sulphate, the organic phase was filtered off and evaporated under vacuum to give intermediate 3 (0.36 g, 60% yield).

MS (ES) m/z: [MH]$^+$=844 (75%)

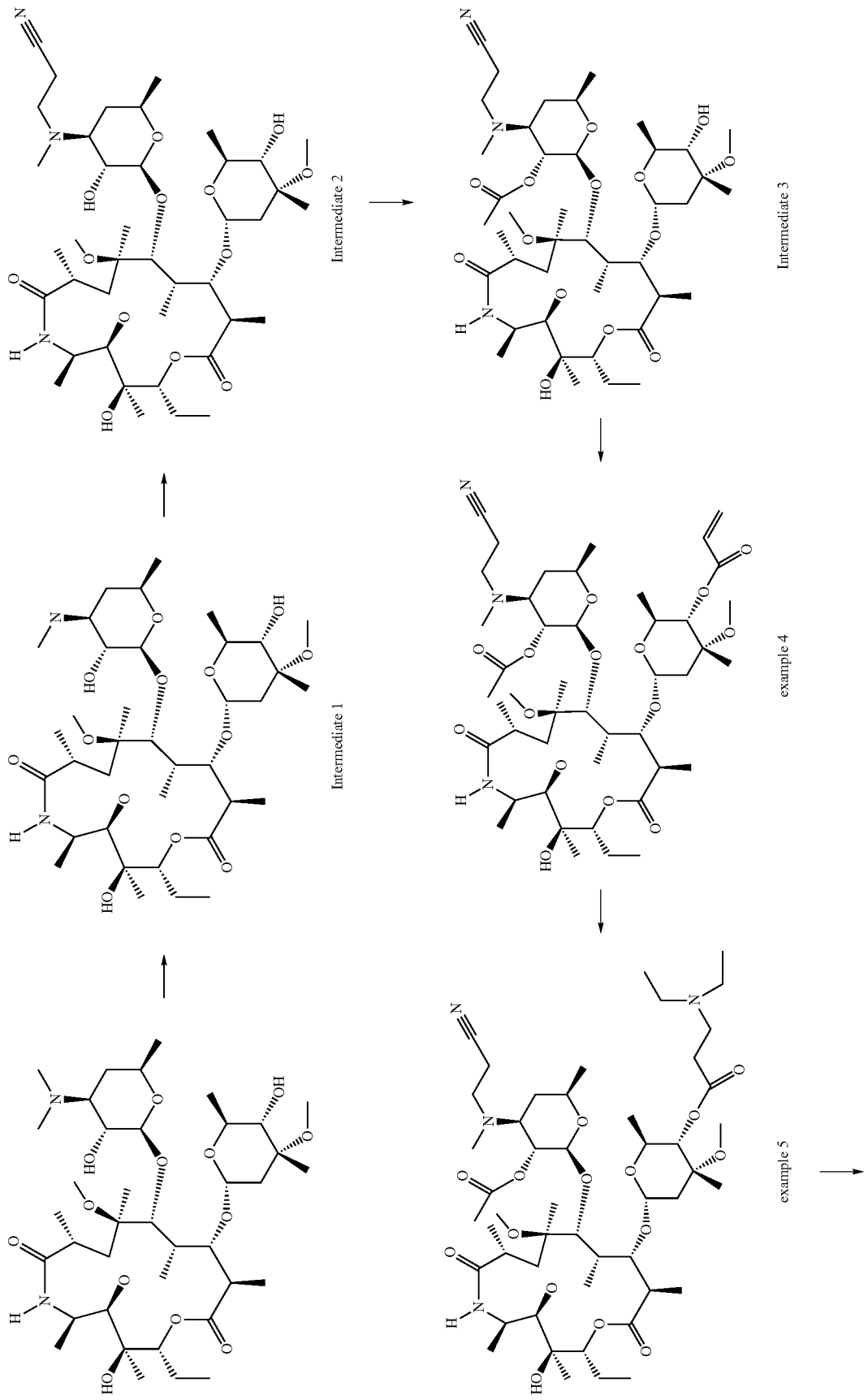

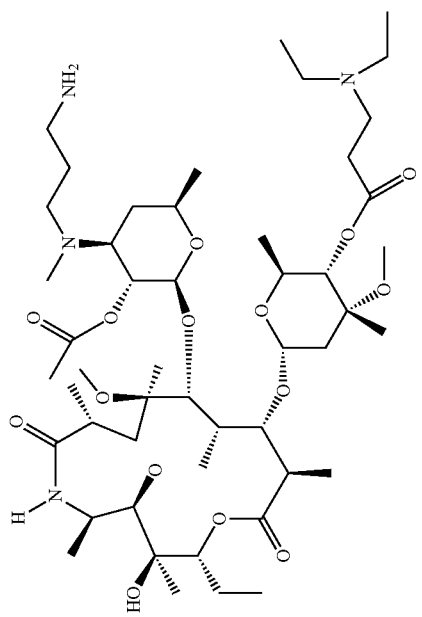
example 6

To a solution of intermediate 3 (0.362 g, 0.43 mmol) in dry toluene (5 ml), TEA (238 μl, 1.72 mmol) and 3-chloropropionyl chloride (82 μl, 0.86 mmol) were added. The reaction mixture was cooled down with water (15-20° C.) and stirred for 4 hours. Toluene was evaporated under vacuum and the residue was extracted with $CH_2Cl_2$ and $NaHCO_3$. After drying with sodium sulfate, the organic phase was filtered off and evaporated under vacuum to give titled compound (0.36 g, 95% yield).

MS (ES) m/z: $[MH]^+$=898 (63%)

Example 5

2'-O-Acetyl-3'-N-methyl-3'-N-(2-cyanoethyl)-4''-O-(3-diethylaminopropionyl)-6-O-methyl-9a-aza-9a-homoerythromycin A Diethyl amine (186 μl, 1.78 mmol) was added to a solution of compound of example 4 (0.32 g, 0.357 mmol) in isopropanol (5 ml) and the reaction mixture was stirred at 70° C. over night in a screw cup. Isopropanol was evaporated giving crude titled compound (0.09 g, 0.093 mmol).

Example 6

2'-O-Acetyl-3'-N-methyl-3'-N-(3-aminopropyl)-4''-O-(3-diethylaminopropionyl)-6-O-methyl-9a-aza-9a-homoerythromycin A Compound from example 5 (0.09 g, 0.093 mmol) was dissolved in glacial acetic acid (25 ml) $PtO_2$ was added. Using Parr apparatus, the solution was stirred under a hydrogen atmosphere overnight. Filtration through a pad of Celite, evaporation under vacuum and purification by SP column (5 g silica, eluent $CH_2Cl_2$:MeOH: $NH_3$=90:9:0.5) gave the title product (16.5 mg).

MS (ES) m/z: $[MH]^+$=975 (88%)

Example 7

4'',11-di-O-(3-Diethylamino-propionyl)-6-O-methyl-9a-aza-9a-homoerythromycin A

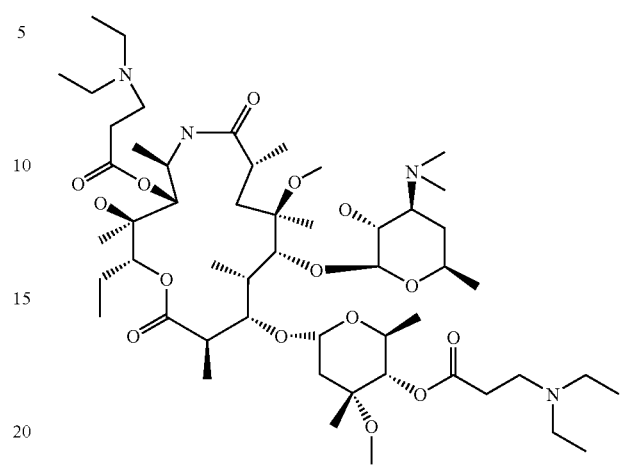

Diethylamine (2.08 mL, 20 mmol) was added to the solution of compound 2'-O-acetyl-4,11-di-O-propenoyl-6-O-methyl-9a-aza-9a-homoerythromycin A (prepared according to WO 03/042228 with excess of 3-chloropropionyl chloride) (0.91 g, 1 mmol) in dry methanol (100 mL). The reaction mixture was stirred overnight at 40° C. Methanol was evaporated under reduced pressure and the crude product was purified by column chromatography (DCM-MeOH—$NH_4OH$=90:9:1.5) to afford the title compound (0.59 g, 58% yield) as a white solid.

MS (ES) m/z: $[MH]^+$=1018

Example 8

4''-O-(3-Diethylamino-propionyl)-6-O-methyl-9a-aza-9a-homoerythromycin A

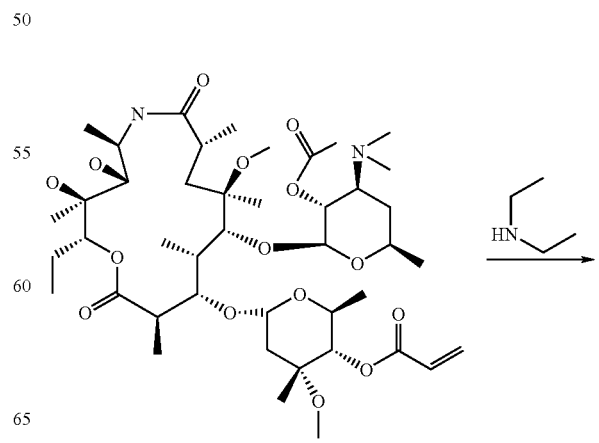

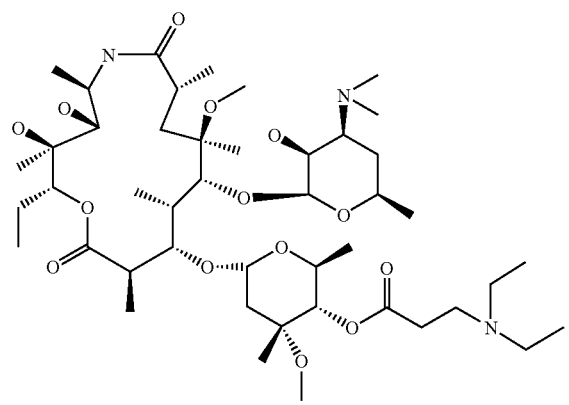

Diethylamine (1.04 mL, 10 mmol) was added to the solution of compound 2'-O-acetyl-4"-O-propenoyl-6-O-methyl-9a-aza-9a-homoerythromycin A (prepared according to WO 03/042228, incorporated by reference) (0.86 g, 1 mmol) in dry methanol (100 mL). The reaction mixture was stirred overnight at 40° C. Methanol was evaporated under reduced pressure and the crude product was purified by flash chromatography (DCM/MeOH/NH$_4$OH=90:9:0.5) to afford the title compound (0.5 g, 57% yield) as a white solid.

MS (ES) m/z: [MH]$^+$=891

All compounds in this Example each have the substituent bonded at the C-2 of the desosaminyl sugar in the S absolute stereochemical configuration, and therefore, is in an anti stereochemical configuration compared to the stereochemical configurations of the substituents bonded at the C-1 and C-3 of the desosaminyl sugar.

Example 9

11,12-Carbamate-11,12-dideoxy-4"-O-(3-diethylamino-propionyl)-6-O-methyl-erythromycin A

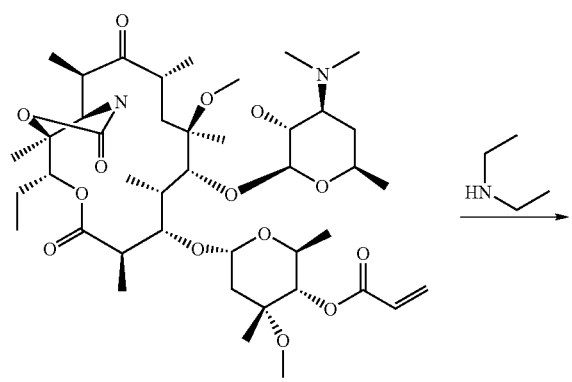

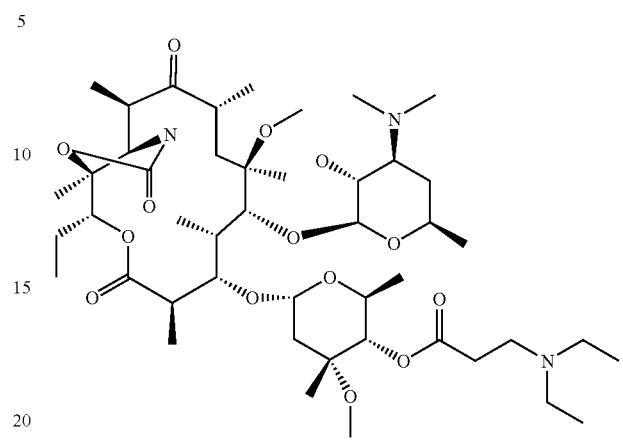

Diethylamine (1.04 mL, 10 mmol) was added to the solution of 11,12-carbamate-11,12-dideoxy-4"-O-propenoyl-6-O-methyl-erythromycin A (WO 03/042228) (0.83 g, 1 mmol) in dry methanol (100 mL). The reaction mixture was stirred overnight at 40° C. Methanol was evaporated under reduced pressure and the crude product was purified by column chromatography (silica, 2000/200/8 CH$_2$Cl$_2$/hexane/TEA eluant) to afford the title compound (0.58 g, 64% yield) as a white solid.

MS (ES) m/z: [MH]$^+$=901

Example 10

11,12-(N-Methyl-carbamate)-11,12-dideoxy-4-O-(3-diethylaminopropionyl)-6-O-methyl-erythromycin A

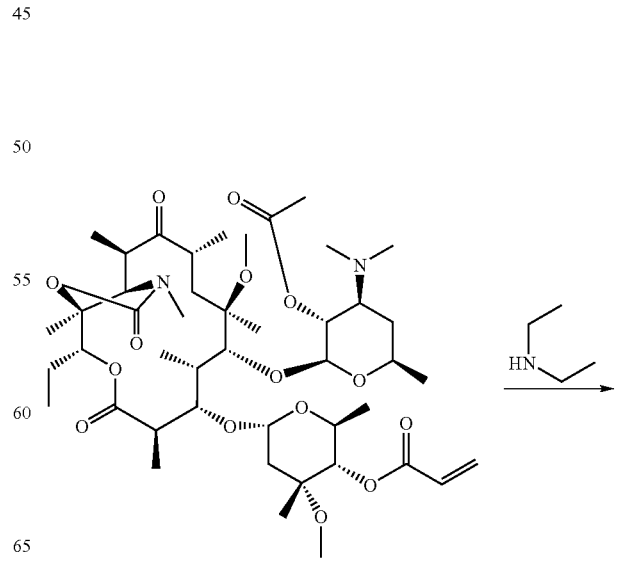

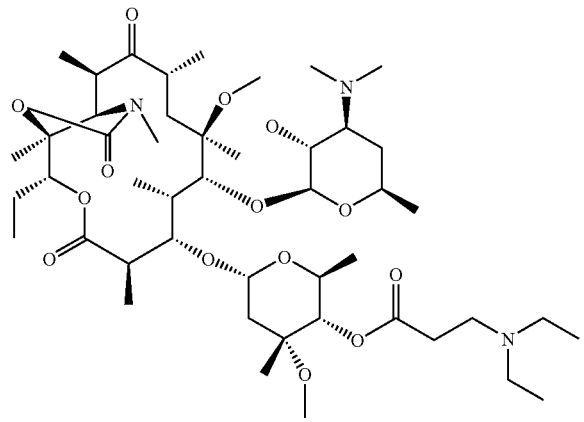

Diethylamine (1.04 mL, 10 mmol) was added to the solution of 11,12-(N-methylcarbamate)-11,12-dideoxy-4"-O-propenoyl-6-O-methyl-erythromycin A (WO 03/042228) (0.88 g, 1 mmol) in dry methanol (100 mL). The reaction mixture was stirred overnight at 40° C. Methanol was evaporated under reduced pressure and the crude product was purified by column chromatography (silica, 90/9/0.5 CH$_2$Cl$_2$/MeOH/NH$_4$OH eluent) to afford the title compound (0.68 g, 75% yield) as a white solid.

MS (ES) m/z: [MH]$^+$=915

Example 11

4"-O-(3-methylamino-propionyl)-6-O-methyl-9a-aza-9a-homoerythromycin A

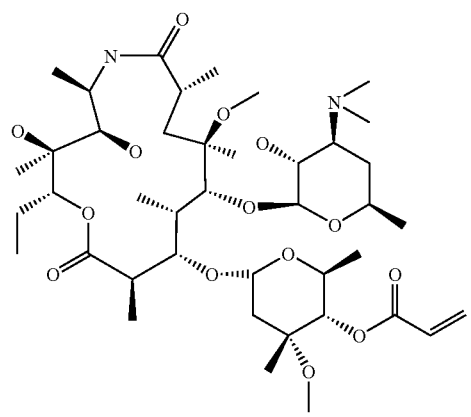

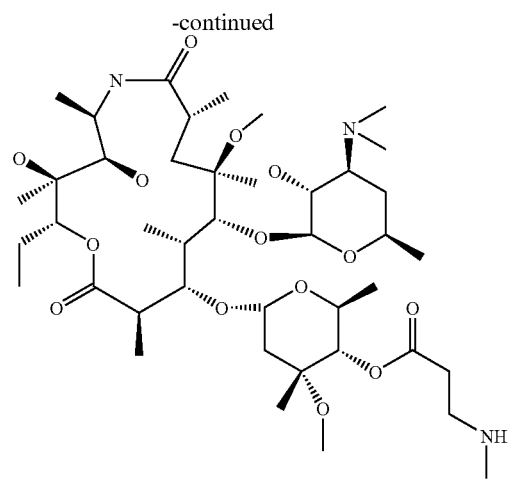

4"-O-Propenoyl-6-O-methyl-9a-aza-9a-homoerythromycin A (prepared according to WO 03/042228) (0.82 g, 1 mmol) was dissolved in methylamine (33% wt. solution in absolute ethyl alcohol (6 mL, 50 mmol). The reaction mixture was stirred for 4 hours at room temperature. Ethanol was evaporated under reduced pressure and the crude product was purified by column chromatography (silica, 90/9/1.5 CH$_2$Cl$_2$/MeOH/NH$_4$OH eluent) to afford the title compound (0.48 g, 57% yield) as a light yellow solid.

MS (ES) m/z: [MH]$^+$=849

Example 12

4"-O-(3-imethylamino-propionyl)-6-O-methyl-9a-aza-9a-homoerythromycin A

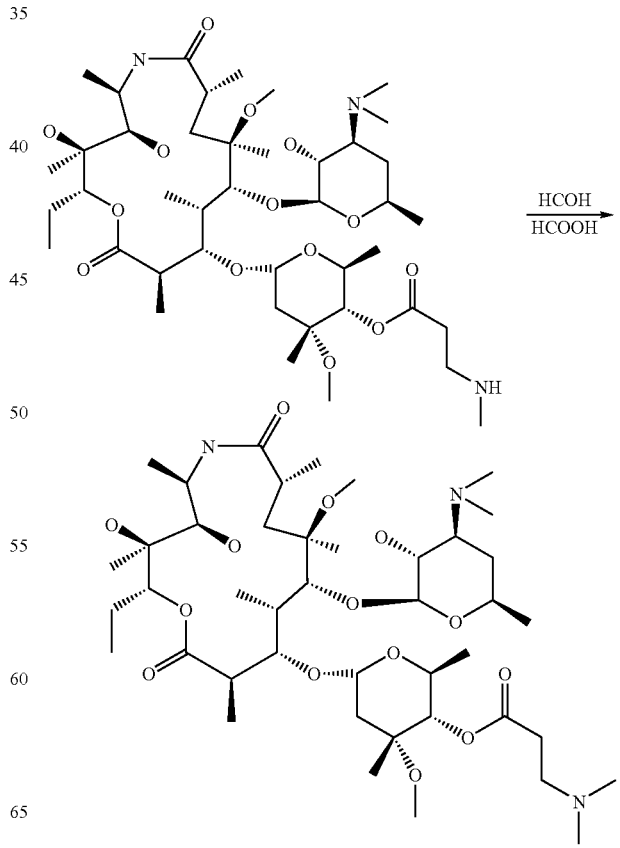

Formaldehyde (37 wt % solution in water) (0.23 mL, 3 mmol) and formic acid (0.055 mL, 1.5 mmol) was added to the solution of compound from example 11 (0.85 g, 1 mmol) in chloroform (40 mL). The reaction mixture was stirred for 3 hours at 70° C. Chloroform was evaporated under reduced pressure and the crude product was purified by column chromatography (silica, 90/9/1.5 $CH_2Cl_2$/MeOH/$NH_4OH$ eluent) to afford the title compound (0.62 g, 72% yield) as a white solid.

MS (ES) m/z: $[MH]^+$=863

Examples 13 to 44

General Procedure for Michael Addition

To a solution of 4″-O-Propenoyl-9a-aza-9a-homoerythromycin A, obtained as described in international patent application WO 02/32917 (incorporated by reference) in acetonitrile (1 mL) was added 5 equivalents of the amine component. The mixture was heated at 70° C. for 48 hours, cooled to room temperature and a scavanger resin (isocyanate polymer bound for secondary amines or 4-benzyloxybenzaldehyde polymer bound for primary amines, 3 eq.) and $CH_2Cl_2$ (3 mL) were subsequently added. After 1 day the resin was filtered off, washed with MeOH (1 mL), $CH_2Cl_2$ (1 mL) and again with MeOH (1 mL). The solvent was evaporated giving the desired product.

The table that follows the General procedure gives the structures of amines, as well as the products of formula (I).

| Amine | Product | MS (ES+) m/z $[MH]^+$ (m/z $[MH_2]^{2+}$) |
|---|---|---|
| 1-(2-aminoethyl)pyrrolidine | example 13 | 932.6 (466.3) |
| 1-(diethylaminoethyl)-piperazine | example 14 | 1003.6 (501.8) |

-continued

| Amine | Product | MS (ES+) m/z [MH]+ (m/z [MH₂]²⁺) |
|---|---|---|
| 2-(methylamino)ethanol | example 15 | 893.6 (446.8) |
| diethanolamine | example 16 | |

-continued

| Amine | Product | MS (ES+) m/z [MH]+ (m/z [MH₂]²⁺) |
|---|---|---|
| 1-(2-dimethylaminoethyl)-piperazine | example 17 | 975.6 (487.8) |
| 1-[2-(2-hydroxyethoxy)ethyl]piperazine | example 18 | 992.6 (496.3) |

-continued
| Amine | Product | MS (ES+) m/z [MH]+ (m/z [MH2]2+) |
|---|---|---|
| 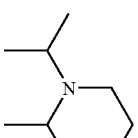 2-(diisopropilamino)ethylamine | 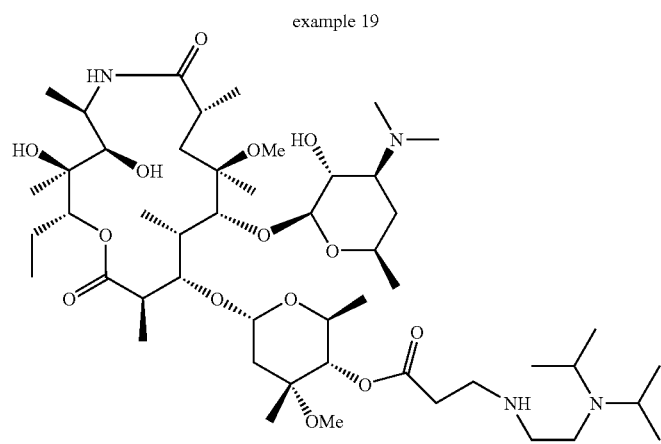 example 19 | 962.6 (481.3) |
| 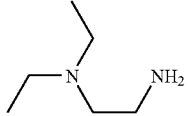 3-diethylamino-1-propylamine | 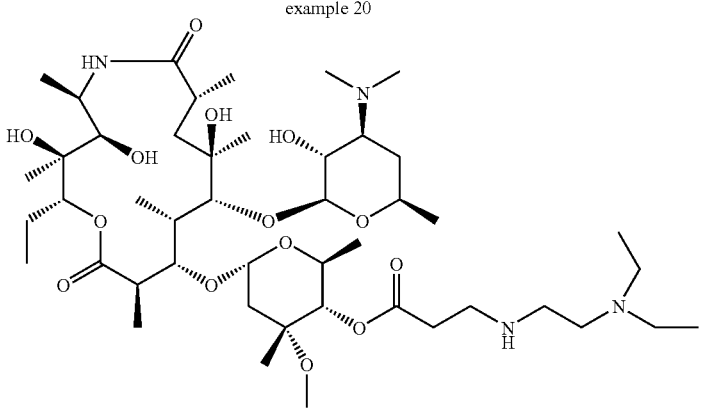 example 20 | |
| 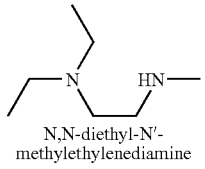 N,N-diethyl-N'-methylethylenediamine | 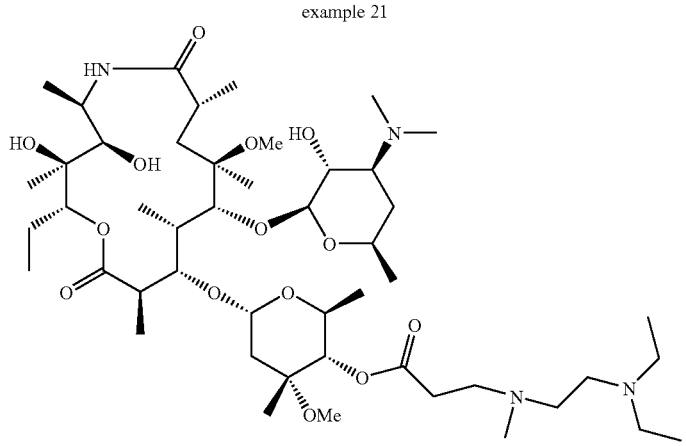 example 21 | 948.6 (474.3) |

-continued
| Amine | Product | MS (ES+) m/z [MH]+ (m/z [MH$_2$]$^{2+}$) |
|---|---|---|
| 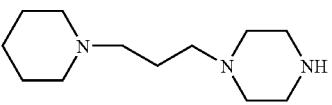 1-(3-piperidinopropyl)-piperazine | example 22 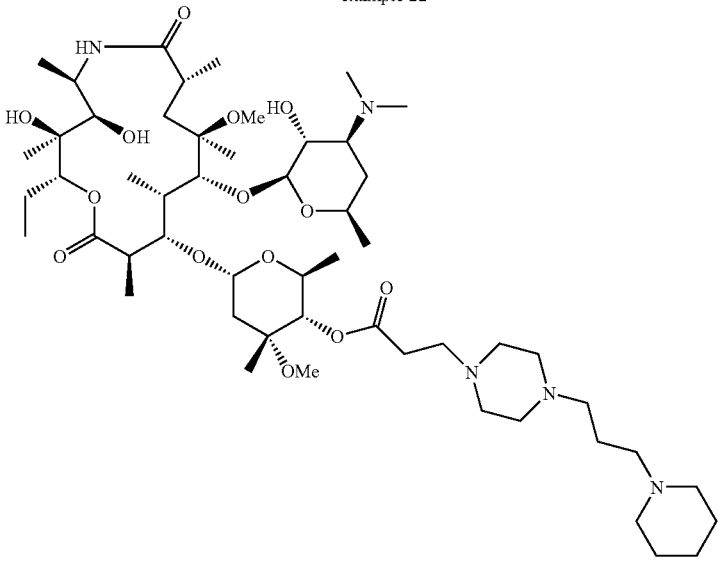 | 1029.6 (514.8) |
| 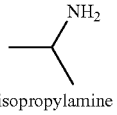 isopropylamine | example 23 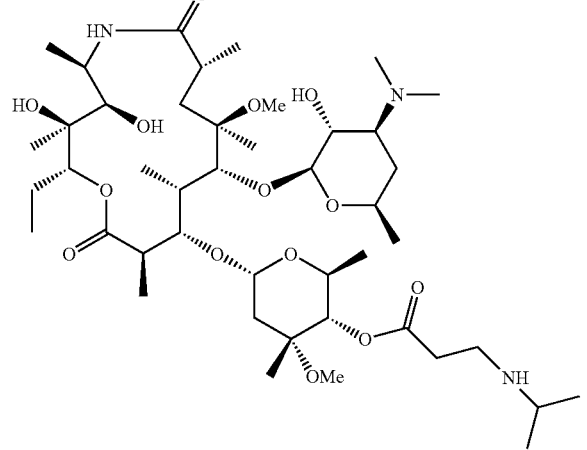 | 877.6 (438.8) |
| 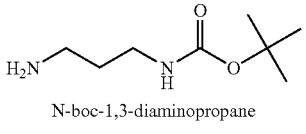 N-boc-1,3-diaminopropane | example 24 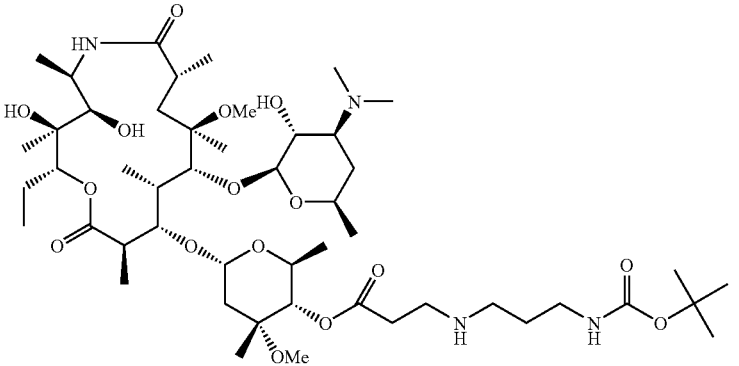 | 992.8 (496.4) |

| Amine | Product | MS (ES+) m/z [MH]+ (m/z [MH2]2+) |
|---|---|---|
| 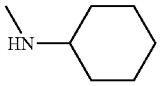 N-methylcyclohexylamine | 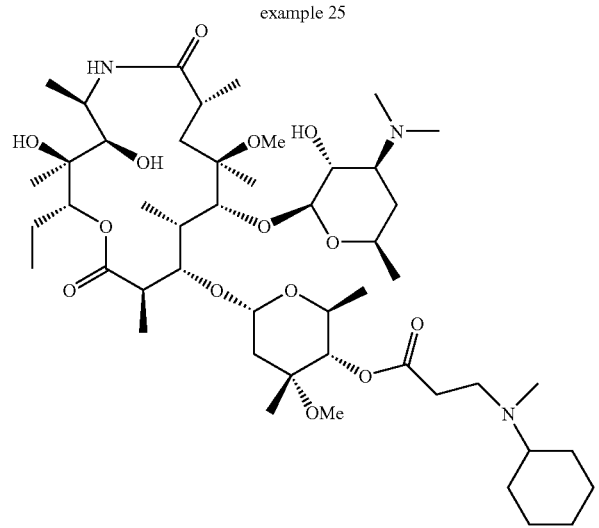 example 25 | 931.6 (465.9) |
| 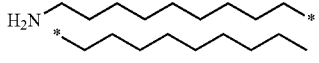 octadecylamine | 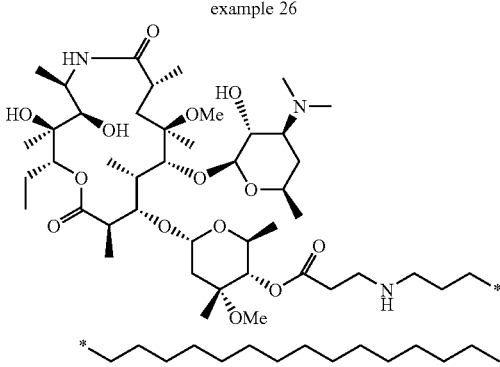 example 26 | 1087.8 (543.9) |
| 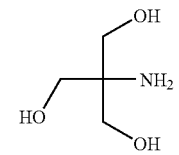 tris(hydroxymethyl)aminomethane | 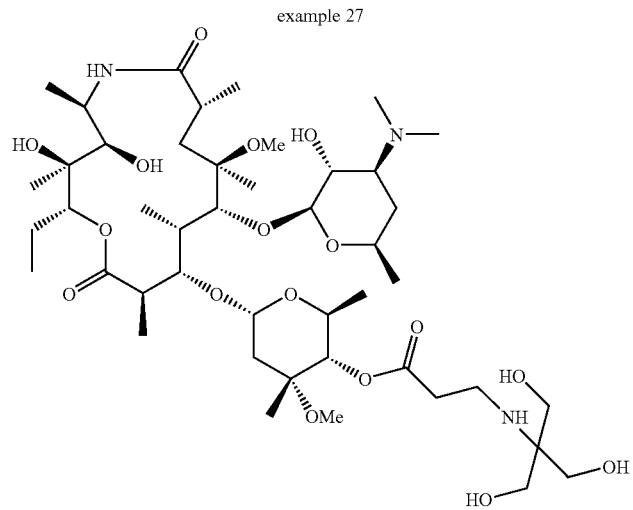 example 27 | |

-continued
| Amine | Product | MS (ES+) m/z [MH]+ (m/z [MH2]2+) |
|---|---|---|
| isobutylamine | example 28 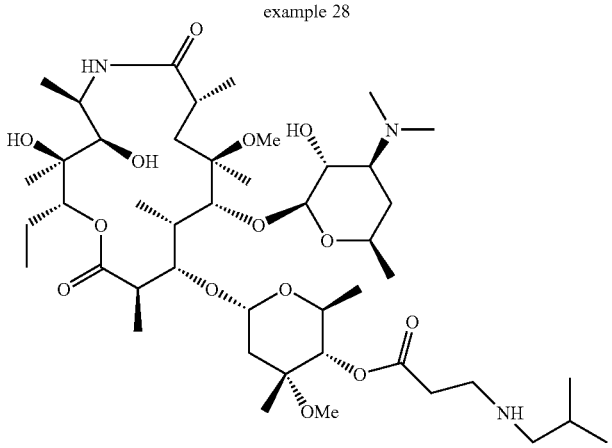 | 891.6 (445.8) |
| 2-(ethythio)ethylamine hydrochloride | example 29 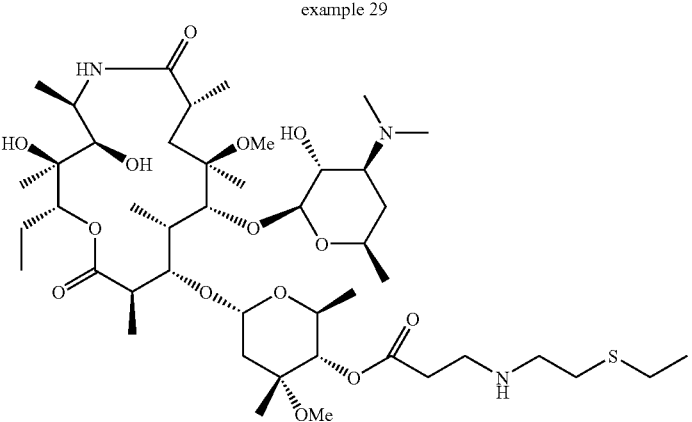 | |
| 1-(2-methoxyethyl)-piperazine | example 30 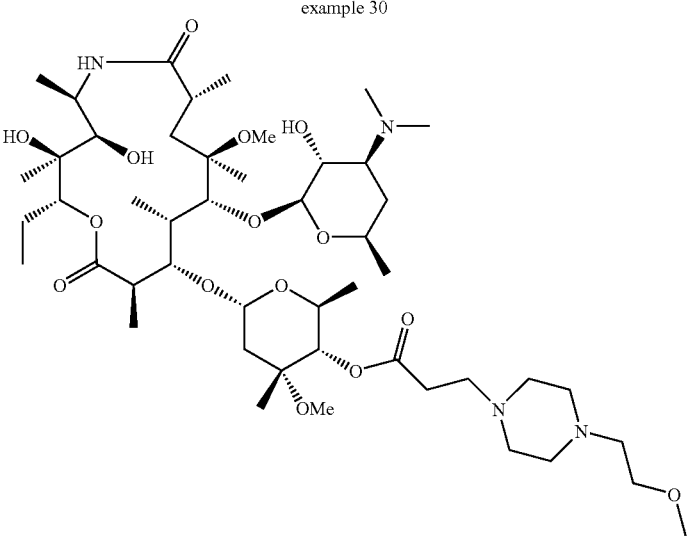 | 962.6 |

-continued
| Amine | Product | MS (ES+) m/z [MH]+ (m/z [MH2]2+) |
|---|---|---|
| 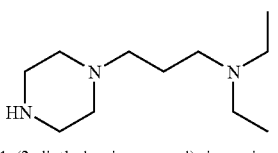<br>1-(3-diethylamino-propyl)piperazine | example 31<br>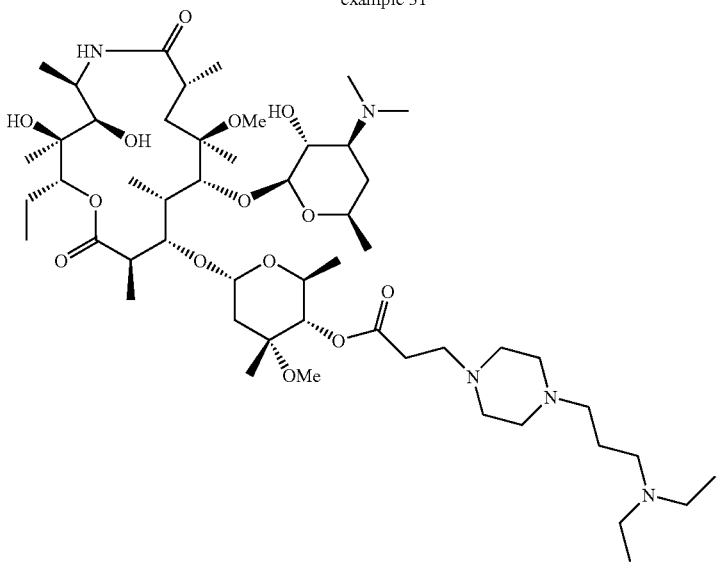 | 1017.8 |
| 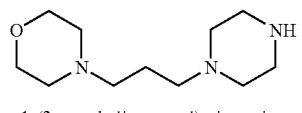<br>1-(3-morpholinopropyl)-piperazine | example 32<br>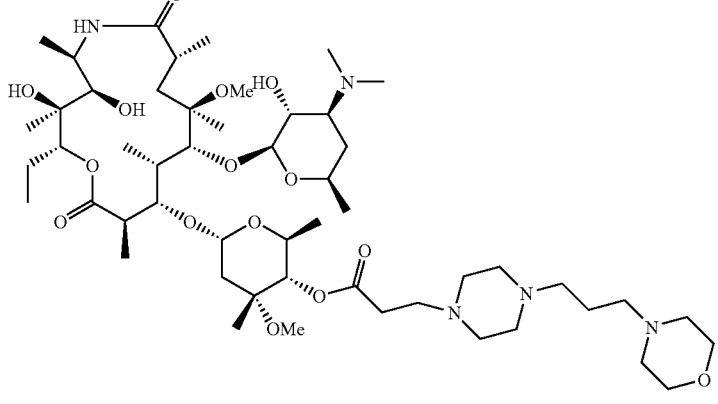 | 1031.8 |
| 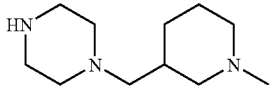<br>1-(N-methyl-3-piperidylmethyl)-piperazine | example 33<br>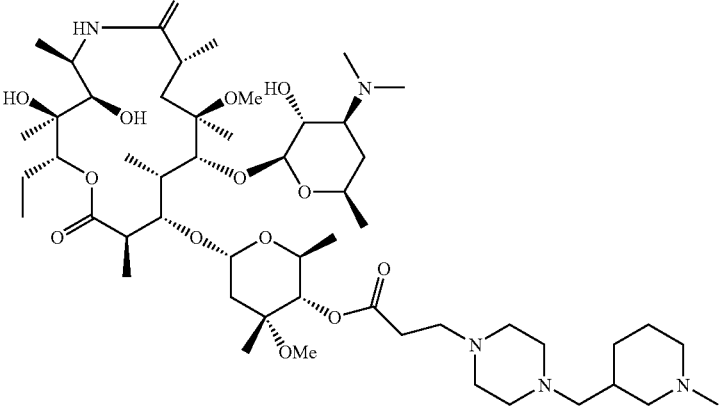 | 1015.6 |

-continued
| Amine | Product | MS (ES+) m/z [MH]+ (m/z [MH₂]²⁺) |
|---|---|---|
| 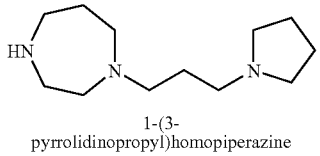 1-(3-pyrrolidinopropyl)homopiperazine | 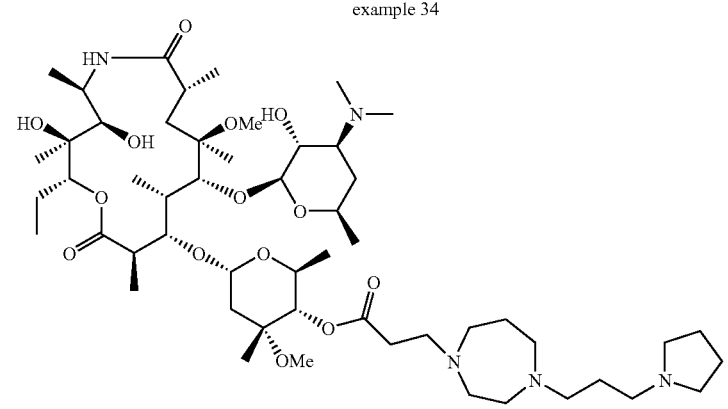 example 34 | 1029.8 |
| 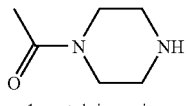 1-acetylpiperazine | 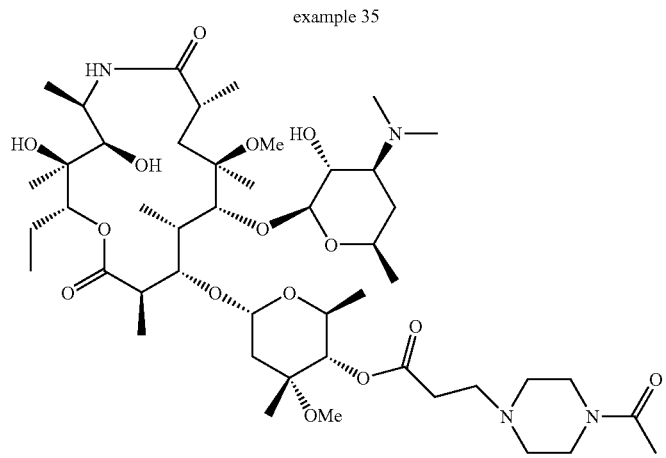 example 35 | 946.6 |
| 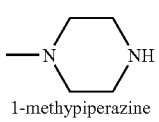 1-methypiperazine | 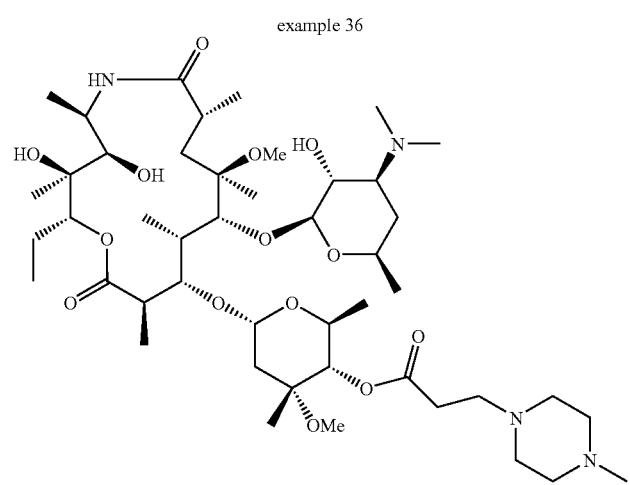 example 36 | 918.6 |

-continued

| Amine | Product | MS (ES+) m/z [MH]+ (m/z [MH$_2$]$^{2+}$) |
|---|---|---|
| 3,5-dimethylpiperidine | example 37 | 931.8 |
| cyclohexylamine | example 38 | 918.6 |

-continued
| Amine | Product | MS (ES+) m/z [MH]+ (m/z [MH₂]²⁺) |
|---|---|---|
| 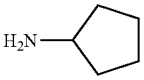 cyclopentylamine | example 39 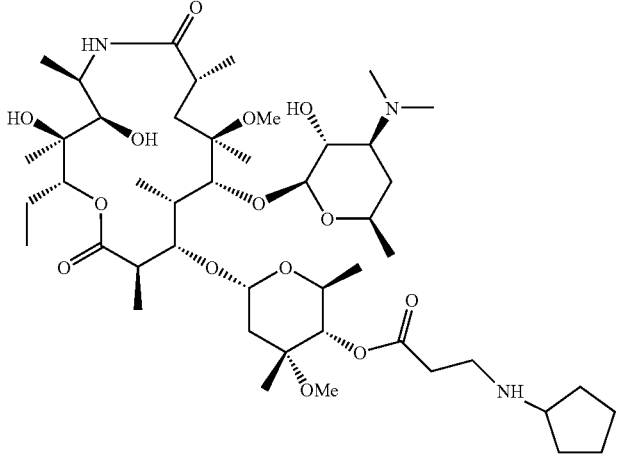 | 903.6 |
| 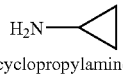 cyclopropylamine | example 40 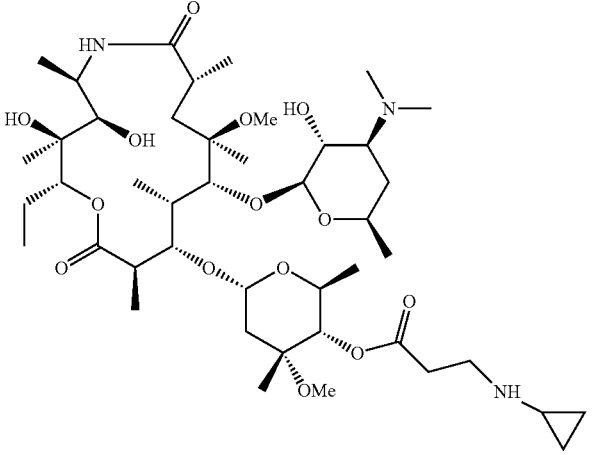 | 875.6 |
| 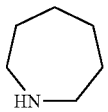 hexamethyleneimine | example 41 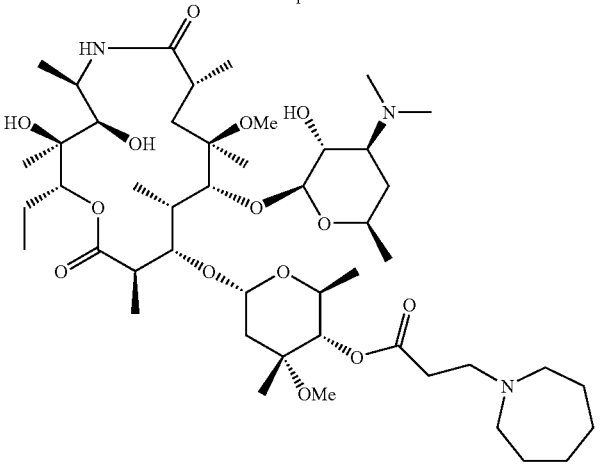 | 917.8 |

-continued
| Amine | Product | MS (ES+) m/z [MH]+ (m/z [MH2]2+) |
|---|---|---|
|  morpholine | 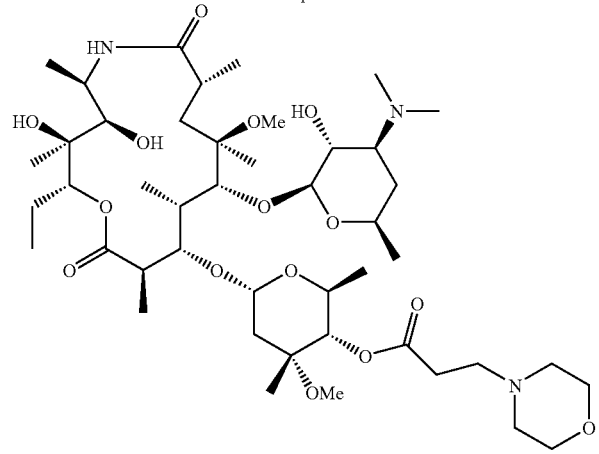 example 42 | 905.6 |
|  piperidine | 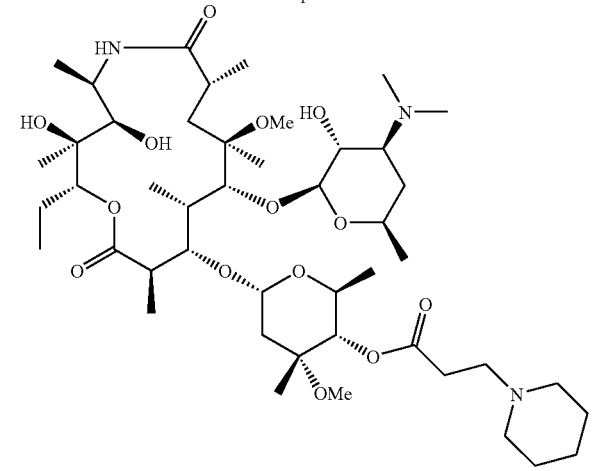 example 43 | 903.8 |
|  pyrrolidine | 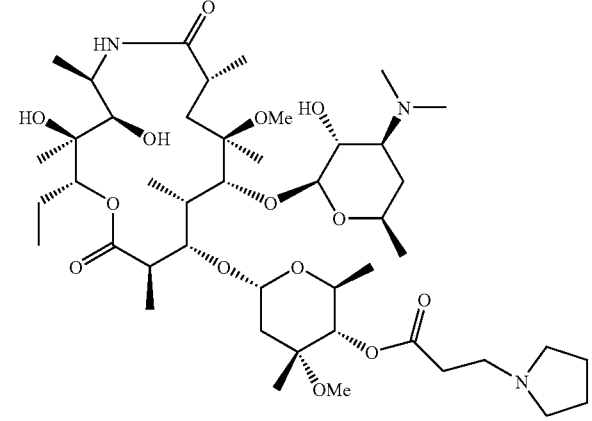 example 44 | 889.6 |

Example 45

3'-N-Methyl-3'-N-2'-O-diacetyl-4-O-propenoyl-6-O-methyl-9a-aza-9a-homoerythromycin A

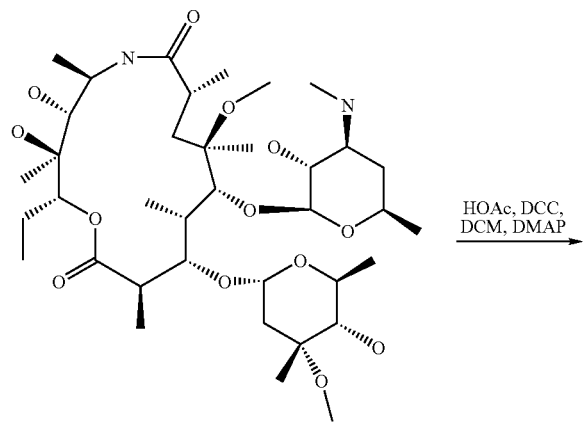

Intermediate 1, Example 4

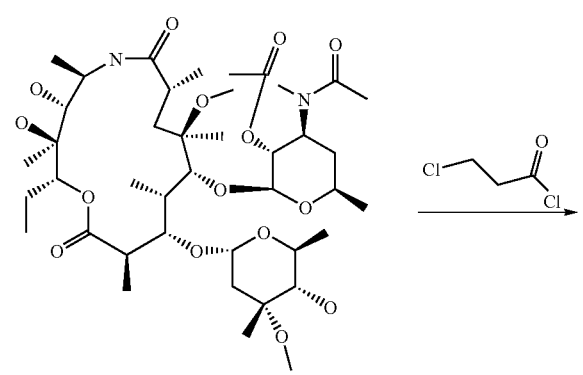

Intermediate 1, Example 45

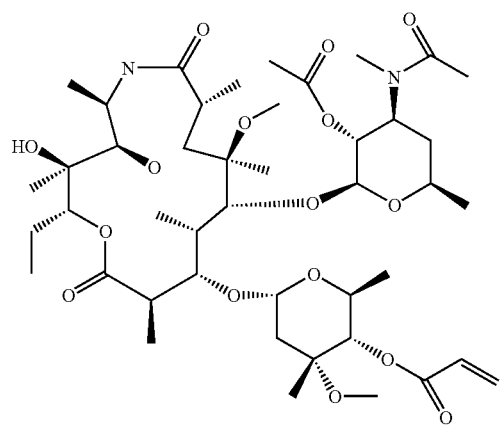

Intermediate 1 3'-N-Methyl-3'-N-2'-O-diacetyl-6-O-methyl-9a-aza-9a-homoerythromycin A Starting from intermediate 1 of Example 4 and acetic acid in the presence of DCC and DMAP in dichloromethane intermediate 1 was obtained.

3'-N-Methyl-3'-N-2'-O-diacetyl-4"-O-propenoyl-6-O-methyl-9a-aza-9a-homoerythromycin A In solution of intermediate 1 in dry toluene in the presence of TEA and 3-chloropropionyl chloride, according to the procedure described in WO 03/042228 the crude title compound was obtained.

Example 46

3'-N-Methyl-3'-N-2'-O-diacetyl-4"-O-(3-diethylamino-propionyl)-6-O-methyl-9a-aza-9a-homoerythromycin A

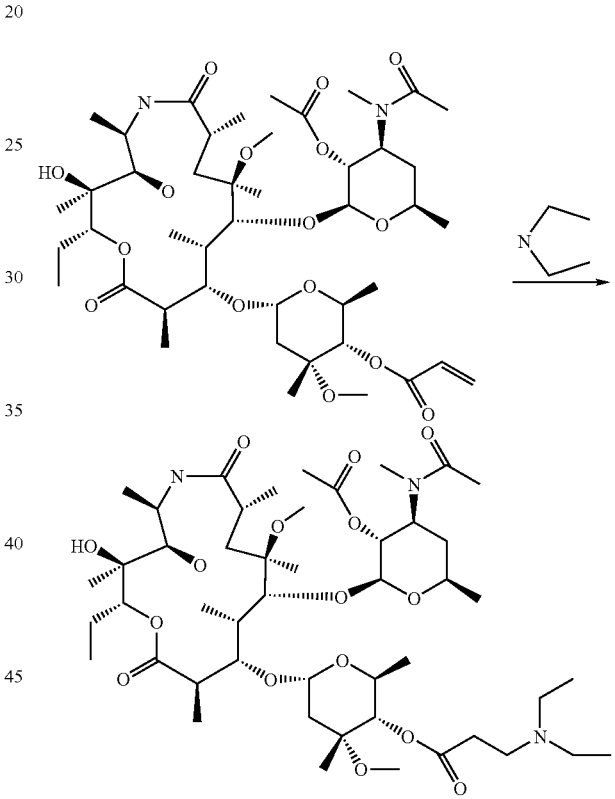

Starting from example 45 according to procedure of example 1, and after purification by column chromatography ($CH_2Cl_2$:MeOH:$NH_3$=90:9:0.5) the title compound was obtained.

MS (ES+) m/z: $[MH]^+$=960.36

Example 47

3'-N-Methyl-3'-N-(3-aminopropyl)-4"-O-(3-Diethylamino-propionyl)-6-O-methyl-9a-aza-9a-homoerythromycin A Method A The title compound was prepared according to a synthetic route as shown in Scheme below in which amount of each intermediate is specified together with molecular mass obtained by LC/MS analysis.

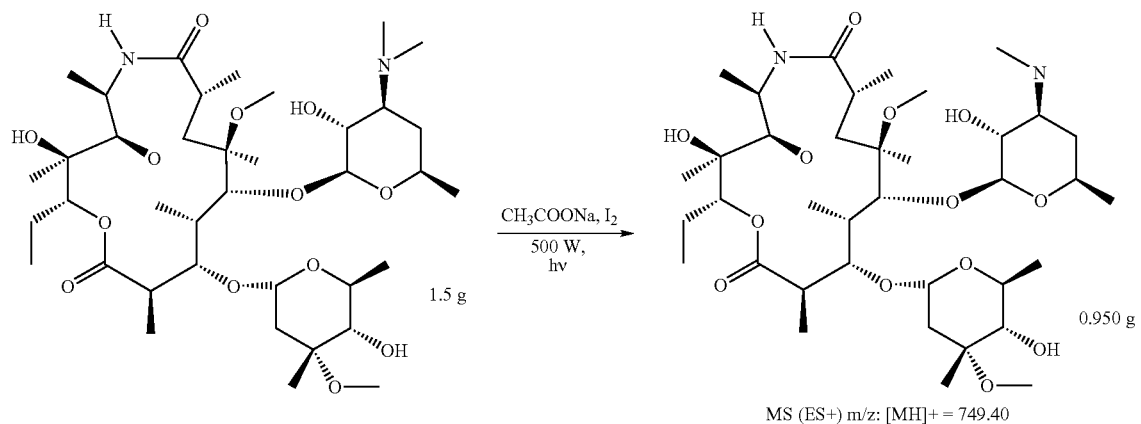
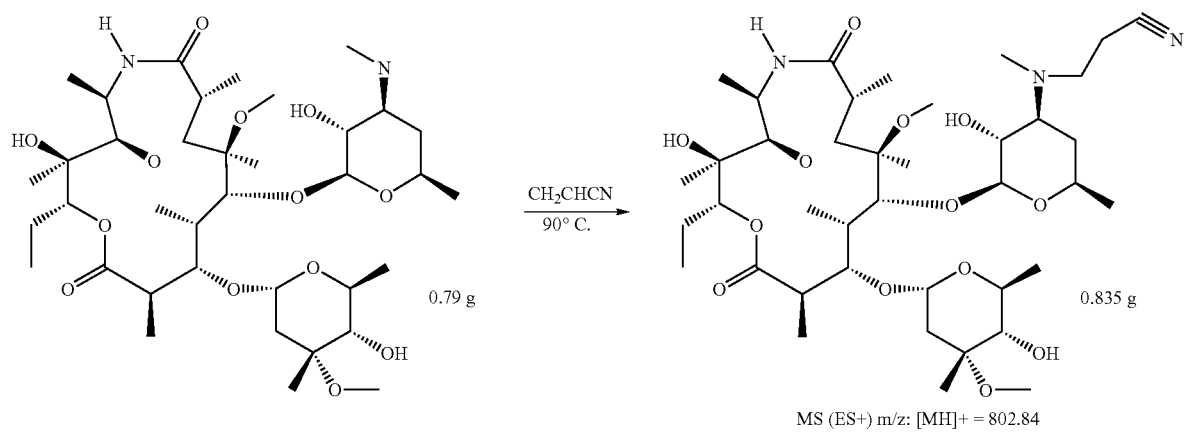
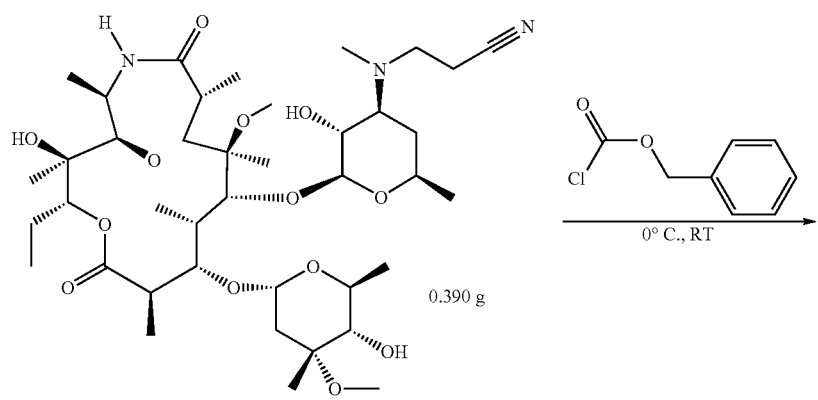

-continued
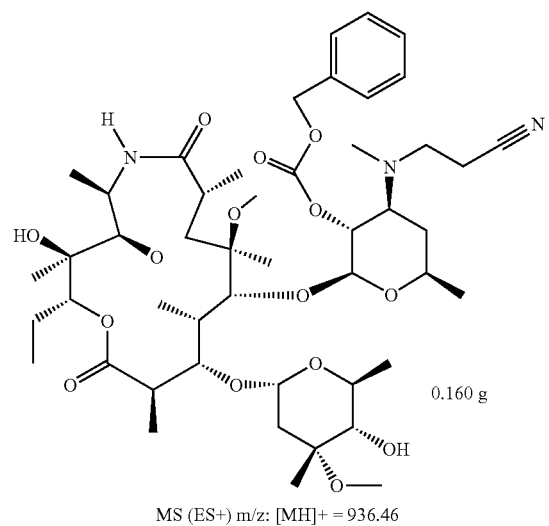
0.160 g
MS (ES+) m/z: [MH]+ = 936.46
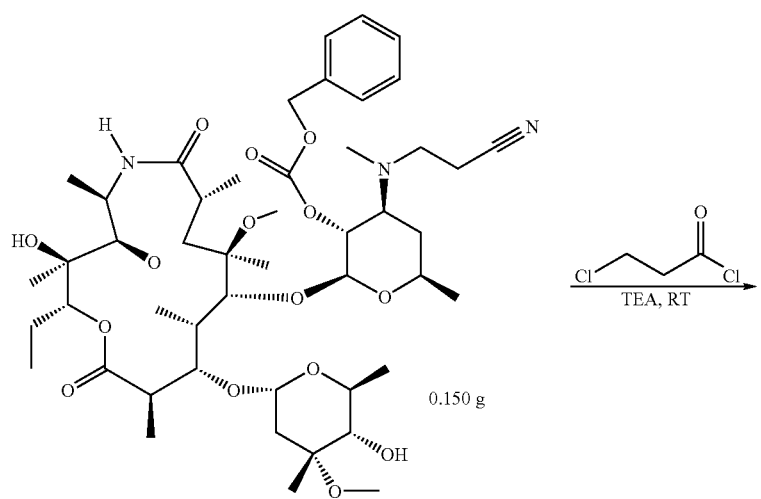
0.150 g
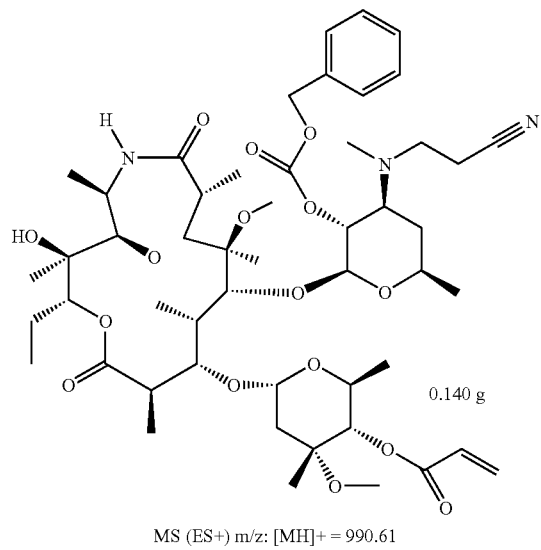
0.140 g
MS (ES+) m/z: [MH]+ = 990.61

-continued
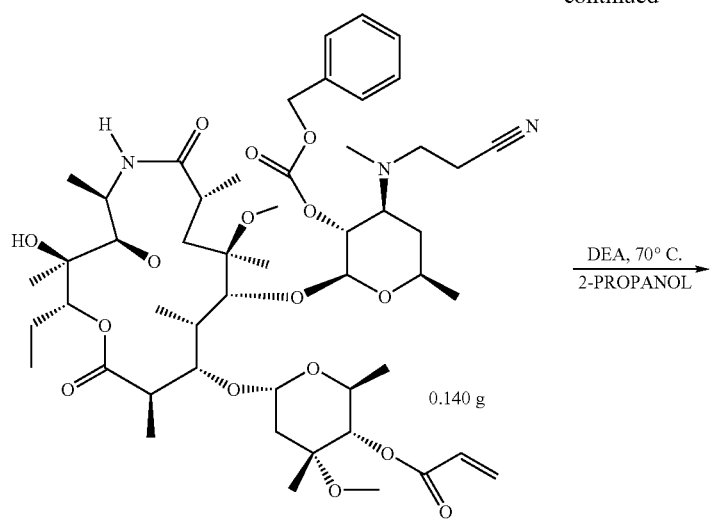
0.140 g
DEA, 70° C.
2-PROPANOL
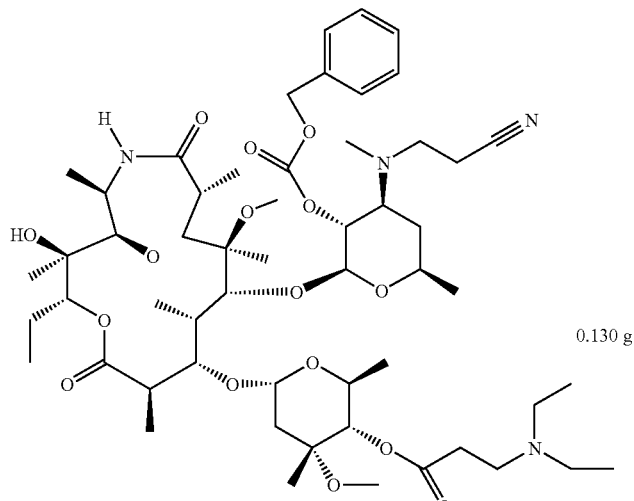
0.130 g
MS (ES+) m/z: [MH]+ = 1063.69
PtO₂, 5 bar
HOAc
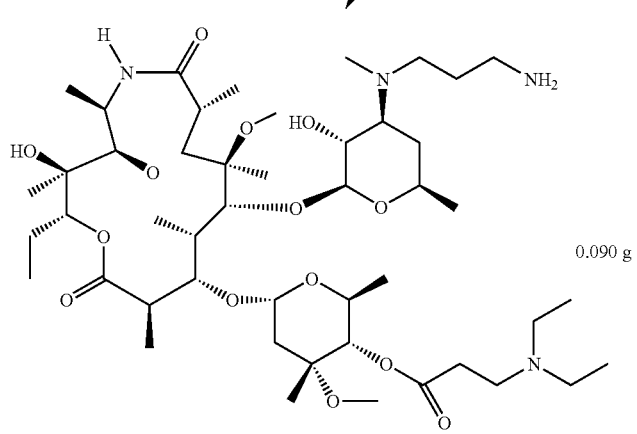
0.090 g
MS (ES+) m/z: [MH]+ = 933.74

Method B

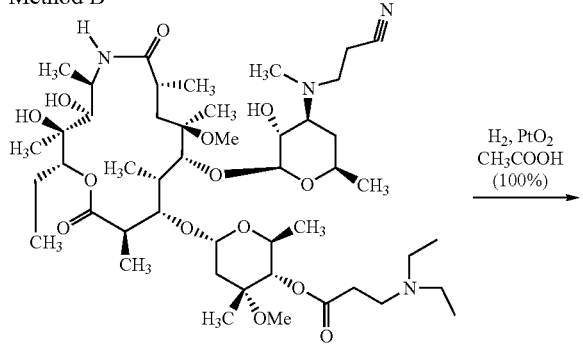

Example 61

H₂, PtO₂
CH₃COOH
(100%)

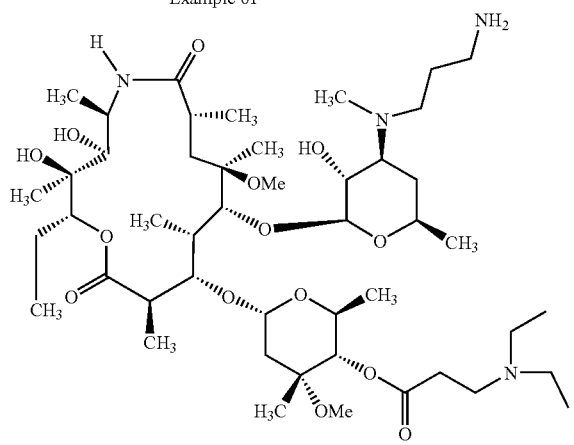

The compound of Example 61 (0.18 g, 0.19 mmol) was dissolved in glacial HOAc (10 ml) and catalyst PtO₂ (80 mg) was added. The reaction mixture was hydrogenated at 5 bar and 25° C. for 12 h. The catalyst was separated by filtration and the filtrate was poured into water (40 ml). The pH was adjusted to 8 with 10% NaOH and the mixture was extracted with EtOAc (3×30 ml). Combined organic layers where washed with saturated aqueous solution of NaHCO₃ (3×20 ml), brine (3×20 ml), water (3×20 ml) and dried over MgSO₄. After evaporation of the solvent, the crude product was purified using Flashmaster II—solid phase extraction techniques (SPE 5 g) to afford 30 mg of the title product.

MS m/z: (ES): MH⁺=933.7

Example 48

4"-O-(3-diethylamino-propionyl)-azithromycin

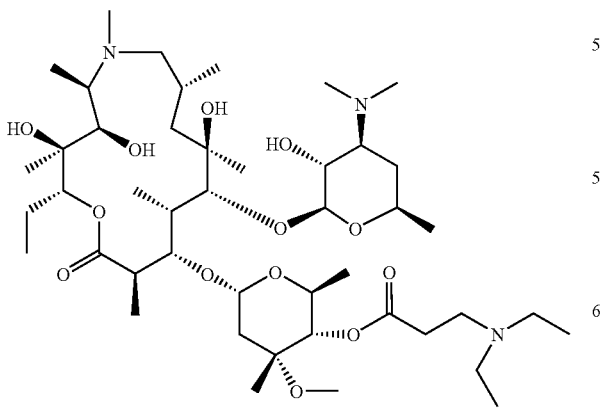

4"-O-Propenoyl-6-O-methylerithromycin (0.85 g, 1.05 mmol), obtained as described in international patent application WO 03/042228, and diethylamine (0.6 mL, 6 mmol) were dissolved in CH₃CN (20 mL) and H₂O (2 ml). The mixture was stirred overnight at 65° C. The solvents were evaporated under reduced pressure and the crude product was purified by column chromatography (DCM/MeOH/NH₄OH=90:9:0.5) to afford the title compound.

MS (ES+) m/z: [MH]⁺=877.1

Example 49

4"-O-(3-Diethylamino-propionyl)-6-O-methylerithromycin A

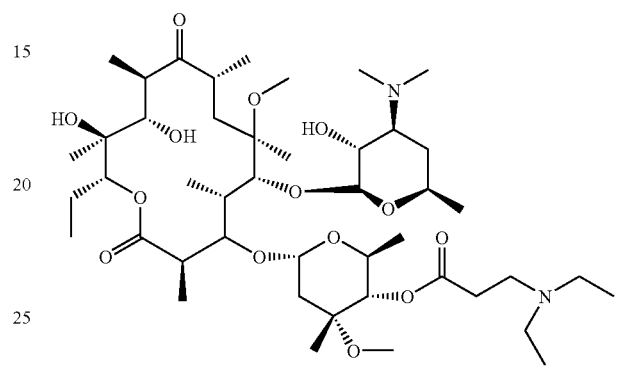

4"-O-Propenoyl-6-O-methylerythromycin (1.0 g, 1.2 mmol), obtained as described in international patent application WO 03/042228 and diethylamine (0.6 mL, 6 mmol) were dissolved in CH₃CN (20 mL) and H₂O (2 ml). The mixture was stirred overnight at 60° C. The solvents were evaporated under reduced pressure and the crude product was purified by column chromatography (DCM/MeOH/NH₄OH=90:9:0.5) to afford the title compound.

MS (ES+) m/z: [MH]⁺=876.0

Example 50

4"-O-(3-piperazin-1-yl-propionyl)-6-O-methylerithromycin A

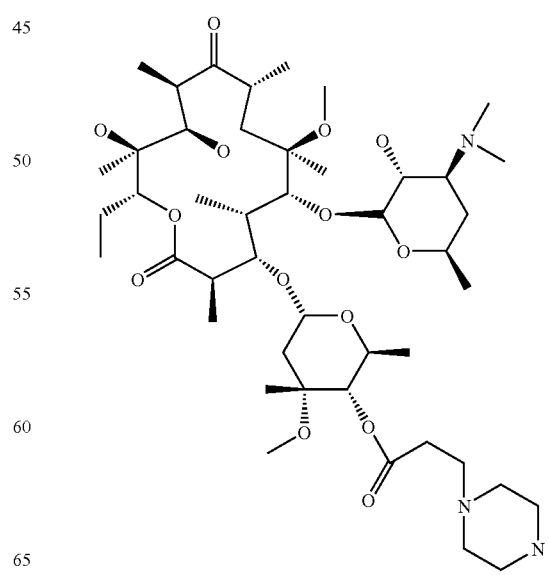

To a solution of 4"-O-propenoyl-6-O-methylerithromycin (1.0 g), obtained as described in international patent application WO 03/042228, in acetonitrile (10 ml) were added piperazine (0.431 g, 5 mmol), water (1.14 ml) and triethylamine (0.455 ml) and suspension was heated to 80° C. for 2 hours. The solvent was evaporated and the residue was extracted with EtOAc and water (2×50 ml). Organic layer was washed with brine and NaHCO$_3$ (2×50 ml). The organic layer was dried over K$_2$CO$_3$ and evaporated in vacuum yielding the title product (1.0 g).

MS (ES+) m/z: [MH]$^+$=889.9

Examples 51A to C

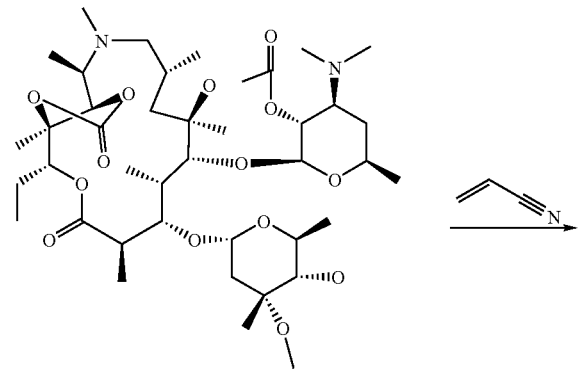

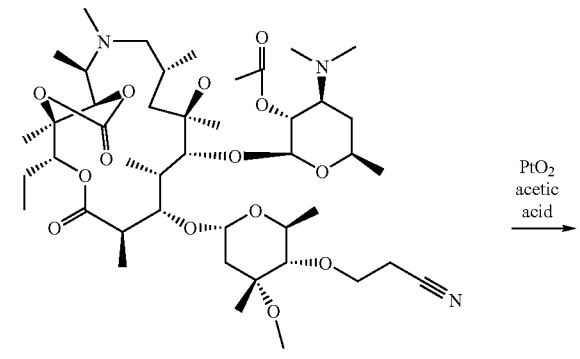

Example 51A

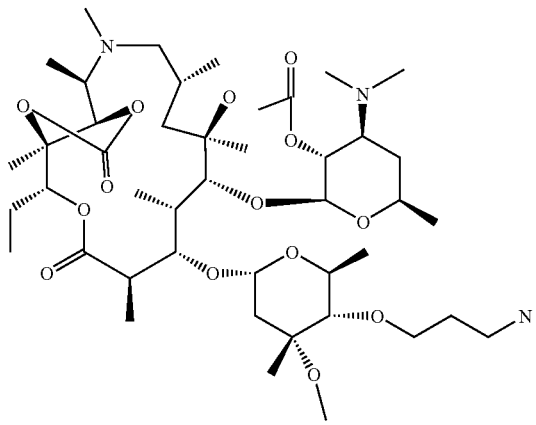

Example 51B

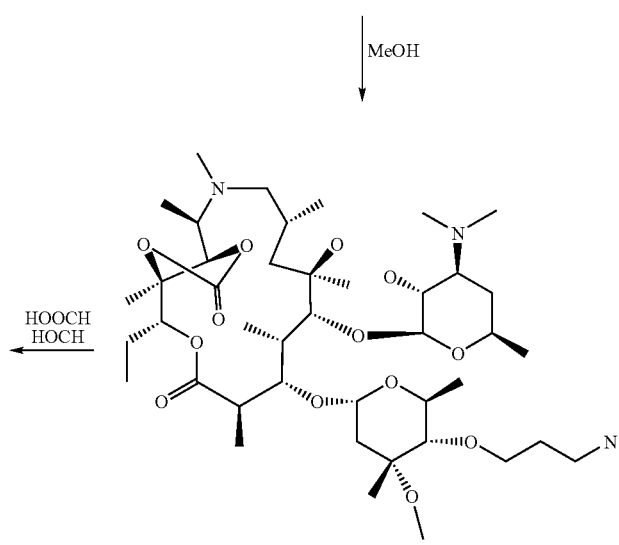

Example 51C

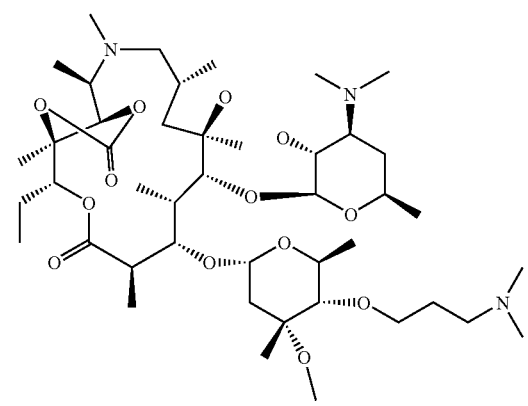

Example 52

Example 51A

11,12-Carbonate-11,12-dideoxy-2'-O-acetyl-4"-O-(2-cyanoethyl)-azithromycin

2'-O-Acetyl-11,12-carbonate-11,12-dideoxy-azithromycin (10 g, 12 mmol), obtained as described in international patent application WO 03/042228, was dissolved in acrylonitrile (100 ml) in $N_2$ atmosphere. t-BuOH (3.75 ml, 5.8 mmol) was added and the reaction mixture was cooled in an ice bath (0° C.). NaH (0.3 g, 12 mmol) was added in portions during 10 minutes and the reaction mixture was stirred overnight at room temperature. Acrylonitrile was evaporated under reduced pressure. To the residue EtOAc (250 ml) was added, extracted with water (150 ml). Water layer was washed with EtOAc (100 ml). Combined organic layers were washed with water (200 ml), dried over $K_2CO_3$ and evaporated under reduced pressure yielding 10.5 g of the Intermediate 1 which was used in the next step without purification.

MS; m/z (ES): 870.1 [MH]$^+$

Example 51B

11,12-Carbonate-11,12-dideoxy-2'-O-acetyl-4"-O-(3-aminopropyl)-azithromycin

A high pressure reactor was filled with solution of Intermediate 1 from Example 51A (5 g, 5.7 mmol) in acetic acid (150 ml). $PtO_2$ (1.6 g) was added and the reaction mixture was stirred at 5 bar overnight. Catalyst was filtered through cellite and solvent evaporated in vacuum yielding 12 g of crude the product, which was used in the next step without purification.

MS; m/z (ES): 874 [MH]$^+$

Example 51C

11,12-Carbonate-11,12-dideoxy-4"-O-(3-aminopropyl)-azithromycin

Example 51B was dissolved in MeOH (250 ml) and stirred at 55° C. for 24 hours (pH of the reaction mixture was adjusted to 8 with $NH_3/H_2O$=1/1). The solvent was evaporated under reduced pressure and to the residue DCM (50 ml) and water (50 ml) were added and pH was adjusted to 6 with 0.25M HCl. Layers were separated and organic layer was evaporated yielding 3 g of crude product that was purified by column chromatography (fraction, DCM:MeOH:$NH_3$=90:15:1.5) yielding 2.5 g of the title compound.

MS; m/z (ES): 832.1 [MH]$^+$

Example 52

11,12-Carbonate-11,12-dideoxy-4"-O-(3-dimethylamino-propyl)-azithromycin

To a solution of the compound of Example 51C (0.10 g, 0.12 mmol) in acetone (10 mL) formaldehyde (37 wt % solution in water) (0.05 mL, 6 mmol) and formic acid (0.055 mL, 1.5 mmol) were added. The reaction mixture was stirred for 4 hours at 40° C. Acetone was evaporated under reduced pressure and the crude product was purified by column chromatography (silica, 90/9/1.5 $CH_2Cl_2$/MeOH/$NH_4OH$ eluent) to afford the title compound as a white solid.

MS; m/z (ES): 860.54 [MH]$^+$.

Example 53

3'-N-Demethyl-4"-O-acryloyl-6-O-methyl-9a-aza-9a-homoerythromycin A

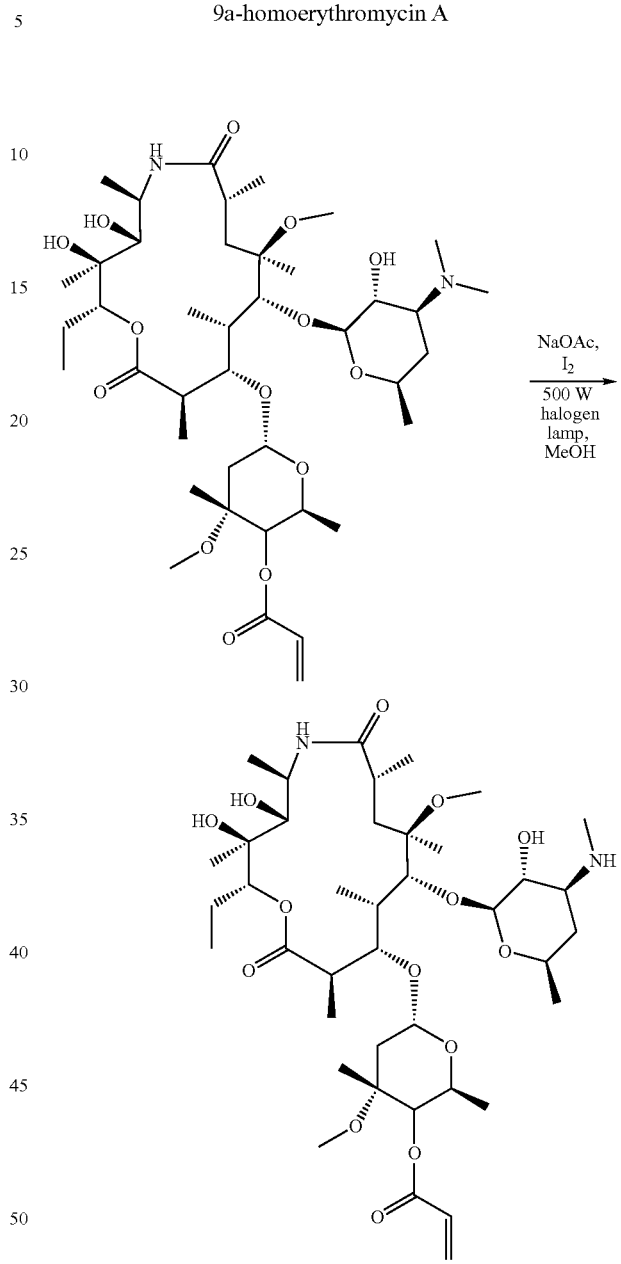

To a stirred solution of 4"-O-acryloyl-6-O-methyl-9a-aza-9a-homoerythromycin A (0.5 g, 0.61 mmol), obtained as described in international application WO 03/042228 intermediate 43, and sodium acetate trihydrate (0.23 g, 2.8 mmol) in methanol (12.5 ml), solid iodine (0.155 g, 0.61 mmol) was added. The reaction mixture was irradiated with a 500 W halogen lamp for 2 h, cooled to room temperature and the solvent was evaporated. Solid residue was dissolved in ethyl acetate (100 ml), filtered, and the filtrate was washed with saturated $NaHCO_3$ (25 ml) and saturated NaCl (25 ml). The organic layer was dried over $Na_2SO_4$ and evaporated to give 0.4 g of the title compound.

MS (ES+) m/z: [MH]$^+$=803.4

$^{13}$C NMR (125 MHz., CDCl$_3$) δ: 179.6, 177.5, 131.6, 128.1, 101.5, 95.5, 79.4, 78.8, 78.5, 78.4, 76.0, 74.9, 74.3, 72.9, 72.8, 67.5, 63.3, 59.9, 51.5, 49.5, 45.4, 44.5, 41.2, 40.1, 37.7, 35.8, 35.1, 33.2, 21.6, 21.1, 20.8, 20.6, 19.6, 18.2, 16.2, 15.2, 14.0, 11.2, 9.8.

Example 54

3'-N-Demethyl-4"-O-(3-diethylaminopropionyl)-6-O-methyl-9a-aza-9a-homoerythromycin A

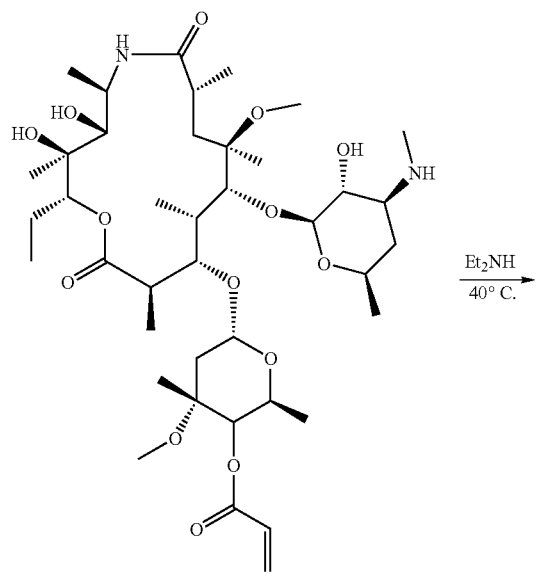
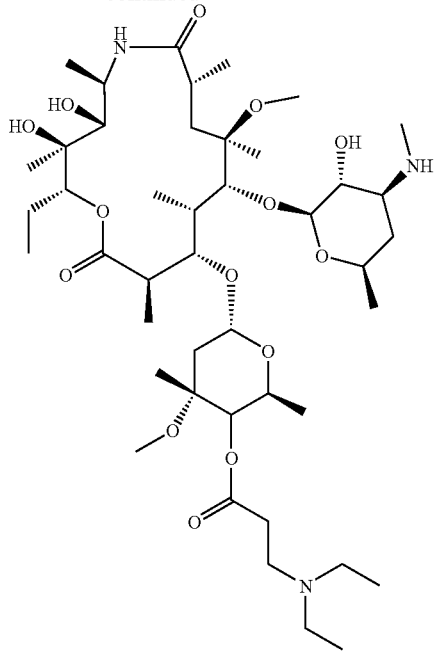

A solution of the compound of Example 53 (0.2 g, 0.25 mmol) in diethyl amine (5 ml) was heated at 40° C. overnight, cooled to r.t, and evaporated to dryness. The residue was purified by flash chromatography (hexane/ethylacetate/diethylamine=1:1:0.2) to afford 0.21 g of the title compound.

MS (ES+) m/z: [MH]$^+$=876.5

$^{13}$C NMR (125 MHz, CDCl$_3$) δ: 179.2, 177.1, 101.0, 95.1, 78.9, 78.1, 78.0, 77.9, 75.6, 74.5, 73.9, 72.5, 72.4, 67.0, 62.7, 59.5, 51.1, 49.0, 48.1, 46.3, 45.0, 44.1, 40.8, 39.7, 36.9, 35.4, 34.6, 32.7, 32.3, 21.2, 20.7, 20.3, 20.2, 19.2, 17.8, 15.8, 14.7, 13.5, 11.3, 10.7, 9.3.

Example 55

4"-O-(4-Diethylaminobutanoyl)-6-O-methyl-9a-aza-9a-homoerythromycin A

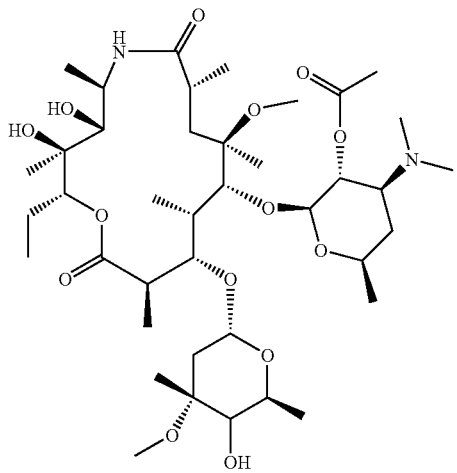
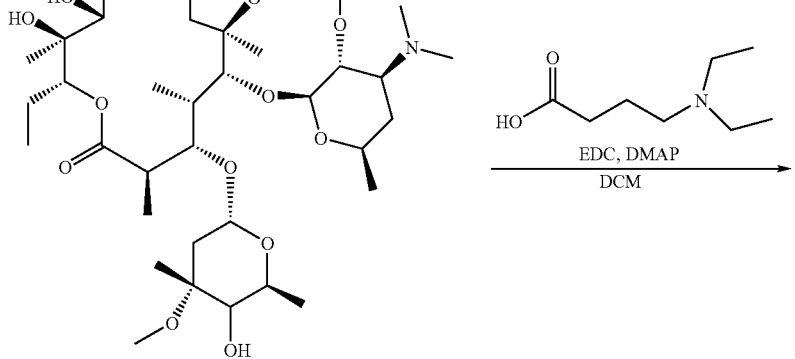

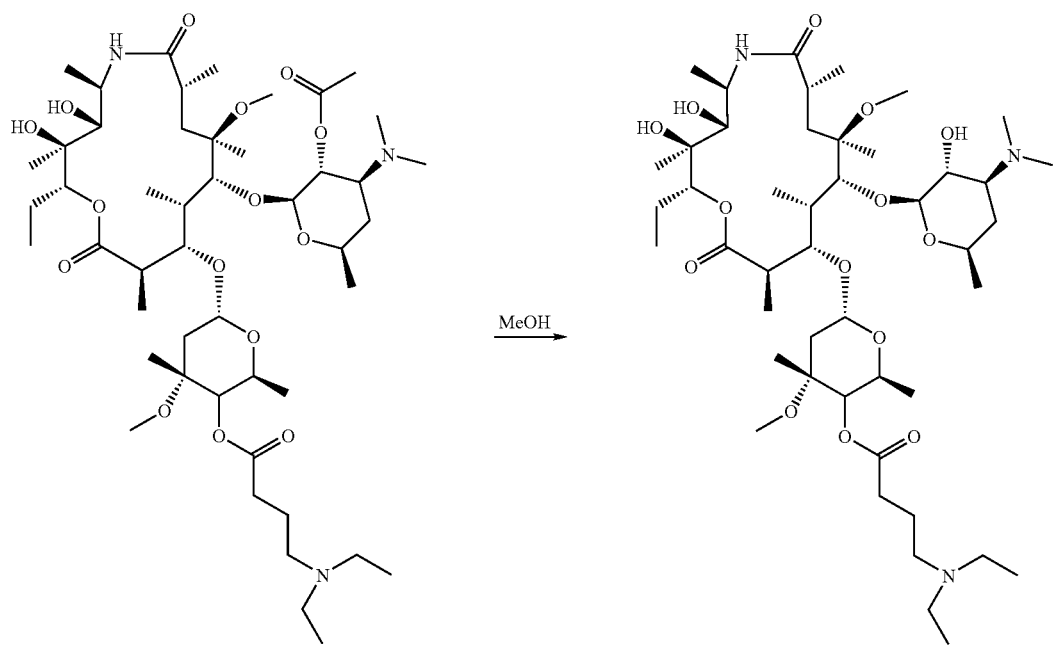

A solution of 2'-O-acetyl-6-O-methyl-9a-aza-9a-homoerithromycin (0.8 g, 1 mmol) obtained according to procedure described in internationale patent application WO 03/042228, intermediate 41, diethylaminobutyric acid (0.83 g, 5.22 mmol), EDC×HCl (2 g, 10 mmol), DMAP (1.2 g, 10 mmol) in dichloromethane (10 ml) was stirred overnight at r.t. Solvent was evaporated, the residue dissolved in methanol (25 ml), and stirred at r.t. for 48 h. Methanol was evaporated and the crude product purified using Flashmaster II—solid phase extraction technique (SPE 10 g, DCM/MeOH/ NH$_4$OH=90:5:0.5 as eluent) to afford 0.24 g of the title product.

MS m/z: (ES): MH$^+$=904.9

Example 56

4"-O-(2-Diethylaminoethanoyl)-6-O-methyl-9a-aza-9a-homoerythromycin A

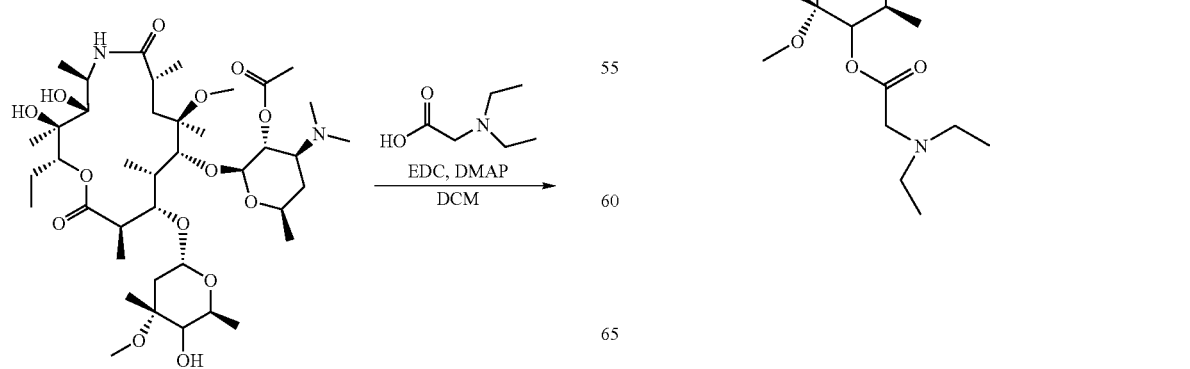

-continued

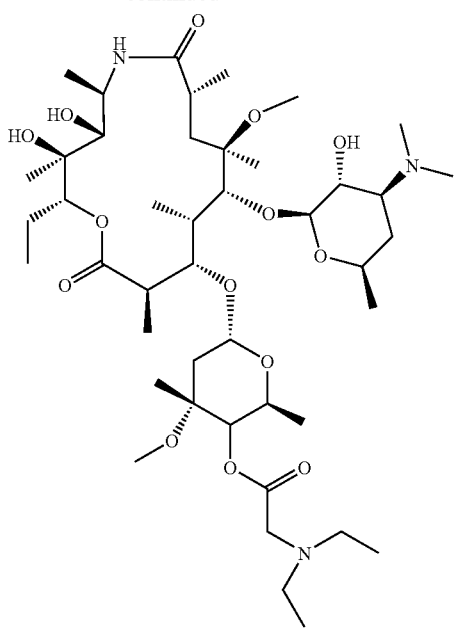

A solution of 2'-O-acetyl-6-O-methyl-9a-aza-9a-homoerithromycin (0.5 g, 0.62 mmol), diethylaminoacetic acid (0.49 g, 3.72 mmol), EDC×HCl (0.74 g, 3.72 mmol), DMAP (0.45 g, 3.72 mmol) in dichloromethane (10 ml) was stirred overnight at r.t. Solvent was evaporated, the residue dissolved in methanol (25 ml), and stirred at r.t. for 48 h. Methanol was evaporated and the crude product purified using Flashmaster II—solid phase extraction technique (SPE 10 g, DCM/MeOH/NH$_4$OH=90:5:0.5 as eluent) to afford 0.27 g of the title product.

MS m/z: (ES): MH$^+$=876.4

Example 57

3'-N-methyl-3'-N-1-propyl-4"-O-(3-diethylaminopropionyl)-6-O-methyl-9a-aza-9a-homoerythromycin A

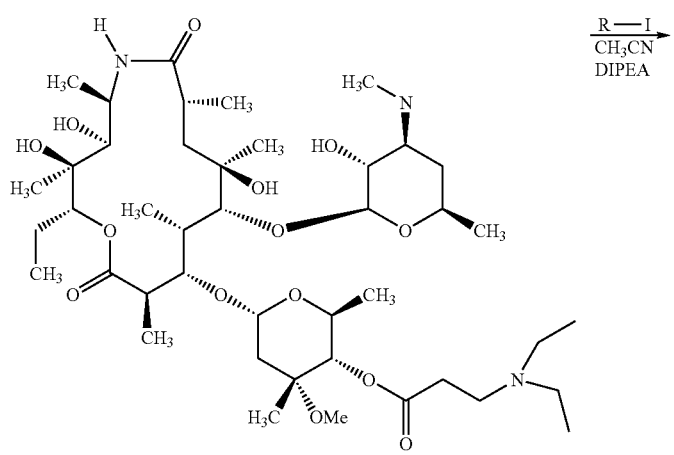

Example 54

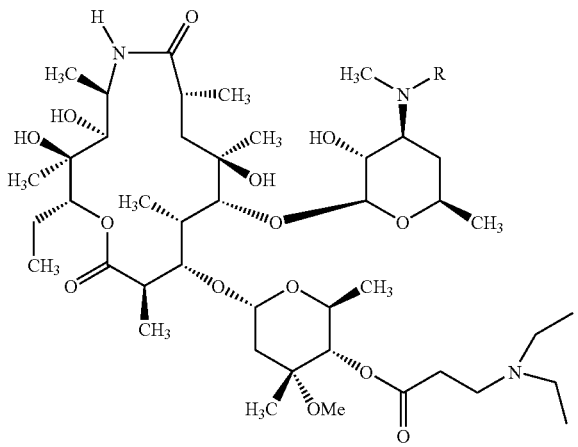

-continued

| Product | R | MS (ES, m/z) | purity % | yield % |
|---|---|---|---|---|
| Example 57 | (isopropyl) | 918.7 [M + H]+, calculated 918.2 | 98.8 | 40.1 |
| Example 58 | (n-propyl) | 904.7 [M + H]+, calculated 904.2 | 95.1 | 42.9 |
| Example 59 | (n-pentyl) | 932.7 [M + H]+, calculated 932.2 | 99.3 | 40.9 |
| Example 60 | (isobutyl) | 918.8 [M + H]+, calculated 918.2 | 98.6 | 32.9 |

To the solution of the compound from Example 54 (0.05 g, 0.057 mmol) in $CH_3CN$ (4.0 ml), DIPEA (101 μl, 0.570) and i-propyliodide (0.2 g, 1.14 mmol) were added. The reaction mixture was stirred for 24 h at 65° C. After evaporation of the solvent, the crude product was purified using Flashmaster II—solid phase extraction technique (SPE 5 g) to afford 21.0 mg (40.1%) of the title product.

Examples 58 to 60

General Procedure for 3'-N-alkylation

To the solution of compound from Example 54 (0.10 g, 0.114 mmol) in $CH_3CN$ (4.0 ml), DIPEA (25.4 μl, 0.142), and alkyl-iodide (0.28 mmol) were added. The reaction mixture was stirred for 24 h at room temperature. After evaporation of the solvent, the crude product was purified using Flashmaster II—solid phase extraction technique (SPE 5 g).

Example 61

3'-N-methyl-3'-N-(2-cyanoethyl)-4''-O-(3-diethylaminopropionyl)-6-β-methyl-9a-aza-9a-homoeritromicin A

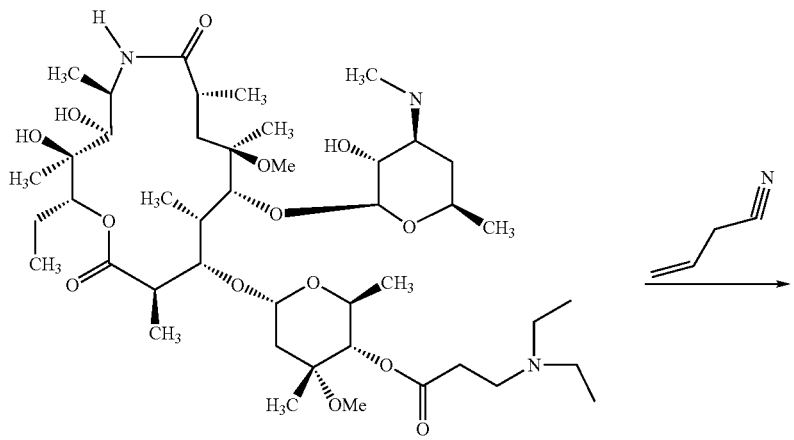

Example 54

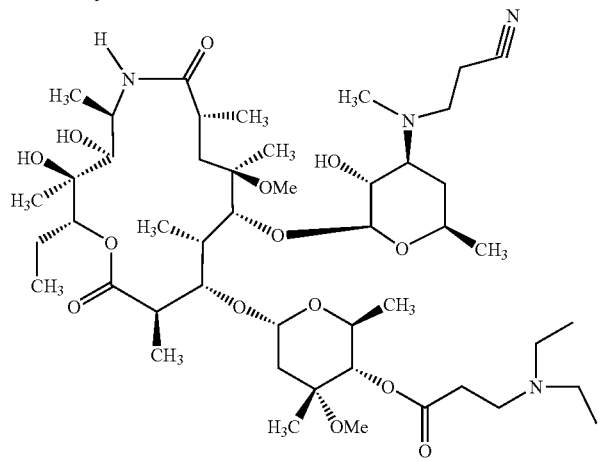

Compound from Example 54 (0.20 g, 0.068 mmol) was dissolved in acrylonitrile (5 ml). The reaction mixture was stirred for 24 h at 60° C. After evaporation of the solvent, the crude product was purified using Flashmaster II—solid phase extraction techniques (SPE 5 g). to afford 180 mg of the title product.

MS m/z: (ES): MH$^+$=929.2

Example 62

3'-N-methyl-3'-N-acetyl-4''-O-(3-diethylaminopropionyl)-6-O-methyl-9a-aza-9a-homoerythromycin A

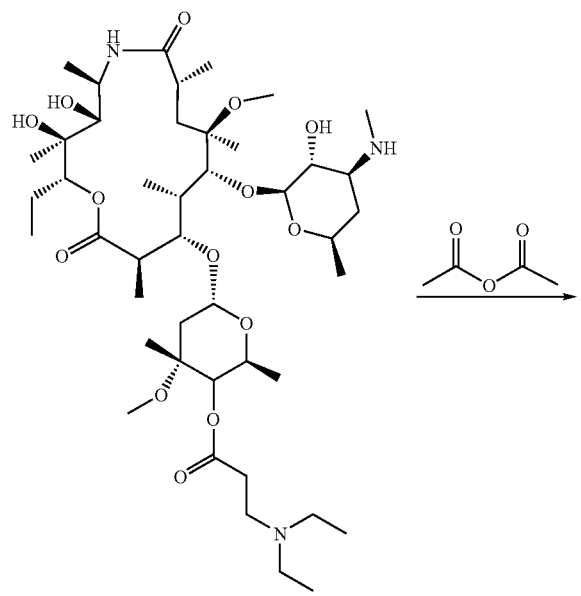

Example 54

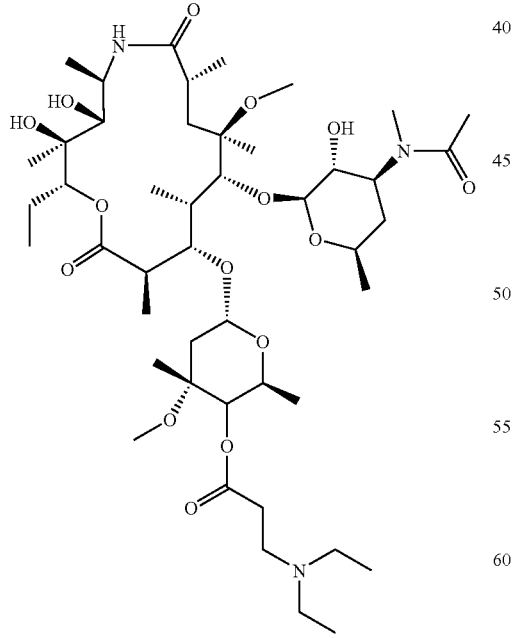

A solution of compound from Example 54 (0.43 g, 0.49 mmol), acetic anhydride (48 μl, 0.51 mmol) and triethylamine (70 μl, 0.25 mmol) in DCM (8 ml) was stirred for 2 h at room temperature. The reaction mixture was diluted with DCM (150 ml), washed with saturated aqueous NaHCO$_3$ solution and brine, than dried over Na$_2$SO$_4$. The product was purified using Flash-Si SPE (flashmaster, 70 ml) and ethyl acetate/hexane/diethylamine=5:5:1 as eluent to afford 0.32 g of the title product.

MS (ES+) m/z: [MH]$^+$=918.7

Example 63

3'-N-methyl-3'-N-propionyl-4''-O-(3-diethylaminopropionyl)-6-O-methyl-9a-aza-9a-homoerythromycin A

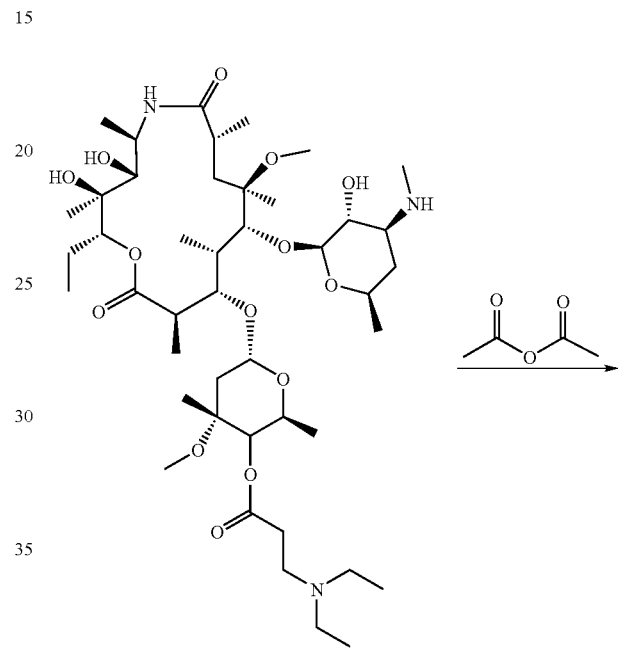

Example 54

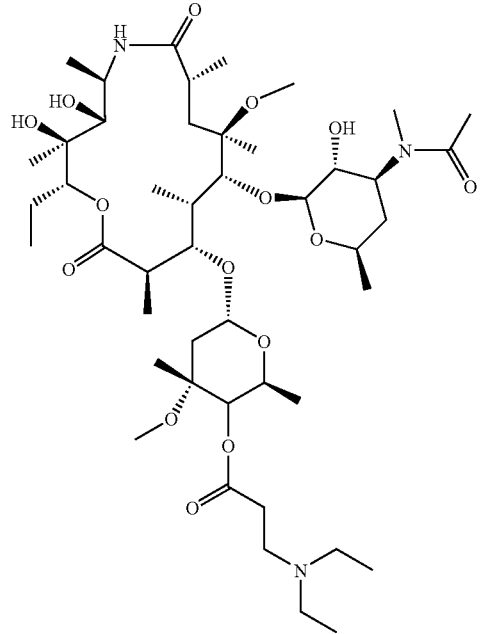

A solution of compound from Example 54 (0.1 g, 0.11 mmol), propionic anhydride (15 μl, 0.11 mmol), and triethylamine (16 μl, 0.11 mmol) in DCM (3 ml) was stirred for 2 h at room temperature. The reaction mixture was diluted with DCM (150 ml), washed with saturated aqueous NaHCO₃ solution and brine, than dried over Na₂SO₄. The product was purified using Flash-Si SPE (flashmaster, 70 ml) and ethyl acetate/hexane/diethylamine=5:5:1 as eluent to afford 0.07 g of the title product.

MS (ES+) m/z: [MH]⁺=932.7

Example 64

11,12-carbonate-11,12-dideoxy-2'-O-acetyl-4''-O-(3-diethylaminopropyl)-6-O-methylerythromycin A 9-oxime Intermediate 1: 11,12-carbonate-11,12-dideoxy-2'-O-acetyl-4''-O-(2-cyanoethoxy)-6-O-methylerythromycin A 9-[O-(2-chlorobenzyl)]oxime A solution of 11,12-carbonate-11,12-dideoxy-2'-O-acetyl-6-O-methylerythromycin A 9-[O-(2-chlorobenzyl)]oxime (1.0 g, 1.05 mmol), t-BuOH (0.303 ml, 3.15 mmol) and NaH (46.2 mg, 1.15 mmol) in acrylonitrile (22 ml) was stirred for 6 h at 0° C. and then allowed to warm up to room temperature. Acrylonitrile was evaporated, the residue dissolved in ethyl acetate, and filtrated off. The filtrate was washed with water (3×20 ml) and brine (3×20 ml), and dried over K₂CO₃. Evaporation of the solvent afforded 1.49 g of the title product.

MS (ES+) m/z: [MH]⁺=1008.4

Intermediate 2: 11,12-carbonate-11,12-dideoxy-2'-O-acetyl-4''-O-(3-aminopropyl)-6-O-methylerythromycin A 9-[O-(2-chlorobenzyl)]oxime

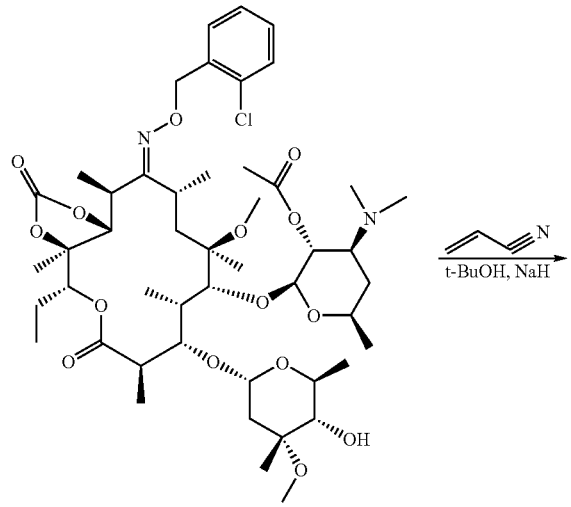

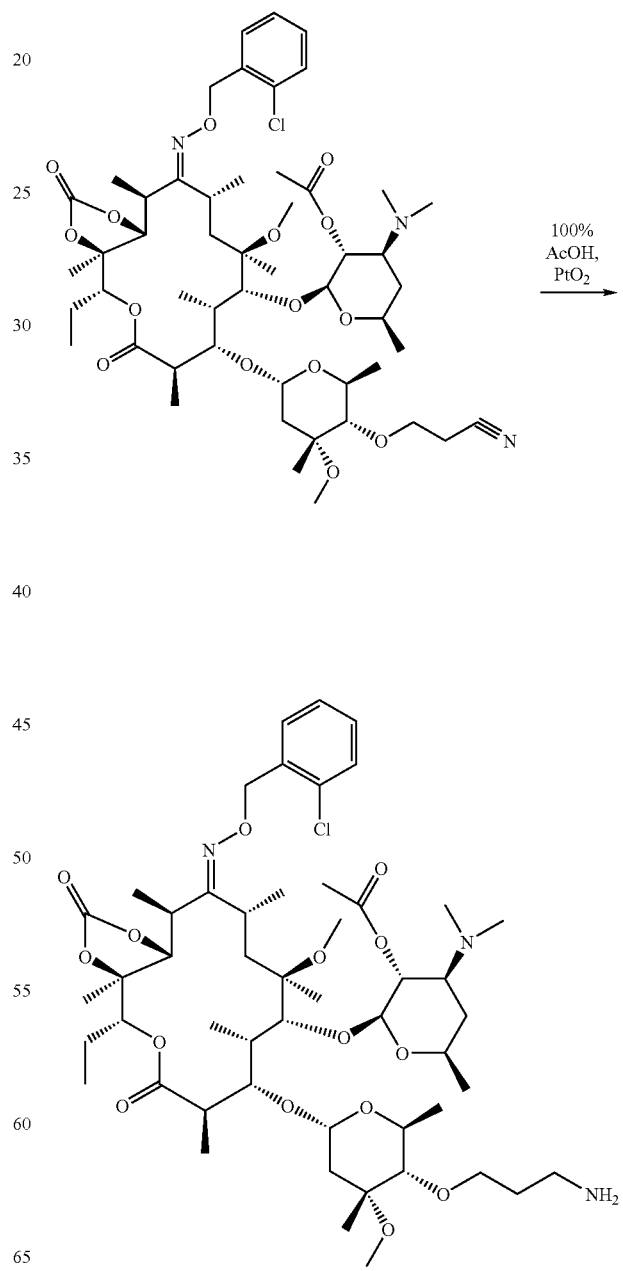

A suspension of Intermediate 1 (1.49 g, 1.48 mmol) and PtO$_2$ (250 mg) in glacial HOAc (50 ml) was hydrogenated at 5 bar overnight. The reaction mixture was filtrated, acetic acid evaporated, the residue dissolved in DCM (30 ml) and H$_2$O (30 ml) and pH adjusted to 9.4. Layers were separated, water layer extracted with DCM (2×30 ml) and combined organic layers were dried over K$_2$CO$_3$. Evaporation of DCM afforded 0.98 g of the title product.

MS (ES+) m/z: [MH]$^+$=1012.5

Intermediate 3: 11,12-carbonate-11,12-dideoxy-2'-O-acetyl-4''-O-(3-diethylaminopropyl)-6-O-methyl-erythromycin A 9-[O-(2-chlorobenzyl)]oxime

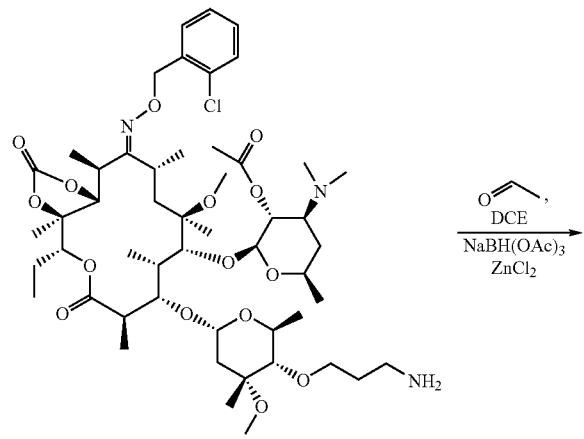

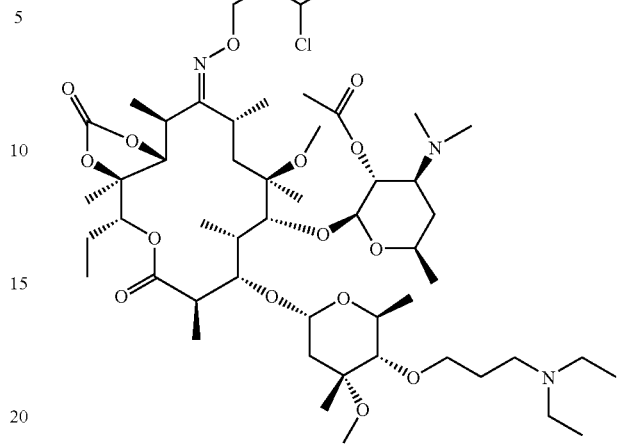

A solution of Intermediate 2 (0.4 g, 0.4 mmol), acetaldehyde (66.7 μl, 1.19 mmol), NaBH(OAc)$_3$ (0.25 g, 1.19 mmol) and ZnCl$_2$ (54 mg, 0.4 mmol) in dichloroethane (20 ml) was stirred at r.t. for 4 h. Reaction mixture was filtered, dichloroethane evaporated, the residue dissolved in DCM (20 ml) and H$_2$O (20 ml), pH adjusted to 9.3, layers were separated, and water layer was extracted with DCM (2×15 ml) and combined organic layers were dried over K$_2$CO$_3$. Evaporation of DCM afforded 0.37 g of the title product.

MS (ES+) m/z: [MH]$^+$=1068.4

11,12-carbonate-11,12-dideoxy-2'-O-acetyl-4''-O-(3-diethylaminopropyl)-6-O-methylerythromycin A 9-oxime

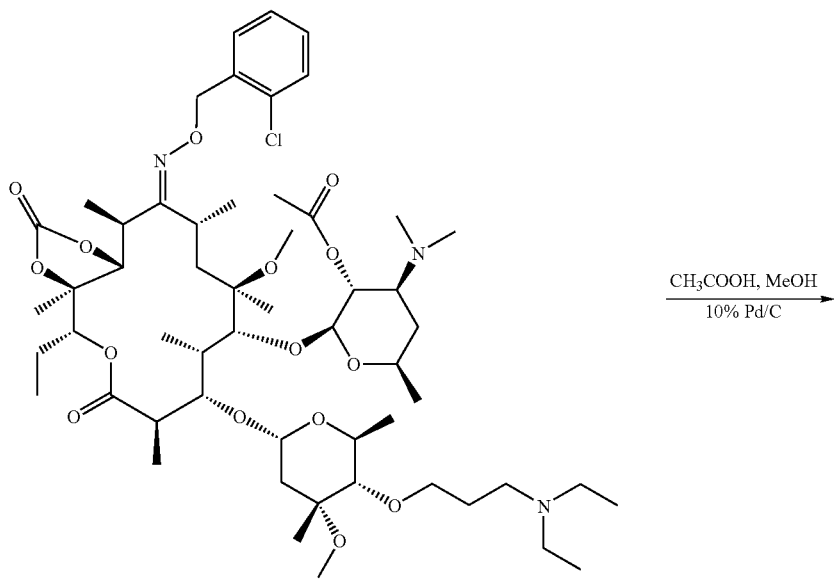

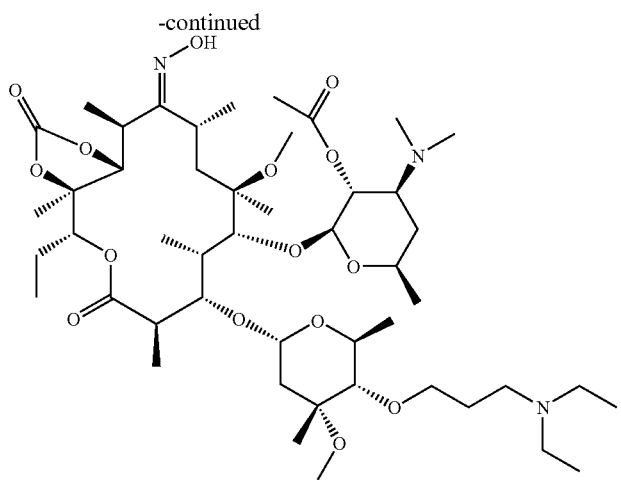

A suspension of Intermediate 3 (0.37 g, 0.35 mmol), glacial HOAc (100 μl, 1.75 mmol) and 10% Pd/C (150 mg) in MeOH (40 ml) was hydrogenated at 5 bar overnight. The reaction mixture was filtrated, pH adjusted to 5.5, fresh 10% Pd/C (185 mg) was added and the reaction mixture hydrogenated at 70 bar for 3 days. The catalyst was filtered off, solvent evaporated, the residue dissolved in DCM (30 ml) and H$_2$O (30 ml), pH adjusted to 9.4, layers separated, water layer extracted with DCM (2×30 ml) and combined organic layers dried over K$_2$CO$_3$. Evaporation of DCM afforded 0.18 g of the title product.

MS (ES+) m/z: [MH]$^+$=944.9

Example 65

4"-O-(3-diethylaminopropyl)-6-O-methylerythromycin A 9-oxime

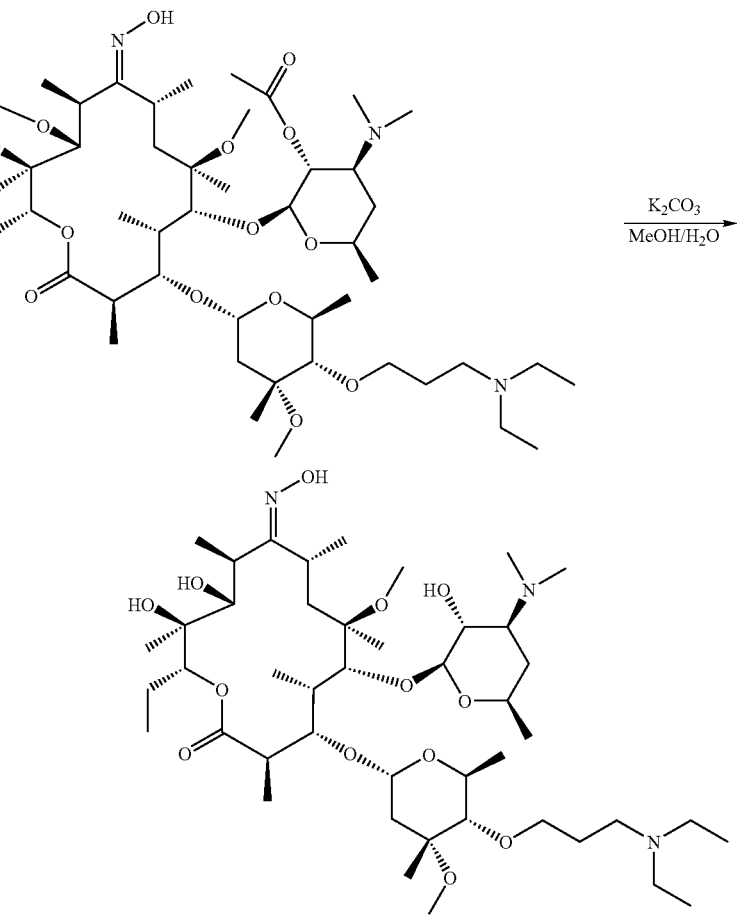

A solution of the compounds of Example 64 (0.18 g, 0.19 mmol) and K$_2$CO$_3$ (0.45 g, 3.25 mmol) in MeOH (15 ml) and H$_2$O (5 ml) was stirred overnight at 50° C. Methanol was evaporated, ethyl acetate (20 ml) and H$_2$O (10 ml) were added. Layers were separated and organic layer dried over K$_2$CO$_3$. Evaporation of the solvent afforded 0.167 g of the crude title product which was purified using column chromatography on silica gel (DCM/MeOH/NH$_4$OH 90:9:0.5 as eluent) to obtain 90 mg of the title product.

MS (ES+) m/z: [MH]$^+$ 877.0

Example 66

4"-O-(3-diethylaminopropyl)-6-O-methylerythromycin A

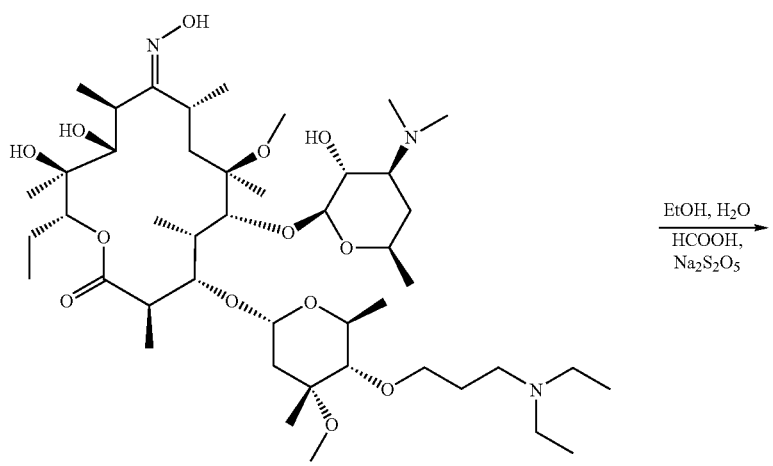

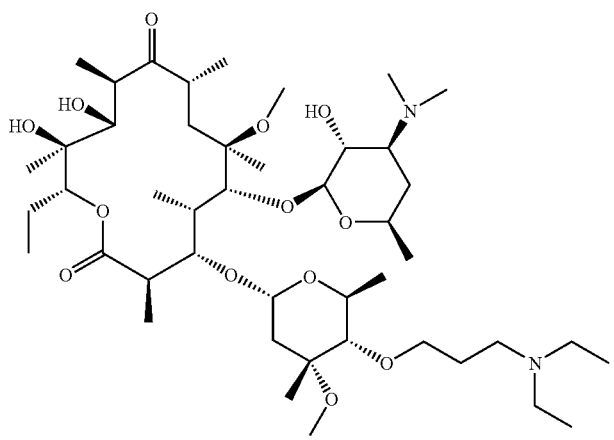

To a solution of the compound of Example 65 (50 mg, 0.06 mmol) and HCOOH (6.3 µl, 0.168 mmol) in EtOH (0.7 ml) and H$_2$O (0.7 ml), Na$_2$S$_2$O$_5$ (46 mg, 0.12 mmol) was added at r.t. The reaction mixture was warmed up to 80° C. and second portion of Na$_2$S$_2$O$_5$ (46 mg, 0.12 mmol) was added and stirred for further 4 h at 80° C. Ethanol was evaporated, the residue diluted with DCM (25 ml) and water (25 ml), pH adjusted to 9.3, layers separated, and water layer extracted with DCM (2×10 ml). Combined organic layers were dried over K$_2$CO$_3$. Evaporation of DCM afforded 0.18 g of the title product.

MS (ES+) m/z: [MH]$^+$=861.5

Example 67

11,12-carbonate-11,12-dideoxy-2'-O-acetyl-4''-O-(3-aminopropyl)-6-O-methylerythromycin A 9-[O-(1-isopropoxycyclohexyl)]oxime Intermediate 11,12-carbonate-11,12-dideoxy-2'-O-acetyl-4''-O-(2-cyanoethyl)-6-β-methylerythromycin A 9-[O-(1-isopropoxycyclohexyl)]oxime A solution of 11,12-carbonate-11,12-dideoxy-2'-O-acetyl-6-O-methylerythromycin A 9-[O-(1-isopropoxycyclohexyl)]oxime (1.7 g, 1.75 mmol), t-BuOH (0.505 ml, 5.25 mmol) and NaH (77 mg, 1.925 mmol) in acrylonitrile (36.6 ml) was stirred for 6 h at 0° C., allowed to warm up to room temperature and further stirred overnight. After evaporation of acrylonitrile the residue was dissolved in ethyl acetate and filtrated off. Obtained filtrate was washed with water (3×20 ml) and brine (3×20 ml) and dried over K$_2$CO$_3$. Evaporation of the solvent afforded 2.07 g of the title product.

MS (ES+) m/z: [MH]$^+$=1024.9

11,12-carbonate-11,12-dideoxy-2'-O-acetyl-4'-O-(3-aminopropyl)-6-β-methylerythromycin A 9-oxime

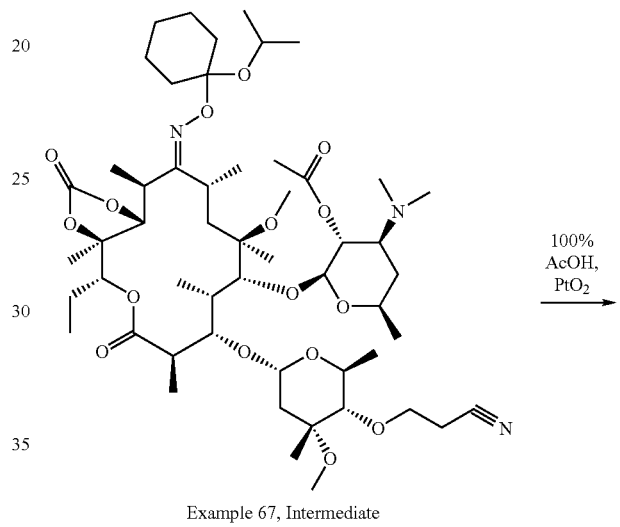

Example 67, Intermediate

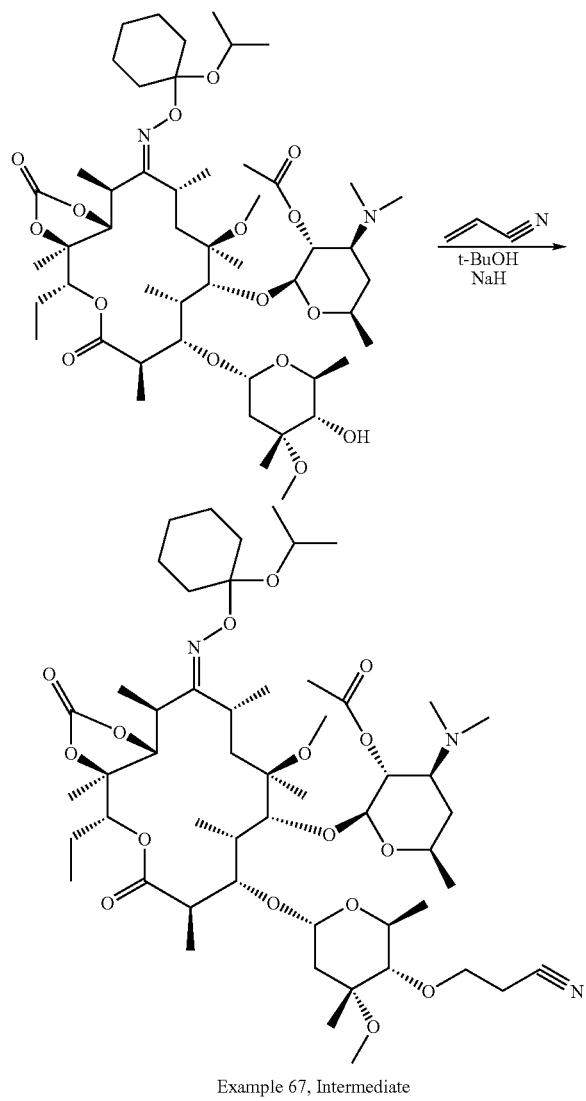

Example 67, Intermediate

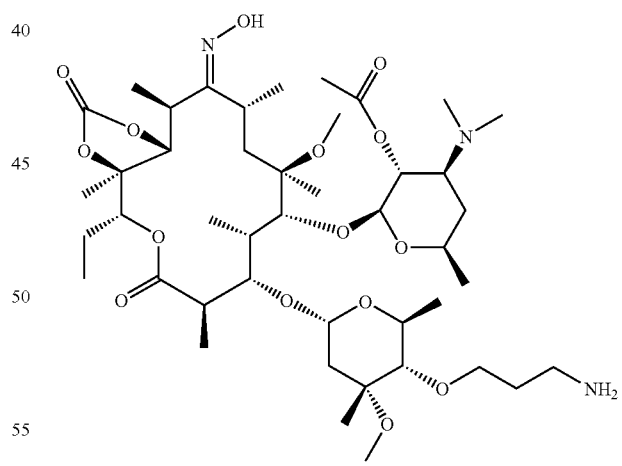

A suspension of the Example 67, Intermediate (2.07 g, 2.02 mmol) and PtO$_2$ (360 mg) in glacial HOAc (65 ml) was hydrogenated at 5 bar overnight. The reaction mixture was filtrated, HOAc evaporated and the residue dissolved in DCM (30 ml) and H$_2$O (30 ml), pH was adjusted to 9.4, layers were separated, and the water layer was extracted with DCM (2×30 ml). Combined organic layers were dried over K$_2$CO$_3$. Evaporation of solvent afforded 1.35 g of the title product.

MS (ES+) m/z: [MH]$^+$=888.9

Example 68

4''-O-(3-aminopropyl)-6-O-methylerythromycin A 9-oxime

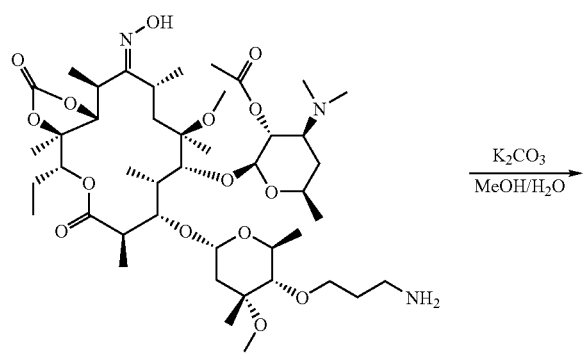

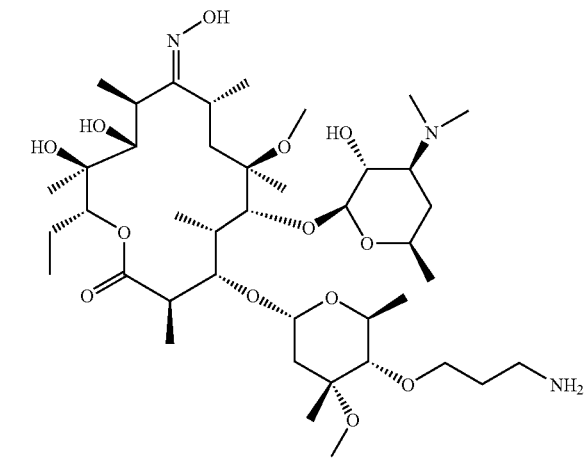

A solution of the compound of Example 67 (1.34 g, 1.51 mmol) and K$_2$CO$_3$ (3.54 g, 25.7 mmol) in MeOH (100 ml) and H$_2$O (30 ml) was stirred at 50° C. for 2 h and then overnight at room temperature. After which MeOH was evaporated, DCM (100 ml) and H$_2$O (30 ml) were added. Layers were separated and organic layer dried over K$_2$CO$_3$. Evaporation of the solvent afforded 0.96 g of the crude title product which was purified using column chromatography on silica gel (DCM/MeOH/NH$_4$OH=90:9:1.5 as eluent) to obtain 0.46 g of the title product.

MS (ES+) m/z: [MH]$^+$=820.8

Example 69

4'-O-(3-aminopropyl)-6-O-methylerythromycin A

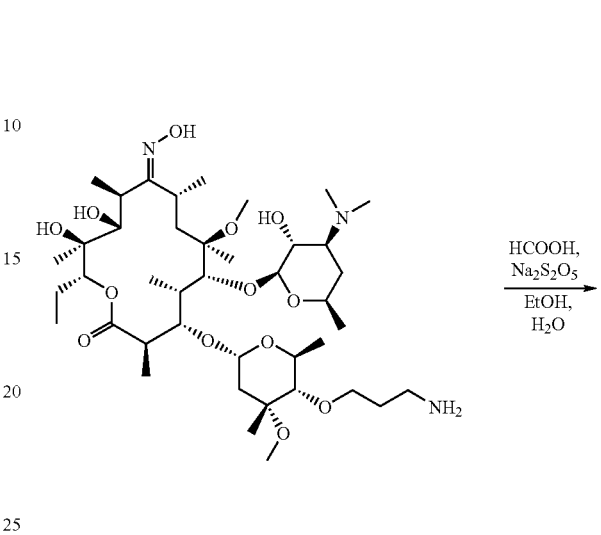

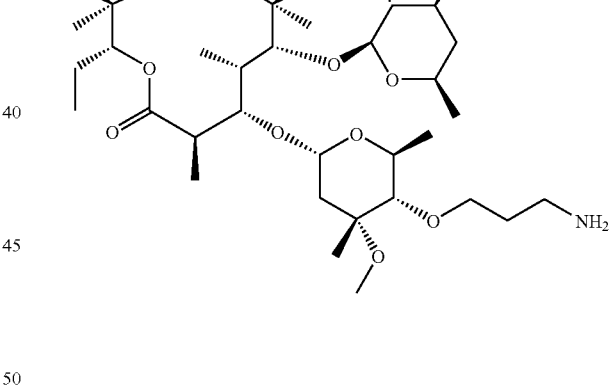

To a solution of the compound of Example 68 (0.39 g, 0.48 mmol) and HCOOH (50.7 µl, 1.34 mmol) in EtOH (5 ml) and H$_2$O (6 ml), Na$_2$S$_2$O$_5$ (0.365 g, 0.96 mmol) was added at room temperature. The reaction mixture was warmed up to 80° C. and than second portion of Na$_2$S$_2$O$_5$ (0.365 g, 0.96 mmol) was added. After stirring at 80° C. for 4 h, ethanol was evaporated, the residue diluted with DCM (50 ml) and water (25 ml), pH adjusted to 9.3, layers separated, and water layer extracted with DCM (2×10 ml). Combined organic layers were dried over K$_2$CO$_3$. Evaporation of the solvent afforded 0.36 g of the crude product which was purified using column chromatography on silica gel (DCM/MeOH/NH$_4$OH=90:9: 1.5 as eluent) to obtain 0.22 g of the title product.

MS (ES+) m/z: [MH]$^+$=805.4

Example 70

11,12-carbonate-2'-O-acetyl-4"-O-(2-cyanoethyl)-6-O-methyl-9a-aza-9a-homoerythromycin A

Example 71

4"-O-(2-cyanoethyl)-6-O-methyl-9a-aza-9a-homoerythromycin A

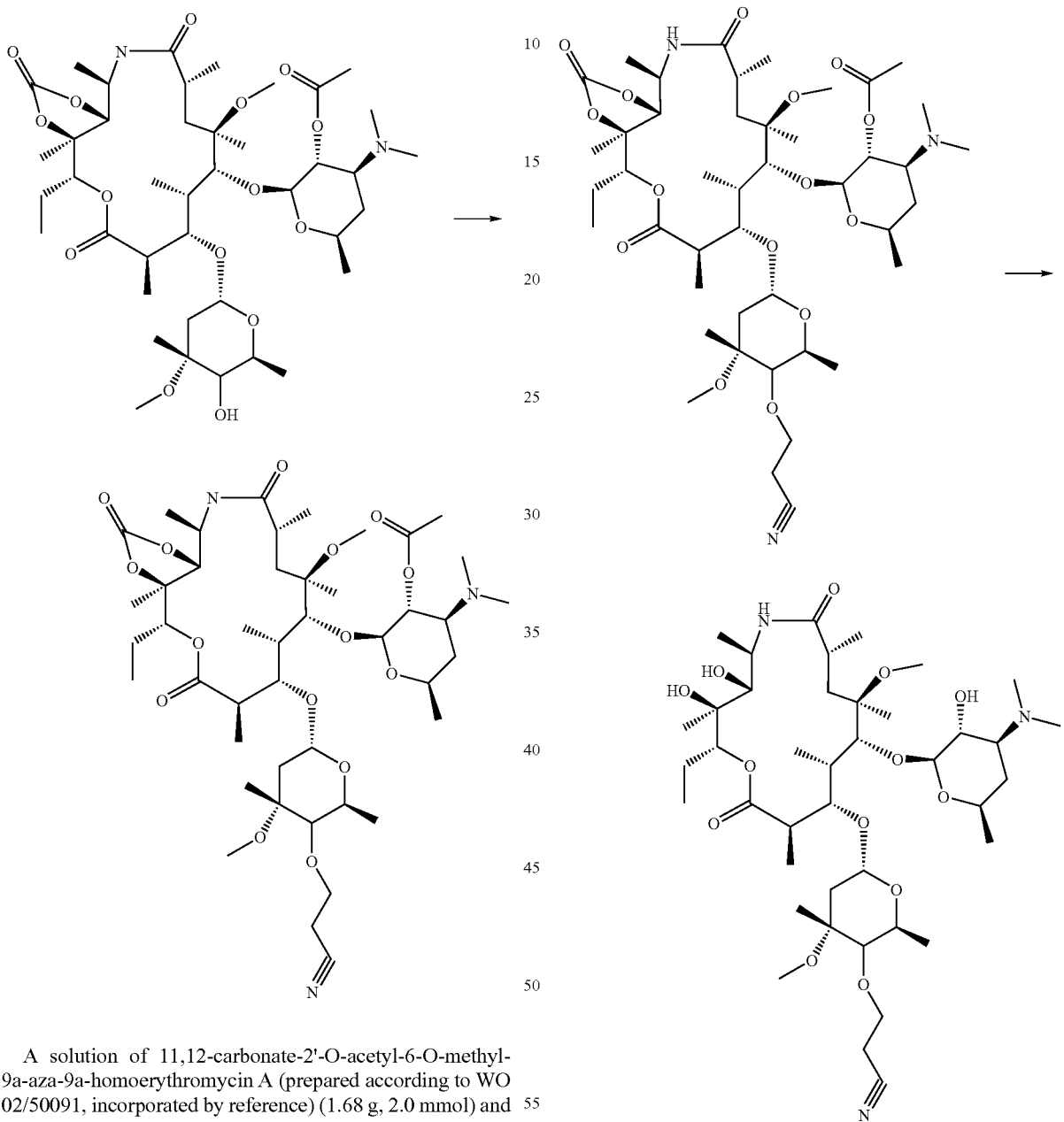

A solution of 11,12-carbonate-2'-O-acetyl-6-O-methyl-9a-aza-9a-homoerythromycin A (prepared according to WO 02/50091, incorporated by reference) (1.68 g, 2.0 mmol) and tert-butanol (1 ml) in acrylonitrile (40 ml) was cooled to 0° C. Sodium hydride (0.15 g, 3.75 mmol, 60% in oil) was then added and the reaction stirred for 7 h. Acrylonitrile was evaporated under reduced pressure, ethyl acetate (200 ml) was added and filtrated. Filtrate was washed with saturated aqueous solution of NaHCO$_3$ (100 ml) and brine (100 ml), and dried over anhydrous Na$_2$SO$_4$. Evaporation of the solvent afforded crude product which was purified using column chromatography on silica gel (DCM/MeOH/NH$_4$OH=90:5:0.5 as eluent) to obtain 1.33 g of the title product.

MS m/z: (ES): MH$^+$=884.9

A solution of the compound of Example 70 (1.33 g, 1.5 mmol) and K$_2$CO$_3$ (0.45 g, 3.2 mmol) in MeOH (65 ml) and of H$_2$O (22 ml) was stirred for 7 h at 50° C. Methanol was then evaporated, EtOAc (200 ml) was added and layers separated. Organic layer was washed with saturated aqueous solution of NaHCO$_3$ (100 ml) and brine (100 ml), and dried over anhydrous Na$_2$SO$_4$. Evaporation of the solvent afforded 1.11 g of the title product.

MS m/z: (ES): MH$^+$=816.9

Example 72

4''-O-(3-aminopropyl)-6-O-methyl-9a-aza-9a-homo-erythromycin A

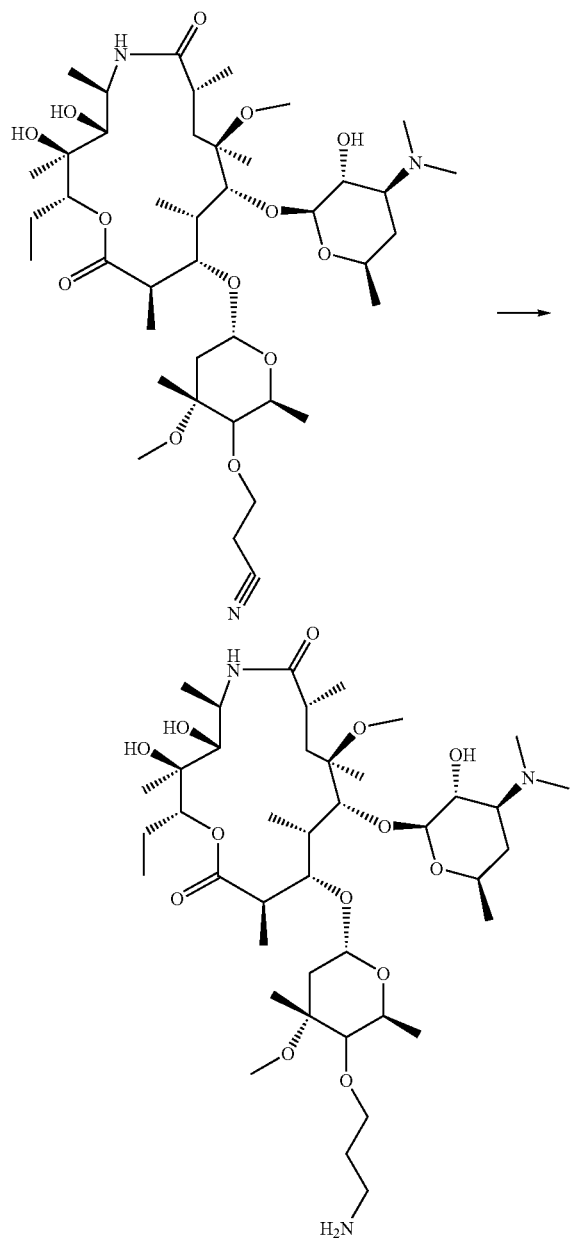

A solution of the compound of Example 71 (1.11 g, 1.32 mmol) and PtO$_2$ (0.25 g, 0.11 mmol) in glacial HOAc (60 ml) was hydrogenated at 4.5 bar overnight. Catalyst was removed by filtration and filtrate was washed with DCM (2×20 ml). Filtrate was concentrated in vacuo affording the crude product which was dissolved in DCM (100 ml), to which water was added (50 ml), pH was adjusted to 9.5, and layers separated. Organic layer was dried over anhydrous Na$_2$SO$_4$. Evaporation of the solvent afforded crude product which was purified using column chromatography on silica gel (EtOAc/hexane/diethylamine 5:5:1 as eluent) to obtain 0.6 g of the title product.

MS m/z: (ES): MH$^+$=820.8

Example 73

4''-O-(3-Diethylaminopropyl)-6-O-methyl-9a-aza-9a-homoerythromycin A

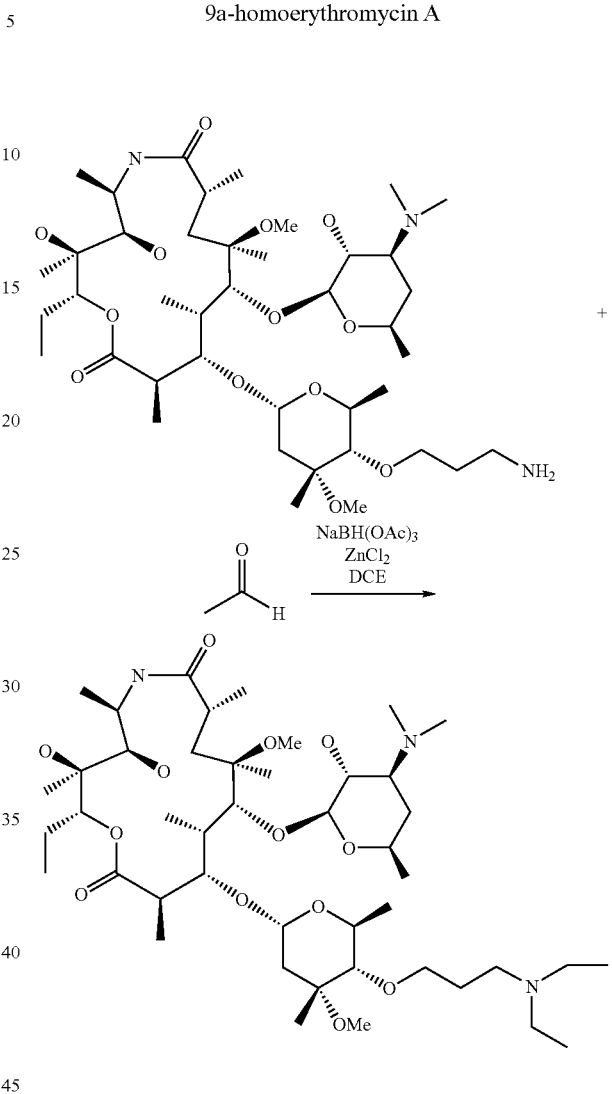

A solution of the compound of Example 72 (100.0 mg, 0.12 mmol) in DCE (5 ml) was stirred for 5 min. at the room temperature. Molecular sieves (4A), acetaldehyde (20.5 µl, 0.36 mmol), NaBH(OAc)$_3$, (77.3 mg, 0.36 mmol) and ZnCl$_2$ (16.6 mg, 0.12 mmol) were then added. The reaction mixture was stirred for 1 hour at room temperature. After evaporation of the solvent, the residue was taken up into DCM (10 ml) and extracted with saturated aqueous solution of NaHCO$_3$ (3×5 ml), brine (3×5 ml) and water (3×5 ml). Combined aqueous layers were extracted with DCM (2×20 ml). Combined DCM layers were dried over MgSO$_4$. After evaporation of the solvent, crude product was purified using preparative HPLC (XTerra Prep RP18 kolona 5 µm 19×100 mm) to afford 26 mg of the title product.

MS m/z: (ES): MH$^+$=876.6

$^{13}$C NMR (125 MHz. CDCl$_3$) [δ/ppm]

179.9, 177.4, 102.3, 95.5, 87.8, 79.6, 78.5, 78.3, 76.2, 74.2, 73.6, 73.0, 72.9, 71.2, 67.7, 64.9, 64.9, 51.4, 49.7, 49.5, 46.8, 45.4, 44.7, 41.3, 40.1, 40.3, 35.6, 35.5, 29.2, 27.7, 21.8, 21.6, 20.7, 20.5, 19.4, 18.8, 16.2, 15.2, 14.0, 11.2, 9.2, 11.4.

Example 74

2'-O-Acetyl-4"-O-(2-cyanoethyl)-11-O-methyl-azithromycin

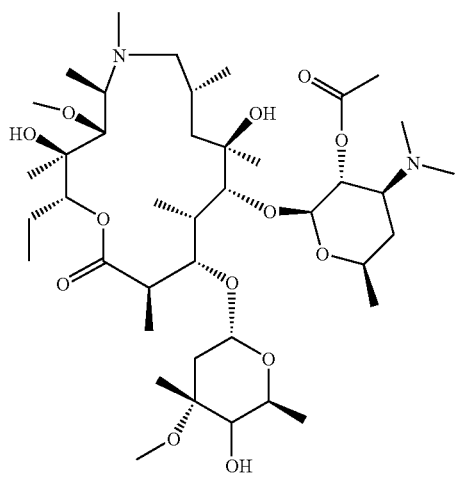

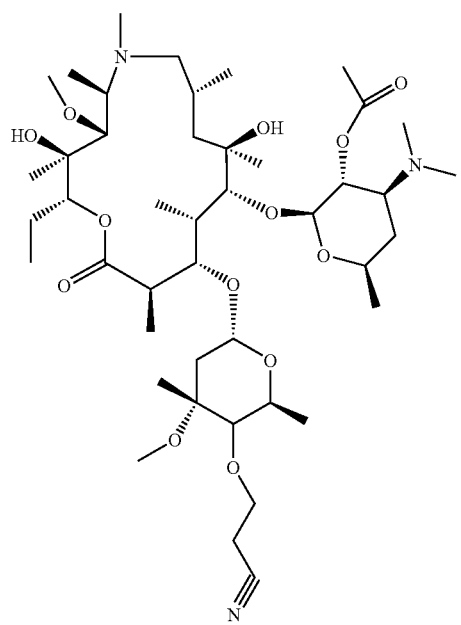

To a solution of the compound of 2'-O-Acetyl-11-O-methyl-azithromycin (1.0 g, 1.2 mmol) in acrylonitrile (25 ml), t-BuOH (0.3 ml, 3.6 mmol) and NaH (52.8 mg, 1.3 mmol) were added in portions under nitrogen at 0° C. and then stirred at 0° C. for 1 hour. Acrylonitrile was evaporated, the residue dissolved in DCM (25 ml) and extracted with water (3×20 ml). Polymer precipitated between layers was filtered off, the organic layer dried over $K_2CO_3$ and evaporated in vacuum yielding 1.1 g of the title product.

MS (ES) m/z: $[MH]^+$ 858.5

Example 75

2'-O-Acetyl-4"-O-(3-aminopropyl)-11-O-methyl-azithromycin

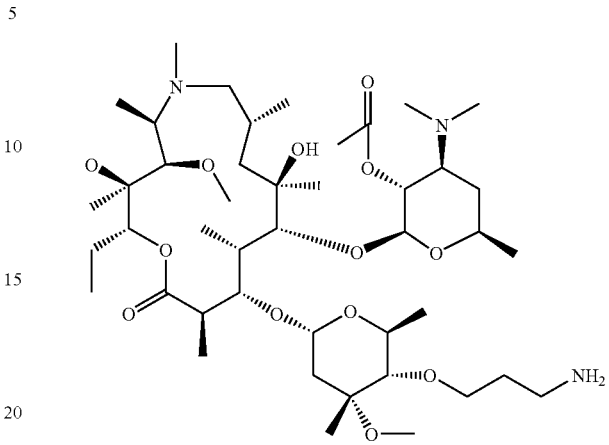

To a solution of Example 74 (1.0 g, mmol) in glacial HOAc (30 ml), $PtO_2$ (0.2 g) was added and the reaction mixture was hydrogenated in Parr apparatus at 5 bar for 18 hours. The catalyst was filtered through cellite and the solvent was evaporated in vacuum, water (50 ml) was added, pH adjusted to 8.5 and extracted with DCM (50 ml). The organic layer was evaporated in vacuum yielding 0.9 g of the title product.

MS (ES) m/z: $[MH]^+$ 862.4

$^{13}$C-NMR (125 MHz, $CDCl_3$) δ: 177.1, 169.0, 99.3, 94.3, 86.5, 85.0, 82.8, 77.2, 76.7, 74.0, 73.5, 72.5, 72.1, 71.4, 69.5, 66.6, 63.9, 62.6, 61.6, 60.8, 48.6, 44.5, 41.6, 41.5, 40.3, 39.2, 34.6, 34.0, 30.2, 27.2, 26.2, 22.0, 21.3, 21.1, 21.0, 18.1, 17.5, 14.4, 10.9, 8.6, 7.7.

Example 76

4"-O-(3-Aminopropyl)-11-O-methyl-azithromycin

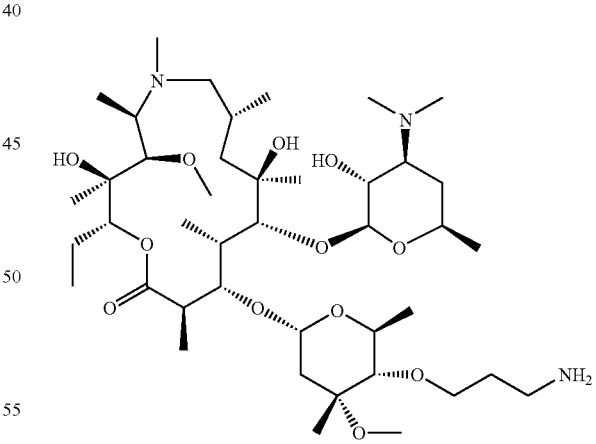

The compound of Example 75 (0.100 g, 0.11 mmol) was dissolved in MeOH (40 ml) and the mixture was stirred at 50° C. for 18 hours. Methanol was evaporated under reduced pressure to yield 95 mg of the title product.

MS (ES) m/z: $[MH]^+$ 820.3

$^{13}$C-NMR (125 MHz, $CDCl_3$) δ: 177.3, 101.8, 94.2, 86.7, 84.9, 82.5, 77.1, 76.6, 74.1, 73.4, 72.6, 71.9, 70.6, 69.7, 66.7, 64.6, 63.9, 61.7, 60.8, 48.7, 44.7, 42.1, 42.0, 40.3, 39.1, 34.7, 34.8, 30.1, 27.3, 26.2, 22.1, 21.6, 21.1, 21.0, 18.2, 17.6, 14.4, 10.9, 9.0, 7.7.

Examples 77 to 83

Intermediate: 2'-O-acetyl-4''-O-(imidazole-1-carbonyl)-6-O-methyl-9a-aza-9a-homoerythromycin A

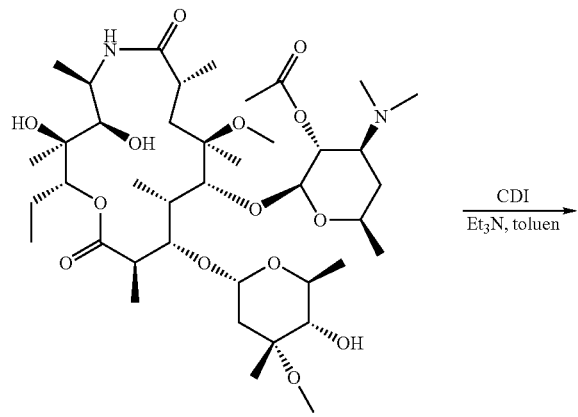

Intermediate of Examples of 77 to 83

→ CDI, Et₃N, toluen

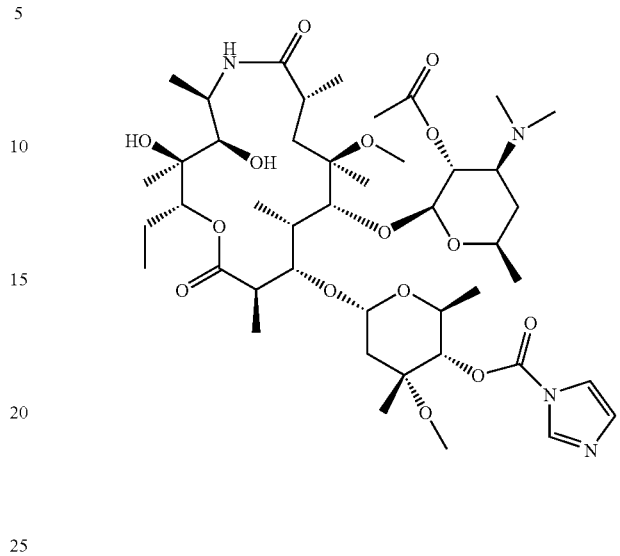

A solution of 2'-O-acetyl-6-O-methyl-9a-aza-9a-homoerythromycin (4.00 g, 6.18 mmol) in dry toluene (50 ml) was stirred for 5 min. Triethylamine (5.15 ml, 37.20 mmol) and CDI (2.43 ml, 13.67 mmol) were added and the mixture stirred for 24 hours at room temperature. Second portion of CDI (2.43 ml, 13.67 mmol) was added and stirring was continued for further 48 hours. The reaction mixture was extracted with saturated aqueous solution of NaHCO₃ (1×50 ml, 2×30 ml). Combined aqueous layers were extracted with toluene (2×20 ml). Combined toluene layers were dried over MgSO₄ and evaporation under reduced pressure to gave 9.21 g of the title product.

MS m/z: (ES): MH⁺=899.0

General Procedure for 4''-O-Carbamoyl-6-O-Methyl-9a-aza-9a-homoerythromycin A Preparation 1. R—H, DBU, DMF
2. MeOH →

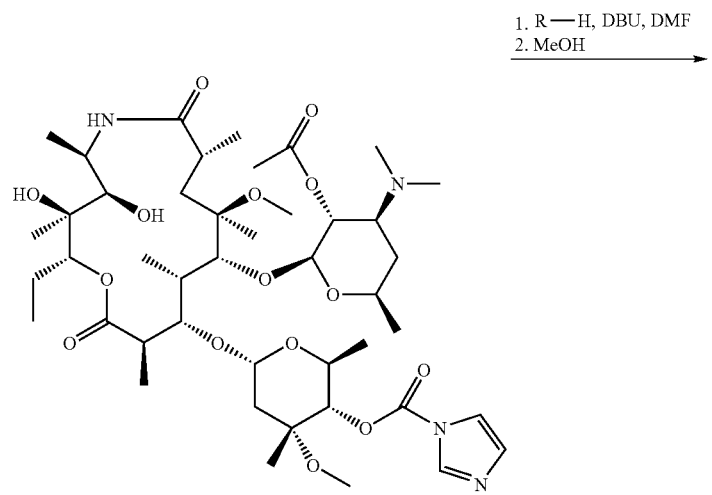

-continued
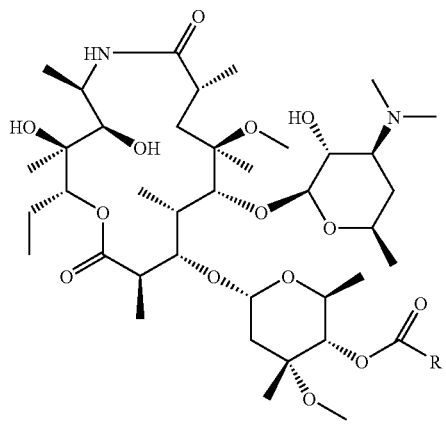
| Product | R | MS (ES. m/z) | mass/mg | purity % | yield % |
|---|---|---|---|---|---|
| Example 77 | ![structure] | 906.2 [M + H]⁺. calc. 905.2 | 22.2 | 99.5 | 43.8 |
| Example 78 | ![structure] | 989.6 [M + H]⁺. calc. 988.3 | 18.4 | 98.5 | 33.3 |
| Example 79 | ![structure] | 975.2 [M + H]⁺. calc. 974.3 | 21.8 | 99.0 | 40.0 |
| Example 80 | ![structure] | 947.2 [M + H]⁺. calc. 946.2 | 18.4 | 96.5 | 34.7 |
| Example 81 | ![structure] | 920.4 [M + H]⁺. calc. 919.2 | 17.1 | 98.7 | 33.2 |
| Example 82 | ![structure] | 892.2 [M + H]⁺. calc. 891.1 | 13.2 | 89.6 | 26.4 |

| | | | | | |
|---|---|---|---|---|---|
| -continued | | | | | |
| Example 83 | 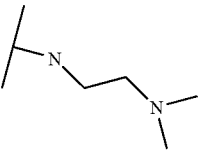 | 878.2 [M + H]+. calc. 877.1 | 23.9 | 100 | 50.7 |

Reaction mixture was stirred at 40° C. for 48 hours and then cooled to room temperature. Solvent was removed under reduced pressure, oily product was dissolved in MeOH (3.0 ml) and mixture was stirred at 40° C. for 48 hours. After evaporation of the solvent crude product was purified using preparative HPLC (XTerra Prep RP18 column 5 μm 19×100 mm).

Example 84

Diacetate Salt of Example 81

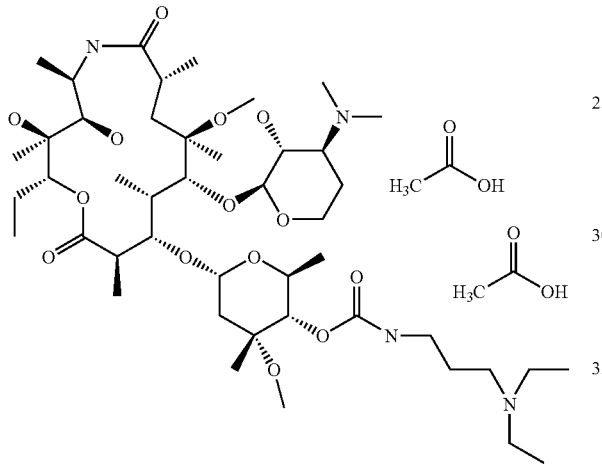

To a solution of Example 81 (0.1 g, 0.11 mmol) in i-PrOH (0.600 ml) acetic acid (0.0132 ml, 0.231 mmol) was added under stirring in an ice bath. After addition of diisopropylether (3 ml) and n-hexane (10 ml), solvent was evaporated under reduced pressure to yield 0.100 g of the diacetate salt.

Example 85

Dihydrochloride Salt of Example 77

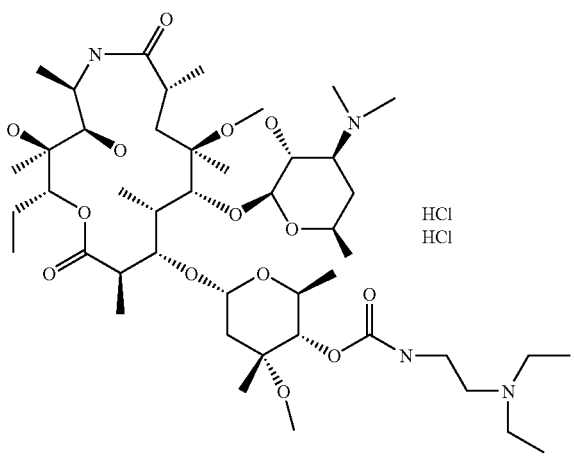

Compound of Example 77 (0.100 g, 0.11 mmol) was dissolved in i-PrOH (0.60 ml) and then HCl/1-PrOH (5 M, 0.0462 ml, 0.231 mmol) was added. The hydrochloric salt was isolated by precipitation with n-hexane (10 ml). After filtration 0.126 g of dihydrochloric salt was obtained.

Example 86

4″-O-[3-(2-Dimethylamino-ethylamino)-propionyl]-6-O-methyl-9a-aza-9a-hooerythromycin A

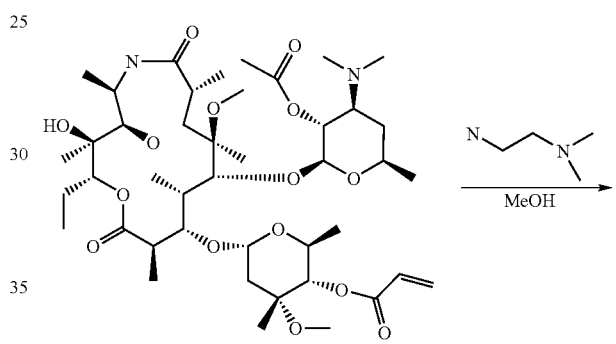

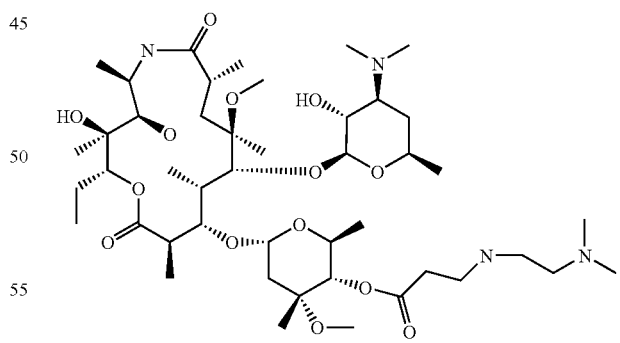

A solution of 2'-O-acetyl-4-O-propenoyl-6-O-methyl-9a-aza-9a-homoerythromycin A (prepared according to WO 03/042228) (0.859 g, 1 mmol) and N,N-dimethylethylamine (1.1 ml, 10 mmol) in MeOH (20 ml) was stirred at 55° C. for 18 hours. Methanol was evaporated and residue purified by flash chromatography using DCM/MeOH/NH$_4$OH=90:9:1.5 as eluent to give 470 mg of the title product.

MS (ES+) m/z: [MH]+=905.5

Example 87

4''-O-(3-Diethylamino-propionyl)-11-O-(2-cyano-ethyl)-6-O-methyl-9a-aza-9a-homoerythromycin A

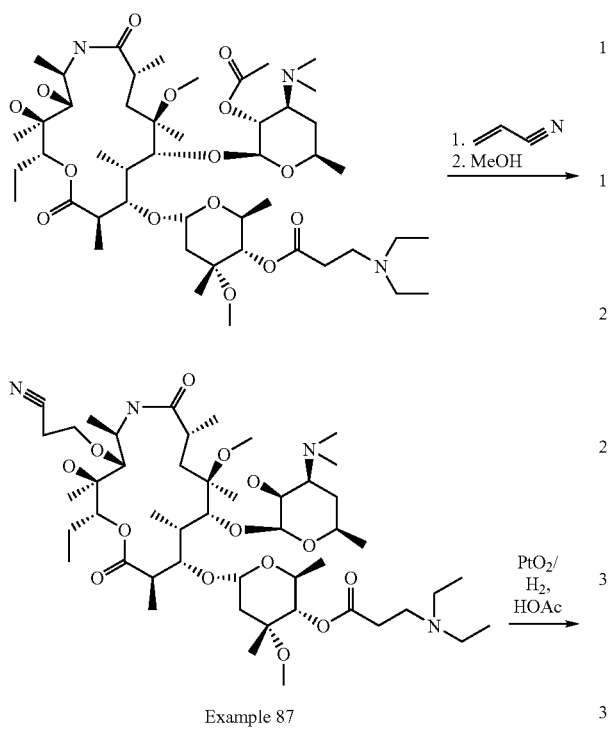

Starting from 2'-O-acethyl protected compound of Example 8 and acrylonitrile, according to the procedure described for Intermediate 2, Example 4, following deprotection of 2'-O-acetyl group in methanol provides the title compound.

All compounds in this Example each have the substituent bonded at the C-2 of the desosaminyl sugar in the S absolute stereochemical configuration, and therefore, is in an anti stereochemical configuration compared to the stereochemical configurations of the substituents bonded at the C-1 and C-3 of the desosaminyl sugar.

Example 88

4''-O-(3-Diethylamino-propionyl)-11-O-(3-amino-propyl)-6-O-methyl-9a-aza-9a-homoerythromycin A Starting from the compound of Example 87 using the procedure of Example 6 the title compound is obtained.

Example 89

3'-N-Demethyl-4''-O-propenoyl-azithromycin

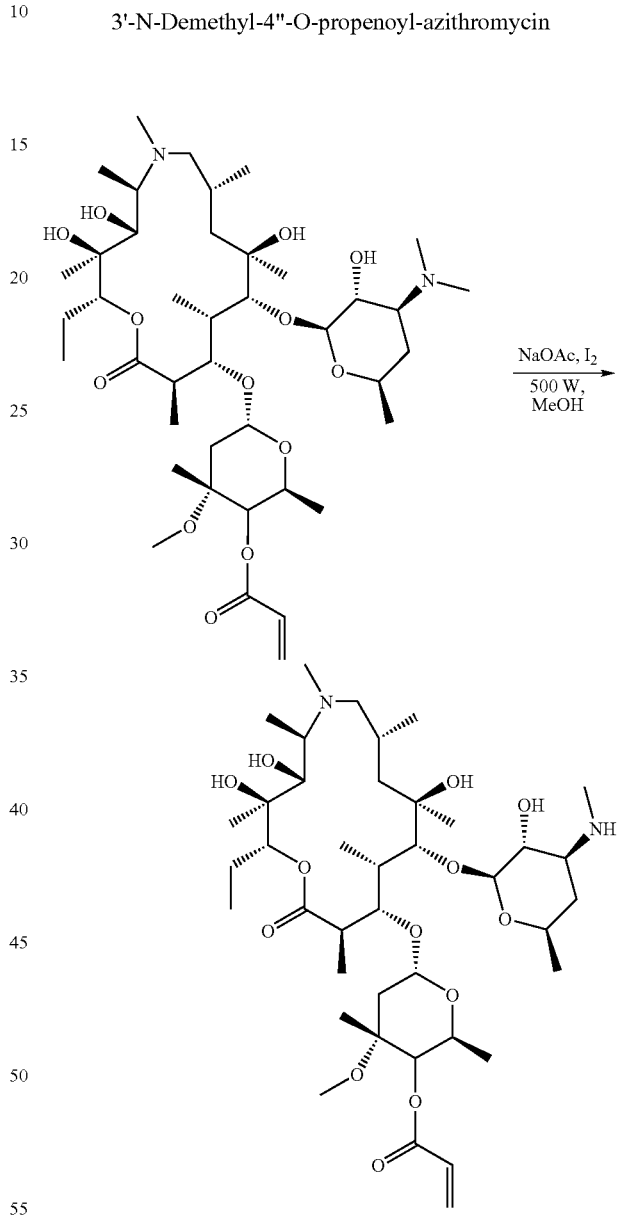

To a stirred solution of 4''-O-propenoyl-azithromycin (0.5 g, 0.62 mmol), obtained as described in international patent application WO 03/042228 and NaOAc (0.23 g, 2.8 mmol) in MeOH (12.5 ml) solid iodine (0.16 g, 0.62 mmol) was added. The reaction mixture was irradiated using 500 W halogen lamp for 2 hours, cooled to room temperature, and the solvent evaporated. Solid residue was dissolved in EtOAc (100 ml), filtrated, and the filtrate washed with saturated $NaHCO_3$ (25 ml) and saturated NaCl (25 ml). Organic layer was dried over $Na_2SO_4$ and evaporated to give the title product (0.4 g).

MS m/z: (ES): $MH^+$=789.5.

Example 90

3'-N-Demethyl-4"-O-(3-diethylaminopropionyl)-azithromycin

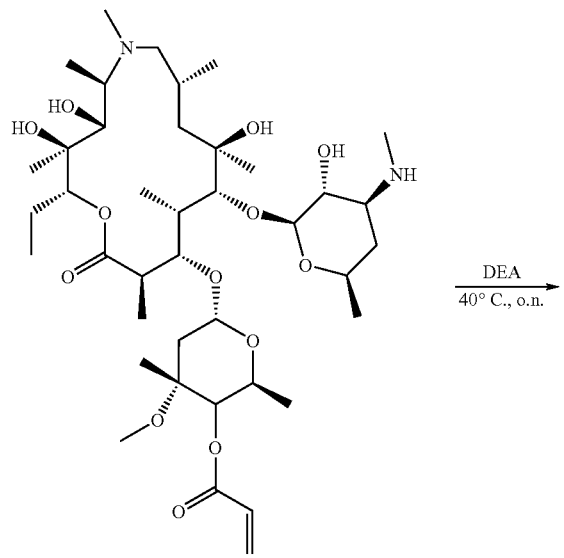

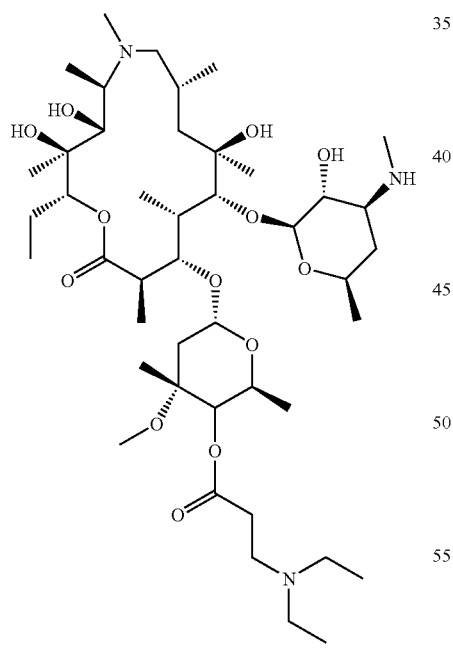

A solution of the compound of Example 89 (0.4 g, 0.51 mmol) in diethyl amine (10 ml) was heated overnight at 40° C., cooled to room temperature, and evaporated to dryness. Flash chromatography of crude product on silica gel using hexane/EtAc/diethyl amine=10:1:1 as eluent afforded the title product (0.19 g).

MS m/z: (ES): MH$^+$=862.8.

Example 91

3'-N-Demethyl-4"-O-propenoyl-6-O-methyl-erythromycin A 11,12-cyclic carbamate

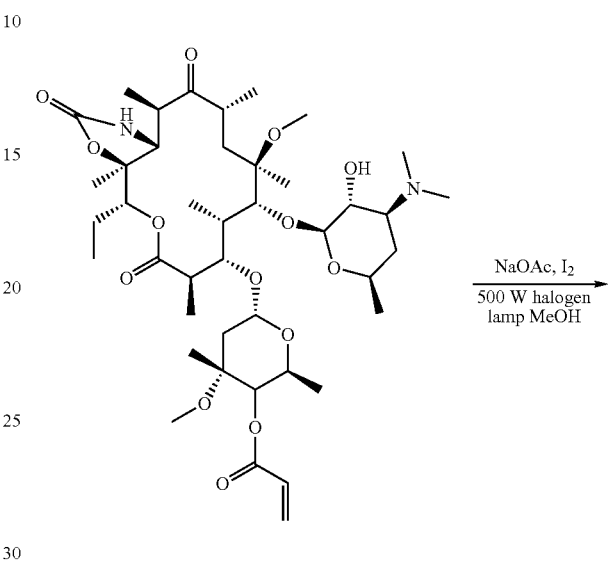

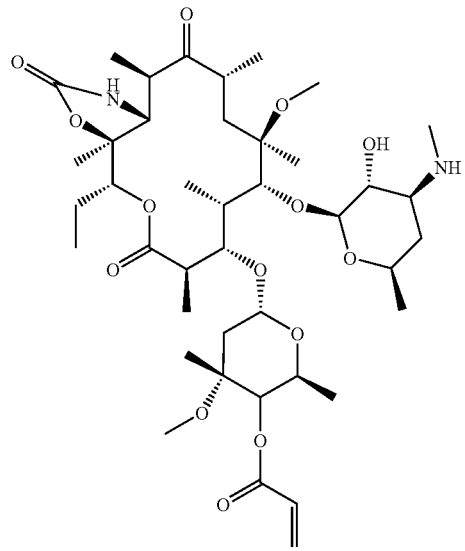

Starting from 4"-O-propenoyl-6-O-methyl-erythromycin A 11,12-cyclic carbamate (0.25 g, 0.30 mmol), obtained as described in international patent application WO 03/042228 and solid iodine (0.08 g, 0.31 mmol) according to the procedure described for Example 89 the title compound (0.21 g) was obtained.

MS m/z: (ES): MH$^+$=813.6.

125

Example 92

3'-N-Demethyl-4"-O-(3-diethylaminopropionyl)-6-O-methyl-erythromycin A 11,12-cyclic carbamate

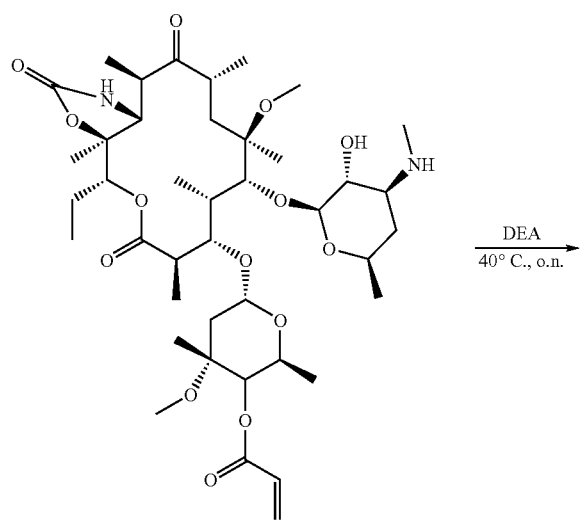

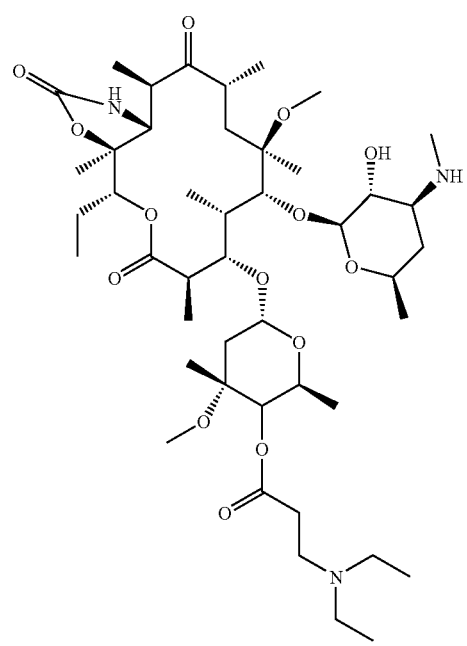

Starting from Example 91 (0.21 g, 0.26 mmol) and diethyl amine (5 ml) according to the procedure described for the Example 90 the title compound (0.095 g) was obtained.

MS m/z: (ES): MH$^+$=886.8.

126

Example 93

3'-N-Demethyl-4"-O-propenoyl-6-O-methyl-erythromycin A

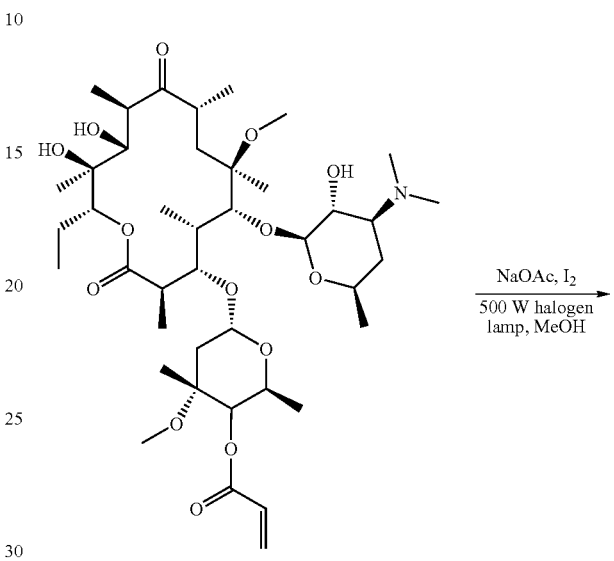

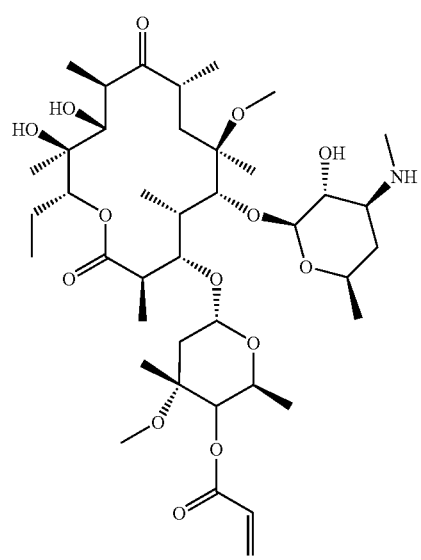

Starting from 4"-O-propenoyl-6-O-methyl-erythromycin A (0.24 g, 0.30 mmol), obtained as described in international patent application WO 03/042228 and solid iodine (0.08 g, 0.31 mmol) according to the procedure described for Example 89 the title compound (0.21 g) was obtained.

MS m/z: (ES): MH$^+$=788.6.

Example 94
3'-N-Demethyl-4"-O-(3-diethylaminopropionyl)-6-O-methyl-erythromycin A
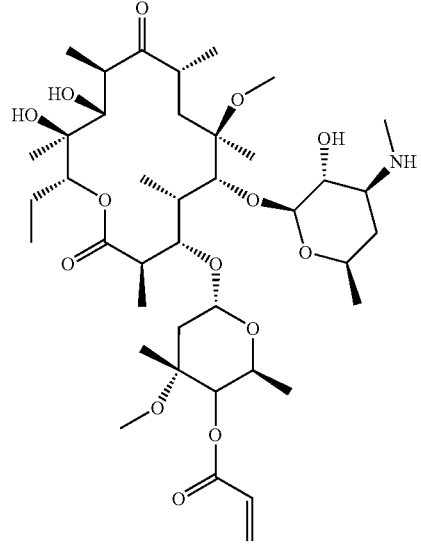
Starting from Example 93 (0.21 g, 0.27 mmol) and diethyl amine (5 ml) according to the procedure described for the Example 90 the title compound (0.15 g) was obtained.
MS m/z: (ES): MH$^+$=861.7.
Example 95
4"-O-(3-diethylamino-propyl)-azithromycin 11,12-cyclic carbonate
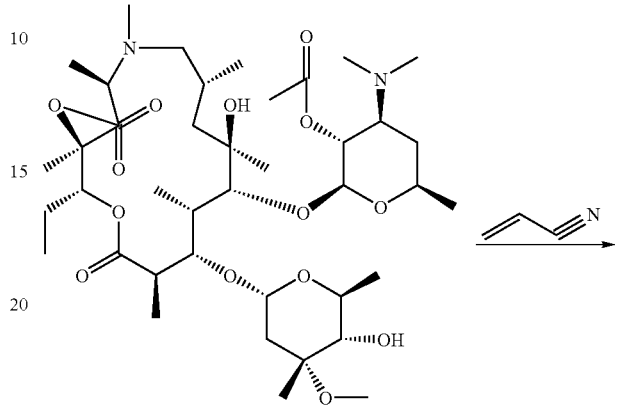
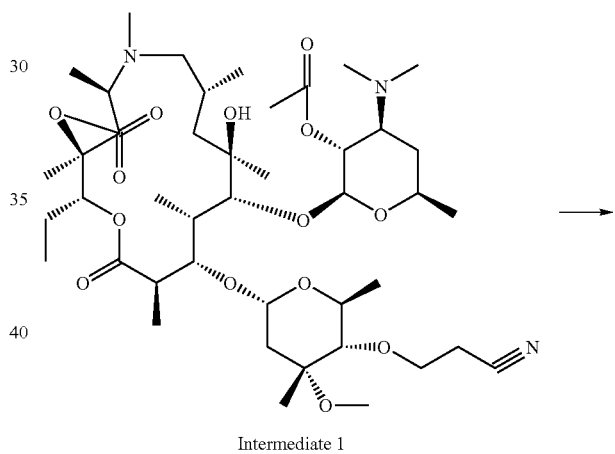
Intermediate 1
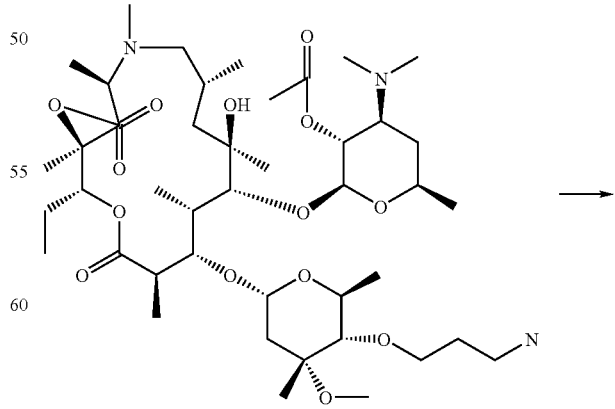
Intermediate 2

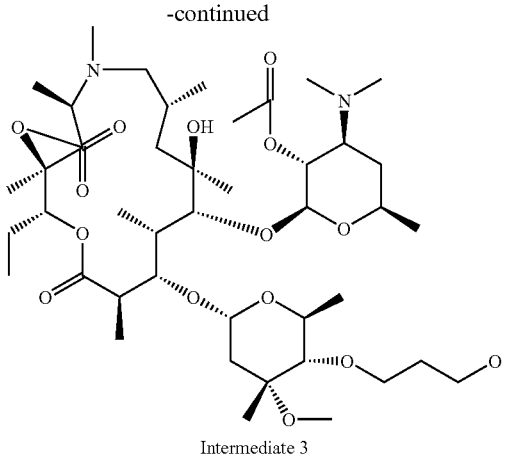

Intermediate 3

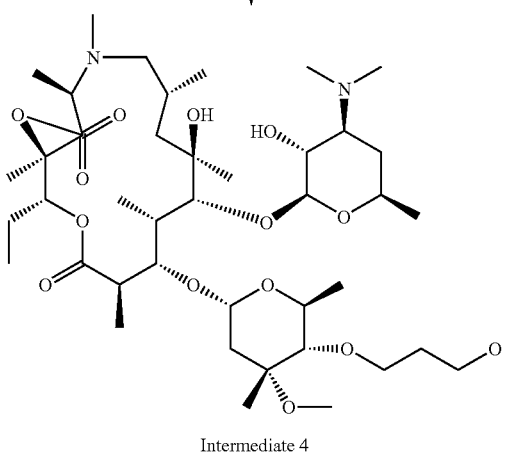

Intermediate 4

Intermediate 1

2'O-Acetyl-4"-O-(2-cyanoethyl)-azithromycin 11,12-cyclic carbonate

To the degassed solution of 2'O-acetyl-azithromycin 11,12-cyclic carbonate (10 g, 12.2 mmol) in acrylonitrile (250 ml) were added t-BuOH (3.465 ml, 36 mmol) and NaH (528 mg, 13.2 mmol) in portions at 0° C. The reaction mixture was stirred for 12 hours allowing to reach room temperature. Acrylonitrile was evaporated and the residue dissolved in DCM (50 ml), extracted with water (3×50 ml). The organic layer was dried over $K_2CO_3$ and evaporated in vacuum yielding the title product (9.33 g).

MS m/z: (ES): $MH^+$=870.6.

Intermediate 2 2'O-Acetyl-4"-O-(3-aminopropyl)-azithromycin 11,12-cyclic carbonate Reduction of Intermediate 1 (3 g, 3.45 mmol) with $PtO_2$ (1.0 g) in glacial HOAc (120 ml) at 5 bar for 18 hours gave the title product (1.46 g).

MS m/z: (ES): $MH^+$=875.0.

Intermediate 3 2'O-Acetyl-4"-O-(3-hydroxypropyl)-azithromycin 11,12-cyclic carbonate To the solution of Intermediate 2 (5.0 g, 5.72 mmol) in 10% water solution of HOAc (100 ml) was added $NaNO_2$ (2.605 g, 37.75 mmol) in portions at 0° C. After 3 hours, an additional amount of $NaNO_2$ (1.3 g, 18.84 mmol) was added. The reaction mixture was left overnight at 4° C. DCM was added to the reaction mixture and the pH was adjusted to 10.7 by addition of 20% NaOH. The layers were separated, organic layer dried over $K_2CO_3$ and evaporated in vacuum yielding the title product (4.70 g).

MS m/z: (ES): $MH^+$=875.9

$^{13}$C-NMR (75 MHz, $CDCl_3$) δ, ppm: 177.16, 170.36, 153.39, 100.11, 94.87, 87.24, 86.51, 84.83, 84.17, 77.54, 76.54, 74.69, 73.78, 73.44, 68.02, 67.41, 64.46, 63.42, 63.02, 61.62, 49.42, 45.07, 42.91, 42.45, 41.91, 34.99, 34.65, 32.44, 30.61, 27.06, 26.28, 22.26, 22.19, 22.09, 21.38, 18.38, 14.97, 13.86, 10.54, 10.01, 5.30.

Intermediate 4
4"-O-(3-hydroxypropyl)-azithromycin 11,12-cyclic carbonate Intermediate 3 (4.0 g, 4.6 mmol) was dissolved in MeOH (250 ml) and stirred overnight at 40° C. Methanol was evaporated under reduced pressure to give the title compound (2.3 g).

MS m/z: (ES): $MH^+$=833.8.

4"-O-(3-diethylamino-propyl)-azithromycin 11,12-cyclic carbonate

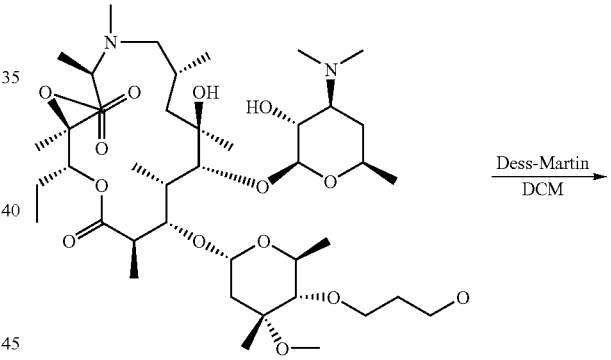

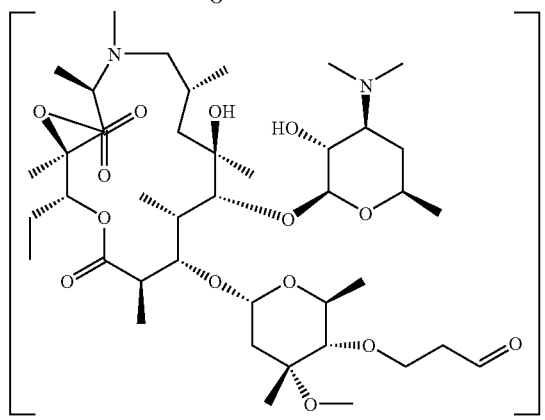

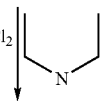

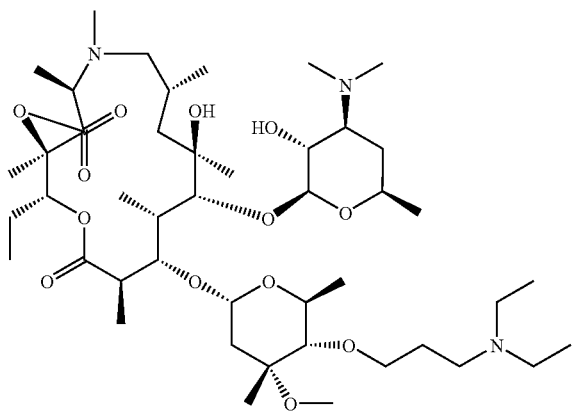

To the solution of Intermediate 4, Example 95 (0.2 g, 0.24 mmol) in DCM (2 ml), Dess-Martin reagens (0.112 g, 0.264 mmol) was added. The reaction mixture was stirred at room temperature overnight; the aldehyde as white precipitate filtered off and dissolved in DCM (15 ml). To the reaction mixture Et$_2$NH (75 μl, 0.72 mmol), NaBH(AOc)$_3$ (0.153 g, 0.72 mmol), ZnCl$_2$ (0.033 g, 0.24 mmol) and sieves (4 Å) were added, stirred at room temperature for 2 hours and then filtered. The filtrate was evaporated to afford yellow oily product (0.374 g), which was purified by column chromatography (DCM:MeOH:NH$_4$OH=90:9:0.5) to afford the title product (0.117 g).

MS m/z: (ES): MH$^+$=888.3

Example 96

4"-O-(3-diethylamino-propyl)-azithromycin

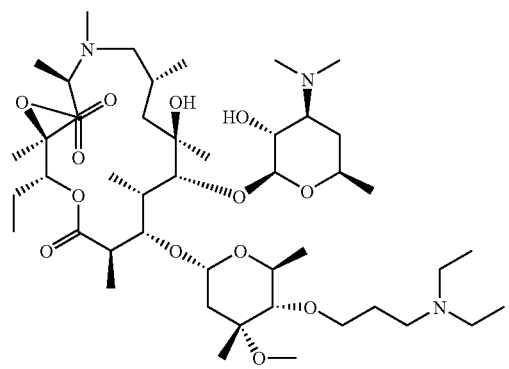

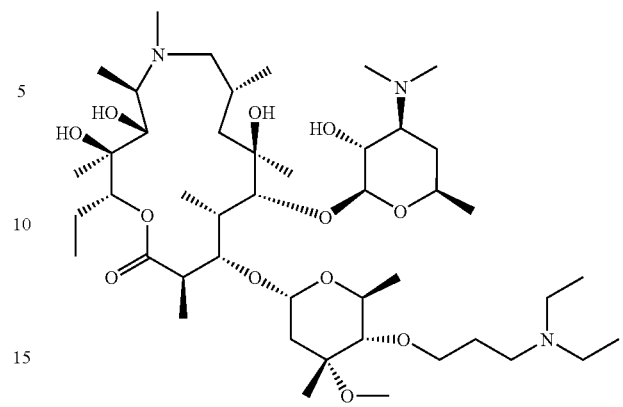

To the solution of Example 95 (80 mg, 0.09 mmol) in MeOH (10 ml), K$_2$CO$_3$ (211 mg, 1.53 mmol) was added in water (3 ml). The reaction mixture was stirred at room temperature overnight, the MeOH was evaporated and the residue was extracted with DCM (3×10 ml). Combined organic layers were dried over 1K$_2$CO$_3$ and the solvent was evaporated. The product was purified by column chromatography (DCM:MeOH:NH$_4$OH=90:9:0.5) to afford the title product (40 mg).

MS m/z: (ES): MH$^+$=862.4

$^{13}$C-NMR (75 MHz, CDCl$_3$) δ: 178.94, 102.34, 94.85, 88.05, 83.23, 77.88, 77.46, 74.27, 73.81, 73.74, 73.68, 72.41, 71.02, 70.10, 67.88, 65.44, 64.70, 62.45, 49.56, 49.49, 46.70, 45.23, 42.32, 42.08, 40.37, 36.29, 35.44, 29.70, 29.09, 27.50, 26.80, 21.97, 21.79, 21.75, 21.30, 18.54, 16.22, 14.72, 11.27, 10.57, 9.16, 7.38.

Example 97

4"-O-{3-[4-(2-Diethylamino-ethyl)-piperazin-1-yl]-propyl}azithromycin 11,12-cyclic carbonate

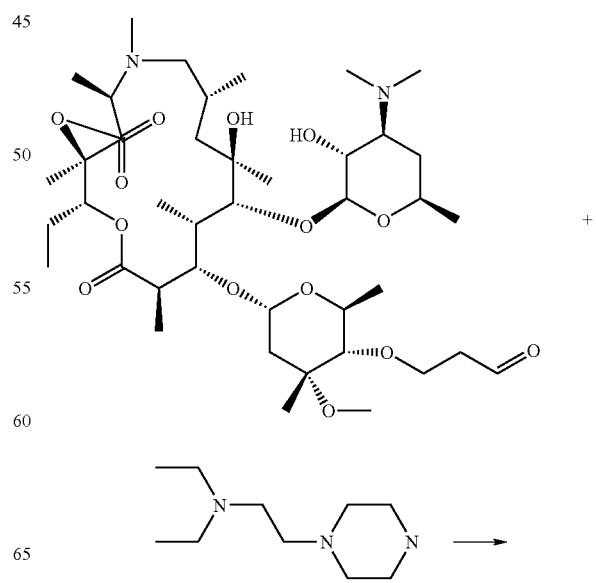

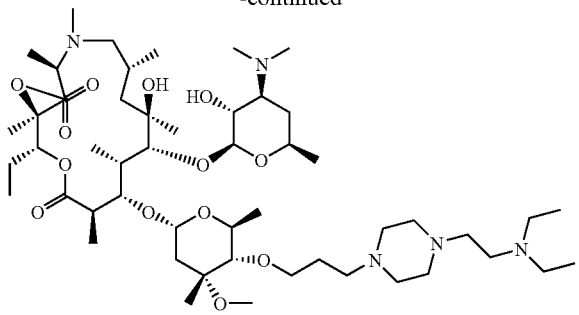

Starting from Intermediate 4 of Example 95 (0.2 g, 0.24 mmol), Dess-Martin reagent (0.112 g, 0.264 mmol) and 1-(2-diethylaminoethyl)piperazine (133 μl, 0.72 mmol) were combined and the title crude product (0.374 g) was obtained according to the procedure for Example 95. The product was purified by column chromatography (DCM:MeOH:NH4OH=90:9:1.5) to afford the title product (37 mg).

MS m/z: (ES): MH+=1000.5

$^{13}$C-NMR (75 MHz, CDCl$_3$) δ: 176.96, 153.41, 103.39, 95.86, 87.75, 85.50, 85.44, 78.37, 76.09, 73.87, 73.48, 72.77, 70.77, 68.48, 67.39, 64.96, 64.73, 60.93, 55.82, 55.14, 54.99, 53.61, 53.53, 53.04, 49.76, 49.69, 47.35, 45.74, 43.00, 41.83, 40.33, 35.82, 34.27, 28.89, 27.65, 26.78, 26.18, 22.06, 21.93, 21.59, 18.35, 15.15, 14.53, 14.11, 11.10, 10.80, 10.37, 5.90.

Example 98

4''-O-(3-diisopropylamino-propyl)-azithromycin 11,12-cyclic carbonate

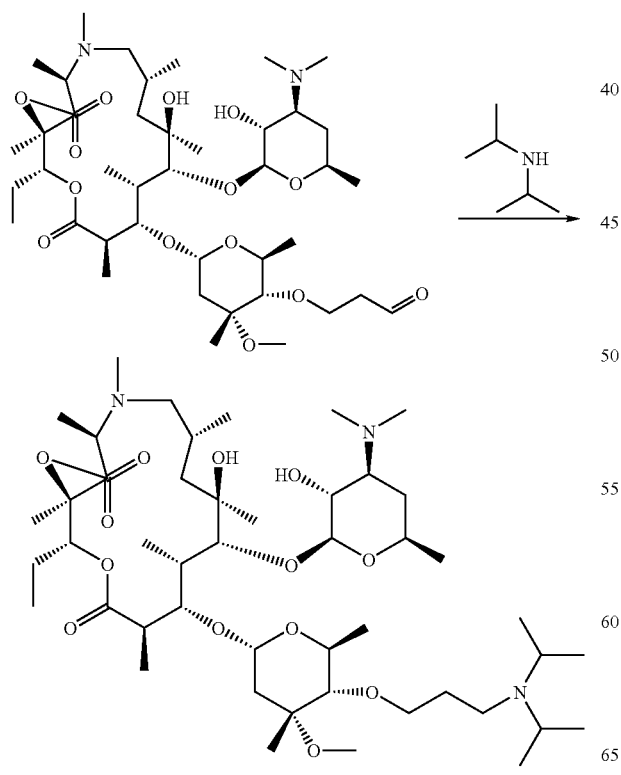

Starting from Intermediate 4 of Example 95 (0.2 g, 0.24 mmol), Dess-Martin reagent (0.112 g, 0.264 mmol) and diisopropylamine (102 μl, 0.72 mmol) the title crude product (0.374 g) was obtained according to the procedure for Example 95. Product was purified by column chromatography (DCM:MeOH:NH4OH=90:9:0.5) to afford the title product (28 mg).

MS m/z: (ES): MH+=916.7.

What is claimed is:

1. A compound of Formula (I)

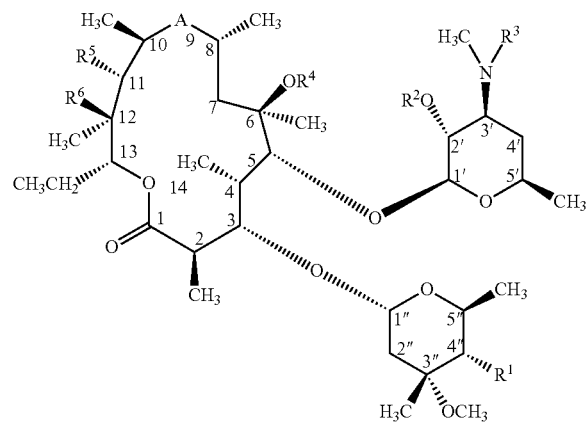

(I)

wherein

A is a bivalent radical selected from —NHC(O) and —C(O)NH—;

R$^1$ is —OC(O)(CH$_2$)$_n$NR$^8$R$^9$, —O—(CH$_2$)$_n$NR$^8$R$^9$, —OC(O)N(R$^7$)(CH$_2$)$_n$NR$^8$R$^9$,

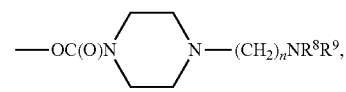

—O(CH$_2$)$_n$CN, —OC(O)(CH$_2$)$_n$ N(CH$_2$)$_n$NR$^8$R$^9$, or —OC(O)CH=CH$_2$ with the proviso that if R$^1$ is —OC(O)CH=CH$_2$, R$^3$ cannot be methyl;

R$^2$ is hydrogen or a hydroxyl protecting group;

R$^3$ is hydrogen, unsubstituted C$_{1-4}$ alkyl or C$_{1-4}$ alkyl substituted at terminal carbon atom with CN or NH$_2$ group, or C$_{1-5}$ alkanoyl;

R$^4$ is hydrogen, C$_{1-4}$ alkyl or C$_{2-6}$ alkenyl;

R$^5$ is hydroxy, methoxy group, —OC(O)(CH$_2$)$_n$NR$^8$R$^9$ or —O—(CH$_2$)$_n$NR$^8$R$^9$, or —O(CH$_2$)$_n$CN;

R$^6$ is hydroxy; or

R$^5$ and R$^6$ taken together with the intervening atoms form a cyclic group having the following structure:

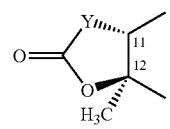

wherein Y is a bivalent radical selected from —CH$_2$—, —CH(CN)—, —O—, —N(R$^7$)— and —CH(SR$^7$)—;

$R^7$ is hydrogen or $C_{1-6}$alkyl;

$R^8$ and $R^9$ are each independently hydrogen, $C_{3-7}$ cycloalkyl, or $C_{1-18}$ alkyl, wherein $C_{1-18}$ alkyl is:

(i) uninterrupted or interrupted by 1-3 bivalent radical groups selected from —O—, —S— and —N($R^7$)—; and/or (ii) unsubstituted or substituted by 1-3 groups selected from halogen, OH, $NH_2$, N—($C_1$-$C_6$)alkylamino, N,N-di($C_1$-$C_6$-alkyl)amino, CN, $NO_2$, $OCH_3$, a $C_{3-8}$ membered non-aromatic ring which is saturated or unsaturated, a non-aromatic heterocyclic ring containing 2-6 carbon atoms which is saturated or unsaturated containing from 1-2 heteroatoms selected from oxygen, sulphur and nitrogen, alkylcarbonylalkoxy and alkoxycarbonylamino; or $R^8$ and $R^9$ taken together with nitrogen to which they are attached form a non-aromatic heterocyclic ring containing 2-6 carbon atoms which is:

(iii) saturated or unsaturated containing from 0 or 1 additional heteroatoms selected from oxygen, sulphur and nitrogen; and/or (iv) unsubstituted or substituted by 1-2 groups selected from $C_{1-5}$ alkanoyl and $C_{1-6}$ alkyl, wherein $C_{1-6}$ alkyl is uninterrupted or is interrupted by 1-3 bivalent radical groups selected from —O—, —S— and —N($R^7$)—, and/or being unsubstituted or substituted by 1-2 groups selected from OH, $NH_2$, a non-aromatic heterocyclic ring containing 2-6 carbon atoms which is unsubstituted or is substituted by group selected from $C_{1-4}$ alkyl, halo, $NH_2$, OH, SH, $C_{1-6}$ alkoxy and $C_{1-4}$ hydroxyalkyl, a $C_{3-7}$ cycloalkyl which is unsubstituted or is substituted by group selected from $C_{1-4}$ alkyl, halo, $NH_2$, OH, SH, $C_{1-6}$ alkoxy and $C_{1-4}$ hydroxyalkyl;

n is an integer from 1 to 8 or a pharmaceutically acceptable salt thereof.

2. A compound of Formula (I) according to claim 1 wherein

A is a bivalent radical selected from —NHC(O)— and —C(O)NH—;

$R^1$ is —OC(O)($CH_2$)$_n$$NR^8R^9$, —O—($CH_2$)$_n$$NR^8R^9$, or —OC(O)CH═$CH_2$ with the proviso that if $R^1$ is —OC(O)CH═$CH_2$, $R^3$ cannot be methyl;

$R^2$ is hydrogen or a hydroxyl protecting group;

$R^3$ is unsubstituted $C_{1-4}$ alkyl or $C_{1-4}$ alkyl substituted at terminal carbon atom with CN or $NH_2$ group, or $C_{1-5}$ alkanoyl;

$R^4$ is hydrogen, $C_{1-4}$ alkyl or $C_{2-6}$ alkenyl;

$R^5$ is hydroxy, methoxy group, —OC(O)($CH_2$)$_n$$NR^8R^9$ or —O—($CH_2$)$_n$$NR^8R^9$;

$R^6$ is hydroxy; or $R^5$ and $R^6$ taken together with the intervening atoms form a cyclic group having the following structure:

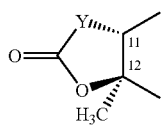

wherein Y is a bivalent radical selected from —$CH_2$—, —CH(CN)—, —O—, —N($R^7$)— and —CH(S$R^7$)—;

$R^7$ is hydrogen or $C_{1-6}$alkyl;

$R^8$ and $R^9$ are each independently hydrogen, $C_{3-7}$ cycloalkyl, or $C_{1-18}$ alkyl, wherein $C_{1-18}$ alkyl is:

(i) uninterrupted or interrupted by 1-3 bivalent radical groups selected from —O—, —S— and —N($R^7$)—; and/or (ii) unsubstituted or substituted by 1-3 groups selected from halogen, OH, $NH_2$, N—($C_1$-$C_6$)alkylamino, N,N-di($C_1$-$C_6$-alkyl)amino, CN, $NO_2$, $OCH_3$, a $C_{3-8}$ membered non-aromatic ring which is saturated or unsaturated, a non-aromatic heterocyclic ring containing 2-6 carbon atoms which is saturated or unsaturated containing from 1-2 heteroatoms selected from oxygen, sulphur and nitrogen, alkylcarbonylalkoxy and alkoxycarbonylamino; or $R^8$ and $R^9$ taken together with nitrogen to which they are attached form a non-aromatic heterocyclic ring containing 2-6 carbon atoms which is:

(iii) saturated or unsaturated containing from 0 or 1 additional heteroatoms selected from oxygen, sulphur and nitrogen; and/or (iv) unsubstituted or substituted by 1-2 groups selected from $C_{1-5}$alkanoyl and $C_{1-6}$ alkyl, wherein $C_{1-6}$ alkyl is uninterrupted or is interrupted by 1-3 bivalent radical groups selected from —O—, —S— and —N($R^7$)—, and/or being unsubstituted or substituted by 1-2 groups selected from OH, $NH_2$, a non-aromatic heterocyclic ring containing 2-6 carbon atoms which is unsubstituted or is substituted by group selected from $C_{1-4}$ alkyl, halo, $NH_2$, OH, SH, $C_{1-6}$ alkoxy and $C_{1-4}$ hydroxyalkyl, a $C_{3-7}$ cycloalkyl which is unsubstituted or is substituted by group selected from $C_{1-4}$ alkyl, halo, $NH_2$, OH, SH, $C_{1-6}$ alkoxy and $C_{1-4}$ hydroxyalkyl;

n is an integer from 1 to 8 or a pharmaceutically acceptable salt thereof.

3. The compound of claim 1 wherein $R^1$ is —OC(O)($CH_2$)$_n$$NR_8R_9$ and n is 1-4.

4. The compound of claim 1, wherein $R^8$ and $R^9$ taken together with nitrogen to which they are attached form a $C_{5-7}$ membered saturated non-aromatic heterocyclic ring.

5. The compound of claim 1, wherein $R^3$ is H.

6. The compound of claim 5, wherein $R^1$ is —O—C(O)—CH═$CH_2$ or —O—C(O)—($CH_2$)$_n$—N($C_{1-4}$alkyl)$_2$.

7. The compound of claim 2, wherein $R^5$ is OH or $R^5$ and $R^6$ taken together with the intervening atoms form a cyclic group having the following structure:

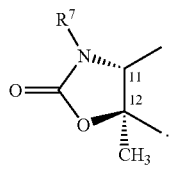

8. A process for the preparation of a compound of Formula (I) as claimed in claim 1 which comprises one of steps (a)-(g):

a) reacting a compound of formula (II)

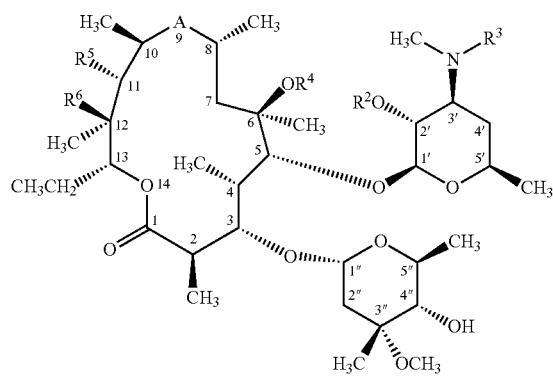
(I)

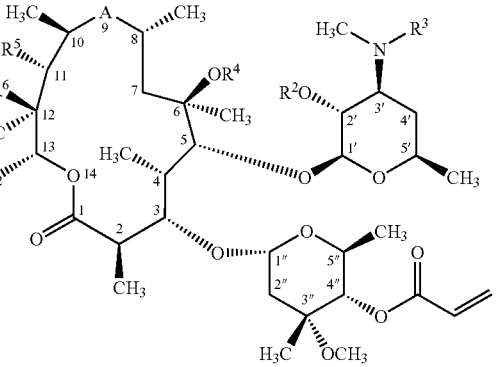
(VII)

HOC(O)(CH$_2$)$_n$NR$^{8a}$R$^{9a}$     (III)

with an acid (III), wherein R$^{8a}$ and R$^{9a}$ are R$^8$ and R$^9$ as defined in claim 1 or groups convertible to R$^8$ and R$^9$, to produce a compound of formula (I) wherein R$^1$ is —OC(O)(CH$_2$)$_n$NR$^8$R$^9$ and n is an integer from 1 to 8;

b) reacting a compound of formula (IV) wherein n is an integer from 1 to 8 and L is a leaving group, with HNR$^{8a}$R$^{9a}$ (V), wherein R$^{8a}$ and R$^{9a}$ are R$^8$ and R$^9$ as defined in claim 1 or groups convertible to R$^8$ and R$^9$, to produce a compound of formula (I) wherein R$^1$ is —OC(O)(CH$_2$)$_n$NR$^8$R$^9$ and n is an integer from 1 to 8;

d) reacting a compound of formula (VIII) wherein n is an integer from 1 to 7 with a compound of formula HNR$^{8a}$R$^{9a}$ (V), wherein R$^{8a}$ and R$^{9a}$ are R$^8$ and R$^9$ as defined in claim 1 or groups convertible to R$^8$ and R$^9$, to produce a compound of formula (I) wherein R$^1$ is —O—(CH$_2$)$_n$NR$^8$R$^9$ and n is an integer from 1 to 8;

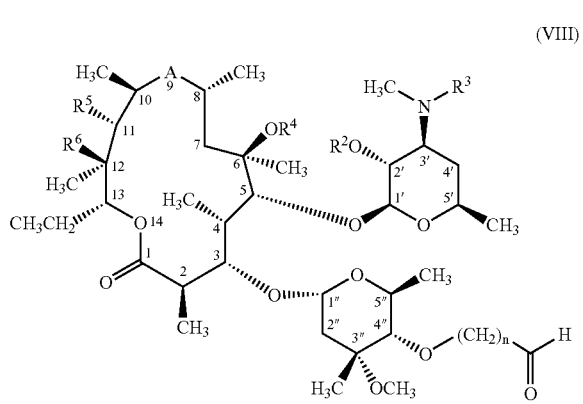
(VIII)

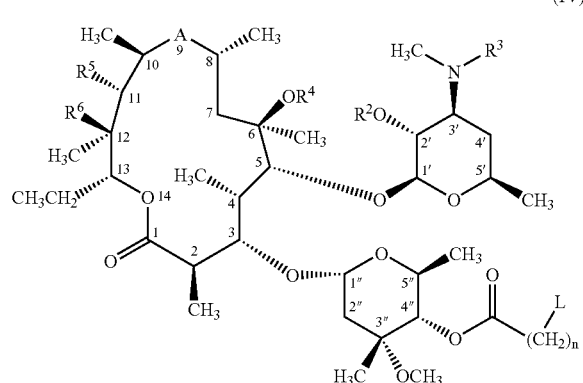
(IV)

e) reacting a compound of formula (X) wherein n is an integer from 2 to 8 and L is suitable leaving group with compound of formula HNR$^{8a}$R$^{9a}$ (V), wherein R$^{8a}$ and R$^{9a}$ are R$^8$ and R$^9$ as defined in claim 1 or groups convertible to R$^8$ and R$^9$, to produce a compound of formula (I) wherein R$^1$ is —O—(CH$_2$)$_n$NR$^8$R$^9$ and n is an integer from 2 to 8;

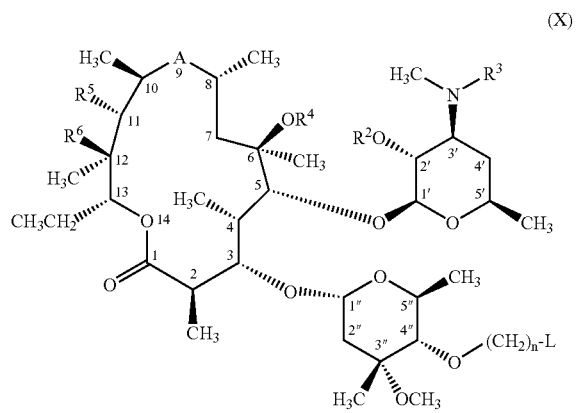
(X)

c) reacting a compound of formula (VII) with a compound of formula HNR$^{8a}$R$^{9a}$ (V), wherein R$^{8a}$ and R$^{9a}$ are R$^8$ and R$^9$ as defined in claim 1 or groups convertible to R$^8$ and R$^9$, to produce a compound of formula (I) wherein R$^1$ is —OC(O)(CH$_2$)$_n$NR$^8$R$^9$ and n is 2;

f) reacting a compound of formula (XI) wherein, Z is $CH_2NH_2$ with a compound of formula $HC(O)R^8$ (XII), to produce a compound of formula (I) wherein $R^1$ is $—O—(CH_2)_nNR^8R^9$, wherein $R^8$ and $R^9$ are the same and have the meaning as defined in claim 1 and n is 3; or

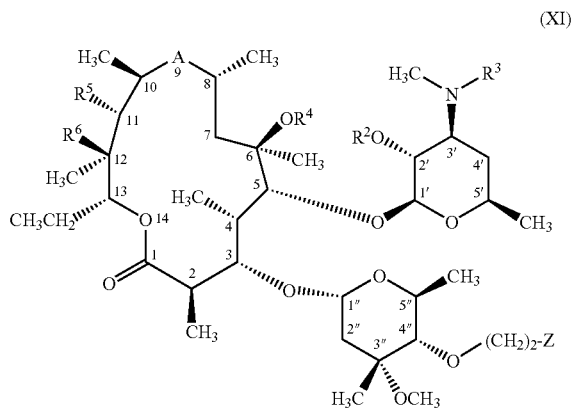

(XI)

g) reacting a compound of formula (XIII) wherein n is an integer from 1 to 8 and $R^{10}$ is an activating group such as imidazolyl or halogen, with the amine of formula (XIVa) or (XIVb), wherein $R^{8a}$ and $R^{9a}$ are $R^8$ and $R^9$ as defined in claim 1 or groups convertible to $R^8$ and $R^9$, to produce a compound of formula (I) wherein $R^1$ is $—OC(O)N(R^7)(CH_2)_nNR^8R^9$ or

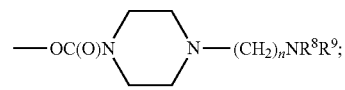

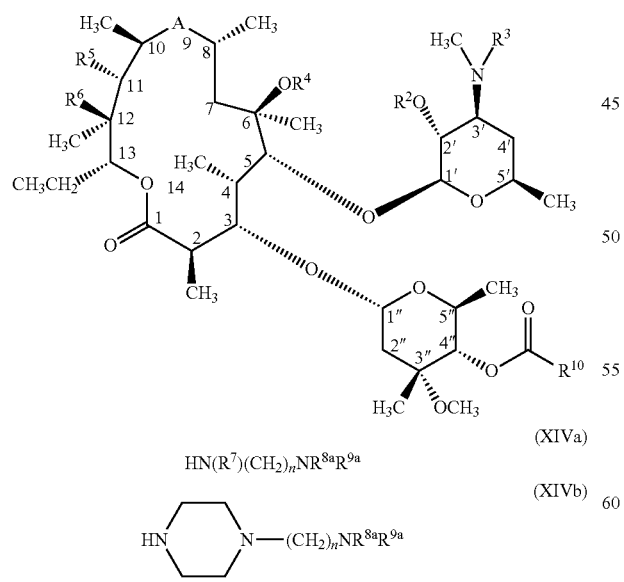

(XIII)

$HN(R^7)(CH_2)_nNR^{8a}R^{9a}$ (XIVa)

(XIVb)

and thereafter, if required after any of steps (a)-(g), subjecting the resulting compound to one or more of the following operations:

(i) removal of the protecting group $R^2$, or
(ii) conversion of $R^{8a}$ and $R^{9a}$ to $R^8$ and $R^9$,
(iii) conversion of the resultant compound of formula (I) into a pharmaceutically acceptable salt thereof.

9. A pharmaceutical composition comprising a compound according to claim 1 or a pharmaceutically acceptable salt thereof and a pharmaceutically acceptable diluent or carrier.

10. A method of inhibiting or relieving an inflammatory disease, disorder or condition characterized by or associated with an undesirable inflammatory immune response, or an excessive secretion of TNF-α, IL-1, IL-6 and IL-8 which comprises administering to a subject in need thereof a therapeutically effective amount of a compound according to claim 1.

11. A method of inhibiting or relieving an inflammatory condition or immune or anaphylactic disorder associated with infiltration of leukocytes into inflamed organ or tissue comprising administering to a subject in need thereof a therapeutically effective amount of the compound of claim 1.

12. The method according to claim 11, wherein the inflammatory condition or immune disorder is selected from the group consisting of asthma, COPD, diffuse panbronchiolitis, adult respiratory distress syndrome, inflammatory bowel disease, Crohn's disease, chronic bronchitis, and cystic fibrosis.

13. A method according to claim 11, wherein said inflammatory condition or immune disorder is selected from the group consisting of asthma, adult respiratory distress syndrome, bronchitis, bronchiectasis, bronchiolitis obliterans, cystic fibrosis, rheumatoid arthritis, rheumatoid spondylitis, osteoarthritis, osteomyelitis, sinusitis, nasal polyps, gouty arthritis, uveitis, conjunctivitis, inflammatory bowel disease, Crohn's disease, ulcerative colitis, distal proctitis, psoriasis, eczema, dermatitis, acne, coronary infarct damage, chronic inflammation, endotoxin shock, chronic sinusitis, pulmonary fibrosis, diffuse panbronchiolitis, and smooth muscle proliferation disorders.

14. A compound selected from the group consisting of:
11,12-Carbonate-11,12-dideoxy-4"-O-(3-diethylamino-propionyl)-azithromycin;
4"-O-(3-Diethylamino-propionyl)-8a-aza-8a-homoerythromycin A;
4"-O-(3-Diethylamino-propionyl)-6-O-methyl-8a-aza-8a-homoerythromycin A;
2'-O-Acetyl-3'-N-methyl-3'-N-(2-cyanoethyl)-4"-O-propenoyl-6-O-methyl-9a-aza-9a-homoerythromycin A;
2'-O-Acetyl-3'-N-methyl-3'-N-(2-cyanoethyl)-4"-O-(3-diethylamino-propionyl)-6-O-methyl-9a-aza-9a-homoerythromycin A;
2'-O-Acetyl-3'-N-methyl-3'-N-(3-aminopropyl)-4"-O-(3-diethylannino-propionyl)-6-O-methy -9a-aza-9a-homoerythromycin A;
4",11-di-O-(3-Diethylamino-propionyl)-6-O-methyl-9a-aza-9a-homoerythromycin A;
4"-O-(3-Diethylamino-propionyl)-6-O-methyl-9a-aza-9a-homoerythromycin A;
11,12-Carbamate-11,12-dideoxy-4"-O-(3-diethylamino-propionyl)-6-O-methyl-erythromycin A;
11,12-(N-Methyl-carbamate)-11,12-dideoxy-4"-O-(3-diethylamino-propionyl)-6-O-methyl-erythromycin A;
4"-O-(3-methylamino-propionyl)-6-O-methyl-9a-aza-9a-homoerythromycin A;
4"-O-(3-dimethylamino-propionyl)-6-O-methyl-9a-aza-9a-homoerythromycin A;
3'-N-Methyl-3'-N-2'-O-diacetyl-4"-O-propenoyl-6-O-methyl-9a-aza-9a-homoerythromycin A;

3'-N-Methyl-3'-N-2'-O-diacetyl-4''-O-(3-diethylamino-propionyl)-6-O-methyl-9a-aza-9a-homoerythromycin A;

3'-N-Methyl-3'-N-(3-aminopropyl)-4''-O-(3-Diethylamino-propionyl)-6-O-methyl-9a-aza-9a -homoerythromycin A;

4''-O-(3-diethylamino-propionyl)-azithromycin;

4''-O-(3-Diethylamino-propionyl)-6-O-methylerithromycin A;

4''-O-(3-Piperazin-1-yl-propionyl)-6-O-methylerithromycin A;

11, 12-Carbonate-11, 12-dideoxy-2'-O-acetyl-4''-O-(2-cyanoethyl)-azithromycin;

11, 12-Carbonate-11, 12-dideoxy-2'-O-acetyl-4''-O-(3-aminopropyl)-azithromycin;

11, 12-Carbonate-11, 12-dideoxy-4''-O-(3-aminopropyl)-azithromycin;

11, 12-Carbonate-11, 12-dideoxy-4''-O-(3-dimethylamino-propyl)-azithromycin;

3''-N-Demethyl-4''-O-acryloyl-6-O-methyl-9a-aza-9a-homoerythromycin A;

3''-N-Demethyl-4''-O-(3-diethylaminopropionyl)-6-O-methyl-9a-aza-9a-homoerythromycin A;

4''-O-(4-Diethylaminobutanoyl)-6-O-methyl-9a-aza-9a-homoerythromycin A;

4''-O-(2-Diethylaminoethanoyl)-6-O-methyl-9a-aza-9a-homoerythromycin A;

3'-N-methyl-3'-N-i-propyl-4''-O-(3-diethylaminopropionyl)-6-O-methyl-9a-aza-9a-homoerythromycin A;

3'-N-methyl-3'-N-(2-cyanoethyl)-4''-O-(3-diethylamino-propionyl)-6-O-methyl-9a-aza-9a-homoentromicin A;

3'-N-methyl-3'-N-acetyl-4''-O-(3-diethylaminopropionyl)-6-O-methyl-9a-aza-9a-homoerythromycin A;

3'-N-methyl-3'-N-propionyl-4''-O-(3-diethylaminopropionyl)-6-O-methyl-9a-aza-9a-homoerythromycin A;

11, 12-carbonate-11, 12-dideoxy-2'-O-acetyl-4''-O-(3-diethylaminopropyl)-6-O-methylerythromycin A 9-oxime;

11, 12-carbonate-11, 12-dideoxy-2'-O-acetyl-4''-O-(3-diethylaminopropyl)-6-O-methylerythromycin A 9-oxime;

4''-O-(3-diethylaminopropyl)-6-O-methylerythromycin A 9-oxime;

4''-O-(3-diethylaminopropyl)-6-O-methylerythromycin A;

11, 12-carbonate-11, 12-dideoxy-2'-O-acetyl-4''-O-(3-aminopropyl)-6-O-methylerythromycin A 9-[O-(1-isopropoxycyclohexyl)]oxime;

11, 12-carbonate-11, 12-dideoxy-2'-O-acetyl-4''-O-(3-aminopropyl)-6-O-methylerythromycin A 9-oxime;

4''-O-(3-aminopropyl)-6-O-methylerythromycin A 9-oxime;

4''-O-(3-aminopropyl)-6-O-methylerythromycin A;

11, 12-carbonate-2'-O-acetyl-4''-O-(2-cyanoethyl)-6-O-methyl-9a-aza-9a-homoerythromycin A;

4''-O-(2-cyanoethyl)-6-O-methyl-9a-aza-9a-homoerythromycin A;

4''-O-(3-aminopropyl)-6-O-methyl-9a-aza-9a-homoerytromycin A;

4''-O-(3-Diethylaminopropyl)-6-O-methyl-9a-aza-9a-homoerythromycin A;

2'-O-Acetyl-4''-O-(2-cyanoethyl)-11-O-methyl-azithromycin;

2'-O-Acetyl-4''-O-(3-aminopropyl)-11-O-methyl-azithromycin;

4''-O-(3-Aminopropyl)-11-O-methyl-azithromycin;

4''-O-[3-(2-Dimethylamino-ethylamino)-propionyl]-6-O-methyl-9a-aza-9a-homoerythromycin A;

4''-O-(3-Diethylamino-propionyl)-11-O-(2-cyano-ethyl)-6-O-methyl-9a-aza-9a-homoerythromycin A;

4''-O-(3-Diethylamino-propionyl)-11-O-(3-aminopropyl)-6-O-methyl-9a-aza-9a-homoerythromycin A;

3'-N-Demethyl-4''-O-propenoyl-azithromycin;

3'-N-Demethyl-4''-O-(3-diethylaminopropionyl)-azithromycin;

3'-N-Demethyl-4''-O-propenoyl-6-O-methyl-erythromycin A 11, 12-cyclic carbamate;

3'-N-Demethyl-4''-O-(3-diethylaminopropionyl)-6-O-methyl-erythromycin A 11, 12-cyclic carbamate;

3'-N-Demethyl-4''-O-propenoyl-6-O-methyl-erythromycin A;

3'-N-Demethyl-4''-O-(3-diethylaminopropionyl)-6-O-methyl-erythromycin A;

4''-O-(3-diethylamino-propyl)-azithromycin 11, 12-cyclic carbonate;

4''-O-(3-diethylamino-propyl)-azithromycin 11, 12-cyclic carbonate;

4''-O-(3-diethylamino-propyl)-azithromycin;

4''-O-{3-[4-(2-Diethylamino-ethyl)-piperazin-1-yl]-propyl} azithromycin 11,12-cyclic carbonate;

4''-O-(3-diisopropylamino-propyl)-azithromycin 11, 12-cyclic carbonate;

and pharmaceutically acceptable salts thereof.

15. A compound of Formula (I) according to claim 1

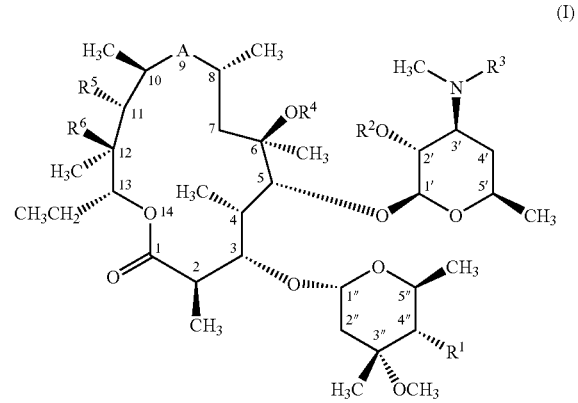

(I)

wherein

A is a bivalent radical selected from —NHC(O)— and —C(O)NH—, $R^1$ is —OC(O)(CH$_2$)$_n$NR$^8$R$^9$, —O—(CH$_2$)$_n$NR$^8$R$^9$—, or —OC(O)CH=CH$_2$;

$R^2$ is hydrogen or an hydroxyl protecting group;

$R^3$ is hydrogen;

$R^4$ is hydrogen, C$_{1-4}$ alkyl or C$_{2-6}$alkenyl;

$R^5$ is hydroxyl, methoxy, —OC(O)(CH2)nNR$^8$R$^9$, or —O—(CH$_2$)$_n$NR$^8$R$^9$;

$R^6$ is hydroxyl; or $R^5$ and $R^6$ taken together with the intervening atoms form a cyclic group having the following structure:

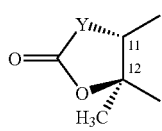

wherein Y is a bivalent radical selected from —CH$_2$—, —CH(CN)—, N(R$^7$)and —CH(SR$^7$)—;

R$^7$ is hydrogen or C$_{1-6}$alkyl;

R$^8$ and R$^9$ are each independently hydrogen or C$_{3-7}$cycloalkyl or C$_{1-18}$ alkyl, wherein $_{C1-18}$alkyl is:
(i) uninterrupted or interrupted by 1-3 bivalent radical groups selected from —O—, —S— and —N(R$^7$)—; and/or
(ii) unsubstituted or substituted by 1-3 groups selected from halogen, OH, NH$_2$, N—(C$_1$-C$_6$)alkylamino, N,N-di(C$_1$-C$_6$-alkyl)amino, CN, NO$_2$, OCH$_3$;, or a C$_{3-8}$ membered non-aromatic ring which is saturated or unsaturated, a non-aromatic heterocyclic ring containing 2-6 carbon atoms which is saturated or unsaturated containing from 1-2 heteroatoms selected from oxygen, sulphur and nitrogen, alkylcarbonylalkoxy and alkoxycarbonylamino; or R$^8$ and R$^9$ taken together with the nitrogen atom to which they are attached form a non-aromatic heterocyclic ring containing 2-6 carbon atoms which is:
(iii) saturated or unsaturated containing from 0 or 1 additional heteroatoms selected from oxygen, sulphur, and nitrogen; and/or
(iv) unsubstituted or substituted by 1-2 groups selected from C$_{1-5}$alkanoyl and C$_{1-6}$ alkyl, wherein C$_{1-6}$ alkyl is uninterrupted or is interrupted by 1-3 bivalent radical groups selected from —O—, —S— and —N(R$^7$)—, and/or being unsubstituted or substituted by 1-2 groups selected from OH, NH$_2$, a non-aromatic heterocyclic ring containing 2-6 carbon atoms as defined above which is unsubstituted or is substituted by group selected from C$_{1-4}$ alkyl, halo, NH$_2$, OH, SH, C$_{1-6}$ alkoxy, C$_{1-4}$ hydroxyalkyl, a C$_{3-7}$cycloalkyl which is unsubstituted or is substituted by a group selected from C$_{1-4}$alkyl, halo, NH$_2$, OH, SH, C$_{1-6}$alkoxy and C$_{1-4}$hydroxyalkyl;

n is an integer from 1 to 8;

or a pharmaceutically acceptable salt thereof.

16. A compound according to claim 15, wherein R$^4$ is hydrogen or methyl.

17. A compound of claim 15, wherein R$^5$ is hydroxy or methoxy and R$^6$ is hydroxy.

18. The method according to claim 11, wherein the inflammatory condition or immune disorder is COPD.

19. The method according to claim 11, wherein the inflammatory condition or immune disorder is asthma.

20. A method of inhibiting or relieving an inflammatory disease, disorder or condition characterized by or associated with an undesirable inflammatory immune response, or an excessive secretion of TNF-α, IL-1, IL-6 and IL-8, in a human comprising administering to said human a compound of formula (I) according to claim 1.

21. A method according to claim 20 wherein the inflammatory condition or immune disorder is selected from the group consisting of asthma, COPD, diffuse panbronchiolitis, adult respiratory distress syndrome, inflammatory bowel disease, Crohn's disease, chronic bronchitis and cystic fibrosis.

22. A method according to claim 20 wherein the inflammatory condition or immune disorder is selected from the group consisting of asthma, adult respiratory distress syndrome, bronchitis, bronchiectasis, bronchiolitis obliterans, cystic fibrosis, rheumatoid arthritis, rheumatoid spondylitis, osteoarthritis, osteomyelitis, sinusitis, nasal polyps, gouty arthritis, uveitis, conjunctivitis, inflammatory bowel disease, Crohn's disease, ulcerative colitis, distal proctitis, psoriasis, eczema, dermatitis, acne, coronary infarct damage, chronic inflammation, endotoxin shock, chronic sinusitis, pulmonary fibrosis, diffuse panbronchiolitis, and smooth muscle proliferation disorders.

23. A method according to claim 20 wherein the inflammatory condition or immune disorder is COPD.

24. A method according to claim 20 wherein the inflammatory condition or immune disorder is asthma.

* * * * *